US011056652B2

(12) United States Patent
Pfister et al.

(10) Patent No.: US 11,056,652 B2
(45) Date of Patent: *Jul. 6, 2021

(54) COMPOUNDS AND ORGANIC ELECTRONIC DEVICES

(71) Applicant: Merck Patent GmbH, Darmstadt (DE)

(72) Inventors: Jochen Pfister, Seeheim-Jugenheim (DE); Frank Stieber, Einhausen (DE); Elvira Montenegro, Weinheim (DE); Teresa Mujica-Fernaud, Darmstadt (DE); Frank Voges, Bad Duerkheim (DE)

(73) Assignee: Merck Patent GmbH, Darmstadt (DE)

( * ) Notice: Subject to any disclaimer, the term of this patent is extended or adjusted under 35 U.S.C. 154(b) by 26 days.

This patent is subject to a terminal disclaimer.

(21) Appl. No.: 16/426,042

(22) Filed: May 30, 2019

(65) Prior Publication Data
US 2019/0288209 A1    Sep. 19, 2019

Related U.S. Application Data

(63) Continuation of application No. 15/101,193, filed as application No. PCT/EP2014/003148 on Nov. 26, 2014, now Pat. No. 10,355,217.

(30) Foreign Application Priority Data

Dec. 6, 2013  (EP) .................................... 13005697

(51) Int. Cl.
| | | |
|---|---|---|
| *H01L 51/00* | (2006.01) | |
| *C09K 11/06* | (2006.01) | |
| *C07C 211/61* | (2006.01) | |
| *C07D 333/76* | (2006.01) | |
| *C07D 209/88* | (2006.01) | |
| *C07D 307/81* | (2006.01) | |
| *C07D 307/91* | (2006.01) | |
| *C07C 209/68* | (2006.01) | |
| *C07D 209/86* | (2006.01) | |
| *H01L 51/50* | (2006.01) | |

(52) U.S. Cl.
CPC .......... *H01L 51/006* (2013.01); *C07C 209/68* (2013.01); *C07C 211/61* (2013.01); *C07D 209/86* (2013.01); *C07D 209/88* (2013.01); *C07D 307/81* (2013.01); *C07D 307/91* (2013.01); *C07D 333/76* (2013.01); *C09K 11/06* (2013.01); *H01L 51/0061* (2013.01); *C07C 2603/18* (2017.05); *C09K 2211/1007* (2013.01); *C09K 2211/1011* (2013.01); *C09K 2211/1029* (2013.01); *C09K 2211/1088* (2013.01); *C09K 2211/1092* (2013.01); *C09K 2211/185* (2013.01); *H01L 51/0058* (2013.01); *H01L 51/0072* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5072* (2013.01); *H01L 51/5088* (2013.01); *Y02E 10/549* (2013.01); *Y02P 70/50* (2015.11)

(58) Field of Classification Search
CPC .............. H01L 51/006; H01L 51/0061; H01L 51/0072; H01L 51/5012; H01L 51/5072; H01L 51/5056; H01L 51/5088; H01L 51/5016; H01L 51/0074; C07D 209/86; C07D 333/76; C07D 209/88; C07D 307/81; C07D 307/91; Y02P 70/50; C07C 2603/18; C07C 209/68; C07C 211/61; C09K 2211/185; C09K 11/06; Y02E 10/549

USPC ........................................................ 252/500
See application file for complete search history.

(56) References Cited

U.S. PATENT DOCUMENTS

| | | | |
|---|---|---|---|
| 7,241,513 B2 | 7/2007 | Suzuki et al. | |
| 8,691,398 B2 | 4/2014 | Yamada et al. | |
| 9,139,522 B2 | 9/2015 | Yabunouchi et al. | |
| 9,278,926 B2 | 3/2016 | Kato | |
| 9,595,681 B2* | 3/2017 | Mujica-Fernaud | ........................ H01L 51/0067 |
| 9,768,391 B2* | 9/2017 | Mujica-Fernaud | ........................ H01L 51/0039 |
| 9,773,979 B2* | 9/2017 | Parham | ................. H01L 51/006 |
| 9,882,142 B2* | 1/2018 | Mujica-Fernaud | .... C09K 11/06 |
| 2011/0198581 A1 | 8/2011 | Yabunouchi et al. | |
| 2012/0068170 A1* | 3/2012 | Pflumm | ............... C07D 413/04 257/40 |
| 2013/0207046 A1 | 8/2013 | Pflumm et al. | |
| 2014/0148877 A1 | 5/2014 | Pan et al. | |
| 2014/0203216 A1 | 7/2014 | Parham et al. | |
| 2014/0275602 A1 | 9/2014 | Irwin et al. | |
| 2015/0179940 A1* | 6/2015 | Mujica-Fernaud | ........................ H01L 51/0072 252/519.21 |
| 2015/0179953 A1 | 6/2015 | Mujica-Fernaud et al. | |
| 2016/0176801 A1 | 6/2016 | Kato et al. | |
| 2016/0301005 A1 | 10/2016 | Pfister et al. | |
| 2017/0317285 A1* | 11/2017 | Mujica-Fernaud | ........................ H01L 51/0052 |
| 2018/0123042 A1* | 5/2018 | Cha | ......................... H01L 51/00 |

FOREIGN PATENT DOCUMENTS

| | | |
|---|---|---|
| EP | 2502908 A1 | 9/2012 |
| JP | 2004-083481 A | 3/2004 |

(Continued)

OTHER PUBLICATIONS

CAS No. 86-73-7, Nov. 16, 1984. (Year: 1984).

(Continued)

*Primary Examiner* — Douglas J McGinty
(74) *Attorney, Agent, or Firm* — Faegre Drinker Biddle & Reath LLP

(57) ABSTRACT

The present invention relates to certain fluorenes, to the use of the compounds in an electronic device, and to an electronic device comprising at least one of these compounds. Furthermore, the present invention relates to a process for the preparation of the compounds and to a formulation and composition comprising one or more of the compounds.

14 Claims, No Drawings

(56) References Cited

FOREIGN PATENT DOCUMENTS

| JP | 2007311759 | A | 11/2007 |
|---|---|---|---|
| JP | 2008019238 | A | 1/2008 |
| JP | 2012521414 | A | 9/2012 |
| JP | 2013513555 | A | 4/2013 |
| JP | 2013539205 | A | 10/2013 |
| JP | 2017-501144 | A | 1/2017 |
| JP | 6382193 | B2 | 8/2018 |
| JP | 6680675 | B2 | 4/2020 |
| JP | 6695936 | B2 | 5/2020 |
| KR | 20110069077 | A | 6/2011 |
| KR | 20120011445 | A | 2/2012 |
| KR | 2012-0066076 | A | 6/2012 |
| KR | 2017-0027691 | A | 3/2017 |
| KR | 2017-0030449 | A | 3/2017 |
| WO | WO-2007123259 | A1 | 11/2007 |
| WO | WO-2010044130 | A1 | 4/2010 |
| WO | WO-2010110553 | A2 | 9/2010 |
| WO | WO-2012003482 | A2 | 1/2012 |
| WO | WO-2012015265 | A1 | 2/2012 |
| WO | WO-2013017192 | A1 | 2/2013 |
| WO | WO-2013120577 | A1 | 8/2013 |
| WO | WO-2014015935 | A2 | 1/2014 |
| WO | WO-2014015937 | A1 | 1/2014 |
| WO | WO-2014015938 | A1 | 1/2014 |
| WO | 2015/082056 | A1 | 6/2015 |
| WO | 2015/084114 | A1 | 6/2015 |

OTHER PUBLICATIONS

Aldrich catalog, Sigma-Aldrich (2009-2010).
International Preliminary Report on Patentability received for PCT Patent Application No. PCT/EP2014/003148, dated Jun. 16, 2016, 13 pages (6 pages of English Translation and 7 pages of Original Document).
International Search Report and Written Opinion received for PCT Patent Application No. PCT/EP2014/003148, dated Mar. 4, 2015, 15 pages (7 pages of English Translation and 8 pages of Original Document).
Korean Office Action for Korean Patent No. 10-1772371, dated Jan. 23, 2018.
Maiti et al., "Palladium-catalyzed coupling of functionalized primary and secondary amines with aryl and heteroaryl halides: two ligands suffice in most cases", Chem. Sci., vol. 2, 2011, pp. 57-68.
Mitsuhiro Koden, "OLED Displays and Lighting", Jang In-bae, CIR Co. Ltd, vol. 21, 2018.
Schlummer et al., Palladium-Catalyzed C N and C O Coupling—A Practical Guide from an Industrial Vantage Point, Adv. Synth. Catal., vol. 346, 2004, pp. 1599-1626.

* cited by examiner

COMPOUNDS AND ORGANIC ELECTRONIC DEVICES

CROSS-REFERENCE TO RELATED APPLICATIONS

This application is a continuation of U.S. Ser. No. 15/101,193, filed Jun. 2, 2016 which is a national stage application (under 35 U.S.C. § 371) of PCT/EP2014/003148, filed Nov. 26, 2014, which claims benefit of European Application No. 13005697.1, filed Dec. 6, 2013, all of which are incorporated herein by reference in their entirety.

The present invention relates to novel organic compounds, to the use of the compounds in an electronic device, and to an electronic device comprising at least one of the compounds. Furthermore, the present invention relates to a process for the preparation of the compounds and to compositions and formulations comprising at least one of the compounds.

The development of functional compounds for use in electronic devices is currently the subject of intensive research. The aim here is, in particular, the development of compounds with which improved properties of the electroluminescent devices in one or more relevant points can be achieved, such as, for example, power efficiency, lifetime or colour coordinates of the emitted light.

The term electronic device in accordance with the present invention is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are well known to the person skilled in the art and are described, inter alia, in U.S. Pat. Nos. 4,539,507, 5,151,629, EP 0676461 and WO 1998/27136.

Still further improvements are necessary with regard to the performance data of OLEDs, in particular in view of broad commercial use, for example in display devices or as light sources. Of particular importance in this connection are the lifetime, the efficiency and the operating voltage of the OLEDs and the colour values achieved. In addition, it is desirable for the compounds for use as functional materials in electronic devices to have high thermal stability and a high glass-transition temperature and to be sublimable without decomposition.

In this connection, there is a need, in particular, for alternative hole-transport materials. In the case of hole-transport materials in accordance with the prior art, the voltage generally increases with increasing layer thickness of the hole-transport layer. In practice, a greater layer thickness of the hole-transport layer would frequently be desirable, but this often has the consequence of a higher operating voltage and worse performance data. In this connection, there is a need for novel hole-transport materials which have high charge-carrier mobility, enabling thicker hole-transport layers to be achieved with only a slight increase in the operating voltage.

The prior art describes the use of various fluorenes as charge-transport material in electronic and electroluminescent devices.

WO 2011/055493 discloses secondary amines which are polysubstituted by fluorenes in position 3.

JP 2008-34701 and WO 2007/072952 disclose fluorenes which are substituted by an amine group in position 4, where the amine group itself again contains a number of fluorenes.

WO 2010/110553 discloses fluorenes which are substituted by amine groups in position 2, 3 or 4, where the amine groups contain carbazole groups.

JP 05303221 discloses fluorenes which may be substituted by an amine group in position 2 or 4. The compounds containing the amine group in position 4 of the fluorene contain phenyl radicals. The compounds are employed as photoreceptors.

In spite of the compounds that are already known, there continues to be a need for novel hole-transport and hole-injection materials for use in OLEDs. In particular, there is a need for materials with which the above-mentioned, highly desired improvements in the performance data and properties of the OLEDs can be achieved.

There is likewise a need for novel matrix materials for use in OLEDs and in other electronic devices. In particular, there is a need for matrix materials for phosphorescent dopants and for matrix materials for mixed-matrix systems which preferably result in good efficiency, a long lifetime and a low operating voltage of the electronic devices.

The present invention is thus based on the object of providing electroluminescent devices and compounds which are suitable for use in electroluminescent devices, such as, for example, in fluorescent or phosphorescent OLEDs, and which can be employed, in particular, as hole-transport materials and/or as hole-injection materials in a hole-transport or exciton-blocking layer or as matrix material in an emitting layer.

In the course of the present invention, it has surprisingly been found that compounds of the formula (1) shown below are extremely suitable for the above-mentioned uses in electronic and in particular in electroluminescent devices.

The invention thus relates to a compound of the general formula (1)

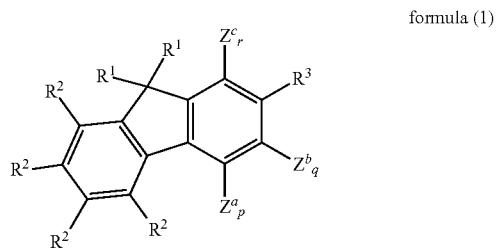

formula (1)

where the following applies to the symbols and indices used:
R$^1$ is on each occurrence, identically or differently, preferably identically, H, D, F, Cl, Br, I, C(=O)R$^4$, CN, Si(R$^4$)$_3$, NO$_2$, P(=O)(R$^4$)$_2$, S(=O)R$^4$, S(=O)$_2$R$^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^4$ and where one or more CH$_2$ groups in the above-mentioned groups may be replaced by —R$^4$C=CR$^4$—, —C≡C—, Si(R$^4$)$_2$, C=O, C=S, C=NR$^4$, —O(=O)O—, —C(=O)NR$^4$—, P(=O)(R$^4$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals R$^4$, or an aryloxy group having 5 to 60 aromatic ring atoms, which may be substituted by one or more radicals R$^4$, or an aralkyl group having 5 to 60 aromatic ring atoms, which may in each case be substituted by one or more radicals R$^4$, where the two radicals R$^1$ may be linked to one another and may form a ring, so that a spiro compound forms in position 9 of the fluorene, where spirobifluorenes are excluded;

R$^2$, R$^3$ are on each occurrence, identically or differently, preferably identically, H, D, F, Cl, Br, I, C(=O)R$^4$, CN, Si(R$^4$)$_3$, NO$_2$, P(=O)(R$^4$)$_2$, S(=O)R$^4$, S(=O)$_2$R$^4$, N(R$^4$)$_2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^4$ and where one or more CH$_2$ groups in the above-mentioned groups may be replaced by —R$^4$C=CR$^4$—, —C≡C—, Si(R$^4$)$_2$, C=O, C=S, C=NR$^4$, —C(=O)O—, —C(=O)NR$^4$—, P(=O)(R$^4$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals R$^4$, or an aryloxy group having 5 to 60 aromatic ring atoms, which may be substituted by one or more radicals R$^4$, or an aralkyl group having 5 to 60 aromatic ring atoms, which may in each case be substituted by one or more radicals R$^4$, where two or more radicals R$^2$ or two or more radicals R$^3$ may be linked to one another and may form a ring;

R$^4$ is on each occurrence, identically or differently, H, D, F, Cl, Br, I, C(=O)R$^5$, CN, Si(R$^5$)$_3$, NO$_2$, P(=O)(R$^5$)$_2$, S(=O)R$^5$, S(=O)$_2$R$^5$, N(R$^5$)$_2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^5$ and where one or more CH$_2$ groups in the above-mentioned groups may be replaced by —R$^5$C=CR$^5$—, —C≡C—, Si(R$^5$)$_2$, C=O, C=S, C=NR$^5$, —C(=O)O—, —C(=O)NR$^5$—, P(=O)(R$^5$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals R$^5$, or an aryloxy or heteroaryloxy group having 5 to 30 aromatic ring atoms, which may be substituted by one or more radicals R$^5$;

R$^5$ is selected from the group consisting of H, D, F, an aliphatic hydrocarbon radical having 1 to 20 C atoms or an aromatic or heteroaromatic ring system having 5 to 30 C atoms, in which one or more H atoms may be replaced by D or F, where two or more adjacent substituents R$^5$ may form a mono- or polycyclic, aliphatic ring system with one another;

p, q, r are 0 or 1, where p+q+r=1, preferably p=1 or r=1 and very preferably p=1;

$Z^a_0$, $Z^b_0$, $Z^c_0$ are, identically or differently on each occurrence, equal to R$^3$;

$Z^a_1$, $Z^b_1$, $Z^c_1$ are equal to

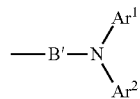

B' is an arylene group having 6 to 30 ring atoms or a heteroarylene group having 5 to 30 ring atoms, each of which may be substituted by one or more radicals R$^4$, preferably B' is an arylene group having 6 to 30 ring atoms or a mono- or bicyclic heteroarylene group having 5 to 30 ring atoms, each of which may be substituted by one or more radicals R$^4$, very preferably a phenylene, biphenylene, terphenylene, naphthylene, pyridinylene, pyrimidinylene, pyrazinylene, pyridazinylene, triazinylene, fluorenylene, dibenzofuranylene or dibenzothiophenylene group, which may be substituted by one or more radicals R$^4$, particularly preferably a phenylene, biphenylene, terphenylene, naphthylene, dibenzofuranylene or dibenzothiophenylene group, which may be substituted by one or more radicals R$^4$, very particularly preferably B' is a phenylene group, which may be substituted by one or more radicals R$^4$, especially preferably B' is a phenylene group which is unsubstituted;

Ar$^1$, Ar$^2$ are on each occurrence, identically or differently, an aromatic group having 6 to 60 ring atoms or a heteroaromatic group having 5 to 60 ring atoms, each of which may be substituted by one or more radicals R$^6$, which are identical to or different from one another, where at least one of the two groups Ar$^1$ and Ar$^2$ must contain a fluorene group;

where two aromatic or heteroaromatic rings in Ar$^1$ or two aromatic or heteroaromatic rings in Ar$^2$ may additionally be condensed, but preferably there is no additional condensation; and where two aromatic or heteroaromatic rings in Ar$^1$ may additionally be bridged by a divalent group —O—, —S—, C(R$^6$)$_2$ or —Si(R$^6$)$_2$—, where bridging via —O—, C(R$^6$)$_2$ or —Si(R$^6$)$_2$— is preferred, or two aromatic or heteroaromatic rings in Ar$^2$ may be bridged by a divalent group —O—, —S—, C(R$^6$)$_2$ or —Si(R$^6$)$_2$—, where bridging via —O—, C(R$^6$)$_2$ or —Si(R$^6$)$_2$— is preferred, where it is very preferred for no additional bridging of the rings to be present in Ar$^1$ and for no additional bridging of the rings to be present in Ar$^2$;

bridging of the rings in Ar$^1$ or in Ar$^2$ by —O— here means that, for example, a dibenzofuran is formed; correspondingly, bridging by —S—, for example, may form a dibenzothiophene; bridging by C(R$^6$)$_2$ may result, for example, in a further fluorene group or an indenofluorene group forming; an indenofluorene group may form if a phenylfluorene is bridged by the group C(R$^6$)$_2$;

and where an aromatic or heteroaromatic ring from Ar$^1$ may be bridged to an aromatic or heteroaromatic ring from Ar$^2$ by a divalent group —O—, —S—, —Si(R$^6$)$_2$—, —NR$^6$— or —C(R$^6$)$_2$—, where it is preferred for the group Ar$^1$ not to be bridged to the group Ar$^2$;

and where it is furthermore preferred for Ar$^1$ and Ar$^2$ to contain at least two aromatic or heteroaromatic rings;

R$^6$ is on each occurrence, identically or differently, H, D, F, Cl, Br, I, C(=O)R$^5$, CN, Si(R$^5$)$_3$, NO$_2$, P(=O)(R$^5$)$_2$, S(=O)R$^5$, S(=O)$_2$R$^5$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^5$ and where one or more CH$_2$ groups in the above-mentioned groups may be replaced by —$R^5$C=C$R^5$—, —C≡C—, Si($R^5$)$_2$, C=O, C=S, C=N$R^5$, —C(=O)O—, —C(=O)N$R^5$—, P(=O)($R^5$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals $R^5$, or an aryloxy or heteroaryloxy group having 5 to 30 aromatic ring atoms, which may be substituted by one or more radicals $R^5$.

The above definitions make it clear that the compound of the formula (1) according to the invention in each case contains at least one fluorene group in either the group $Ar^1$ or in the group $Ar^2$. The above addition "additionally" in the definitions of the groups $Ar^1$ and $Ar^2$ therefore clarifies that the at least one fluorene group necessary in the groups $Ar^1$ and $Ar^2$ is excluded from the preferred embodiments of the unbridged rings in $Ar^1$ and $Ar^2$, i.e. the compound of the formula (1) in each case contains at least one fluorene group in either $Ar^1$ or in $Ar^2$.

In a preferred embodiment, both $Ar^1$ and $Ar^2$ each contain a fluorene group.

It is very preferred for the compound of the general formula (1) in the groups $Ar^1$ and $Ar^2$ to contain no carbazoles, where it is still more preferred for the compound of the general formula (1) to contain absolutely no carbazoles.

In a very preferred embodiment of the present invention, only one of the two groups $Ar^1$ and $Ar^2$ contains a fluorene group.

In a furthermore preferred embodiment, the compound of the formula (1) contains no benzannelated phenyls having more than 12 connected aromatic ring atoms. Benzannelated phenyls in the present application are taken to mean groups which are obtained by condensation of two or more benzenes. These include, for example, naphthalyl, anthracenyl, tetracenyl, pentacenyl and pyrenyl groups.

In a furthermore preferred embodiment, the compound of the formula (1) contains no condensed aromatic groups having more than 13 connected ring atoms.

It is furthermore preferred for the compound of the formula (1) to contain no condensed aromatic groups having more than 13 connected ring atoms and no condensed heteroaromatic groups having more than 13 connected ring atoms, where it is still more preferred for the compound of the general formula (1) to contain absolutely no condensed aromatic or heteroaromatic groups.

The fluorenes in the compound of the formula (1) here do not count amongst the condensed aromatic groups, since two phenyl have been condensed onto one aliphatic ring.

Connected ring atoms in the present application are taken to mean those which are connected to one another exclusively via ring bonds. In this respect, 2-phenylnaphthalene contains one ring (phenyl ring) having 6 connected ring atoms and one ring having 10 connected ring atoms. 2-Phenylnaphthalene therefore contains a maximum of 10 connected ring atoms. Correspondingly, 2-naphthylanthracene contains 14 connected ring atoms.

The numbering on the fluorene is defined as follows.

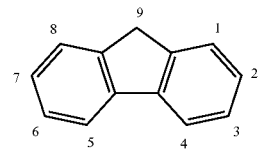

An aryl group (aromatic group) in the sense of this invention contains 6 to 60 aromatic ring atoms; a heteroaryl group (heteroaromatic group) in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S.

An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp³-hybridised C, Si, N or O atom, an sp²-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyl-triazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphta-cene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, hep-tenyl, cycloheptenyl, octenyl, cyclooctenyl, ethynyl, propynyl, butynyl, pen-tynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cyclo-heptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclo-octylthio, 2-ethylhexylthio, trifluoromethylthio, pentafluoroethylthio, 2,2,2-trifluoroethylthio, ethenylthio, propenylthio, butenylthio, pentenylthio, cyclo-pentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

B' in the compound of the formula (1) is furthermore preferably an o-phenylene, m-phenylene or p-phenylene group, a 1,4-naphthylene, 2,4-naphthylene, 1,5-naphthylene or 2,6-naphthylene group, a 2,8-dibenzofuranylene group or a 2,8-dibenzothiophenylene group, or a 2,7-fluorene group, where B' is very preferably an o-phenylene, m-phenylene or p-phenylene group and B' is particularly preferably a p-phenylene group, where the groups may be substituted by one or more radicals $R^4$, which may be identical or different on each occurrence, where the groups are preferably unsubstituted.

For the purposes of the present invention, preference is given to a compound of the general formula (2)

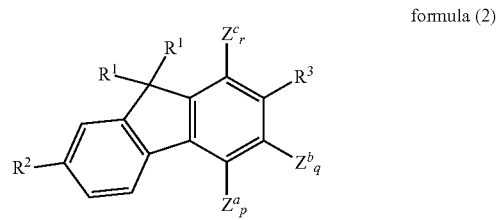

formula (2)

where the above definitions apply to the indices and symbols used.

Preference is furthermore given to a compound of the general formula (1) or (2), characterised in that $R^1$ is on each occurrence, identically or differently, preferably identically, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$, or an aromatic or heteroaromatic ring system having 5 to 30 aromatic ring atoms, which may in each case be substituted by one or more radicals $R^4$, or an aryloxy group having 5 to 60 aromatic ring atoms, which may be substituted by one or more radicals $R^4$, or an aralkyl group having 5 to 60 aromatic ring atoms, which may in each case be substituted by one or more radicals $R^4$, where the two radicals $R^1$ may be linked to one another and may form a ring, so that a spiro compound forms in position 9 of the fluorene, where spirobifluorenes are excluded.

Particular preference is furthermore given to a compound of the general formula (1) or (2), characterised in that $R^1$ is on each occurrence, identically or differently, preferably identically, a straight-chain alkyl group having 1 to 20 C atoms or a branched or cyclic alkyl group having 3 to 20 C atoms, where the above-mentioned groups may each be substituted by one or more radicals $R^4$, or an aromatic or heteroaromatic ring system having 6 to 30 aromatic ring atoms, which may in each case be substituted by one or more radicals $R^4$, where the two radicals $R^1$ may be linked to one another and may form a ring, so that a spiro compound forms in position 9 of the fluorene, where spirobifluorenes are excluded.

Very particular preference is furthermore given to a compound of the general formula (1) or (2), characterised in that $R^1$ is on each occurrence, identically, a straight-chain alkyl group having 1 to 20 C atoms or a branched or cyclic alkyl group having 3 to 20 C atoms, where the above-mentioned groups may each be substituted by one or more radicals $R^4$, where it is especially preferred for $R^1$ to be a methyl, ethyl, n-/i-propyl or n-/i-/t-butyl group.

Finally, very particular preference is furthermore given to a compound of the general formula (1) or (2), characterised in that $R^1$ is on each occurrence an aromatic or heteroaromatic ring system having 6 to 30 aromatic ring atoms, which may in each case be substituted by one or more radicals $R^4$, where the ring system is especially preferably selected from the group consisting of a phenyl, biphenyl, terphenyl or pyridyl group.

The two radicals $R^1$ located in position 9 of the fluorene may be identical or different, where it is preferred for them to be identical.

Preference is furthermore given to a compound of the general formula (1) or (2), characterised in that $R^2$ is selected on each occurrence, identically or differently, preferably identically, from H, D, F, Cl, Br, I, $N(R^5)_2$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^4$, or an aryloxy group having 5 to 60 aromatic ring atoms, which may be substituted by one or more radicals $R^4$, or an aralkyl group having 5 to 60 aromatic ring atoms, which may in each case be substituted by one or more radicals $R^4$, where two or more radicals $R^2$ may be linked to one another and may form a ring.

Particular preference is furthermore given to a compound of the general formula (1) or (2), characterised in that $R^2$ is selected on each occurrence, identically or differently, preferably identically, from H, D, F, Cl, Br, I, $N(R^5)_2$, a straight-chain alkyl group having 1 to 20 C atoms or a branched or cyclic alkyl group having 3 to 20 C atoms, where the above-mentioned groups may each be substituted by one or more radicals $R^4$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^4$.

In a very particularly preferred embodiment, the present invention relates to a compound of the general formula (1) which is characterised in that $R^2$ is equal to H.

In a further very particularly preferred embodiment, the present invention relates to a compound of the general formula (1) which is characterised in that $R^2$ is a straight-chain alkyl group having 1 to 20 C atoms or a branched or cyclic alkyl group having 3 to 20 C atoms.

In still a further very particularly preferred embodiment, the present invention relates to a compound of the general formula (1) which is characterised in that $R^2$ represents an aromatic or heteroaromatic ring system having 6 to 30 aromatic ring atoms.

Preference is furthermore given to a compound of the general formula (1) or (2), characterised in that $R^3$ is selected on each occurrence, identically or differently, from H, D, F, Cl, Br, I, $N(R^5)_2$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^4$, or an aryloxy group having 5 to 60 aromatic ring atoms, which may be substituted by one or more radicals $R^4$, or an aralkyl group having 5 to 60 aromatic ring atoms, which may in each case be substituted by one or more radicals $R^4$, where two or more radicals $R^3$ may be linked to one another and may form a ring.

For the purposes of the present invention, preference is given to a compound of the general formula (1a)

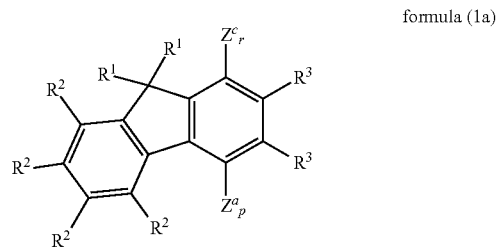

formula (1a)

where the above definitions apply to the symbols and indices used and the preferred embodiments described herein.

For the purposes of the present invention, particular preference is given to a compound of the general formula (2a)

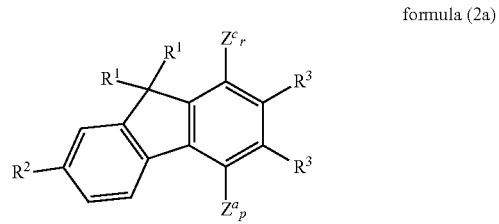

formula (2a)

where the above definitions for the symbols and indices used, and the preferred embodiments described herein apply.

In a preferred embodiment, the present invention relates to a compound of the general formula (3)

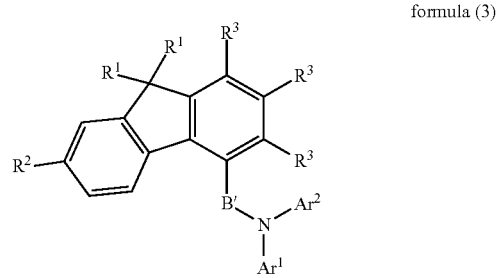

formula (3)

where the above definitions apply to the symbols and indices used.

In a furthermore preferred embodiment, the present invention relates to a compound of the general formula (4)

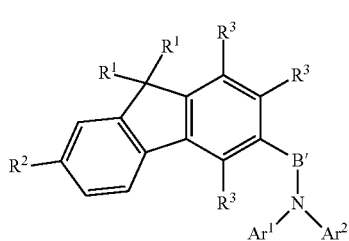

formula (4)

where the above definitions apply to the symbols and indices used.

If the amine containing the groups Ar¹ and Ar² is located in position 3 of the fluorene, it is particularly preferred for the group Ar¹ or the group Ar² to have no bridging via oxygen, since the use of these compounds in OLEDs results in particularly advantageous performance data.

In a furthermore preferred embodiment, the present invention relates to a compound of the general formula (5)

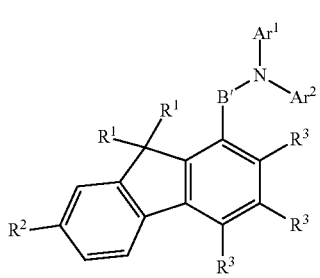

formula (5)

where the above definitions apply to the symbols and indices used.

In a very preferred embodiment, the present invention relates to a compound of the general formula (6)

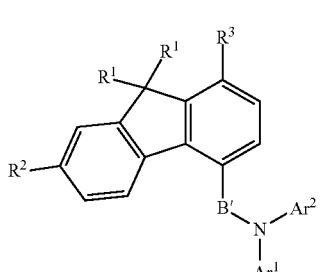

formula (6)

where the above definitions apply to the symbols and indices used.

In a furthermore very preferred embodiment, the present invention relates to a compound of the general formula (7)

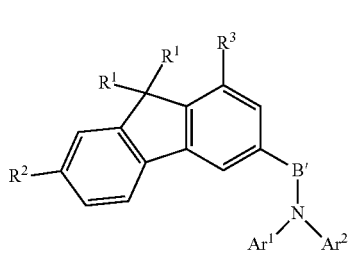

formula (7)

where the above definitions apply to the symbols and indices used.

In a furthermore very preferred embodiment, the present invention relates to a compound of the general formula (8)

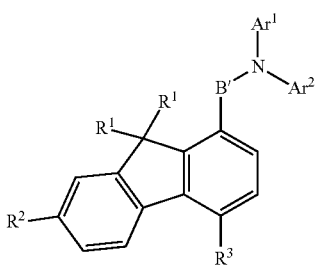

formula (8)

where the above definitions apply to the symbols and indices used.

In a very particularly preferred embodiment, the present invention relates to a compound of the general formula (9)

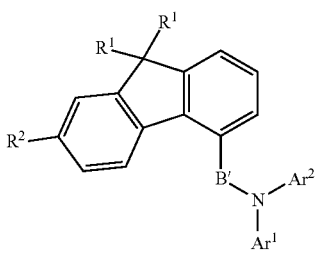

formula (9)

where the above definitions apply to the symbols and indices used.

In a furthermore very particularly preferred embodiment, the present invention relates to a compound of the general formula (10)

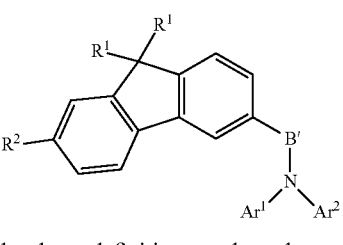

formula (10)

where the above definitions apply to the symbols and indices used.

In a furthermore very particularly preferred embodiment, the present invention relates to a compound of the general formula (11)

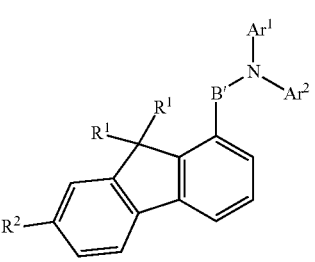

formula (11)

where the above definitions apply to the symbols and indices used.

In an especially preferred embodiment, the present invention relates to a compound of the general formula (12)

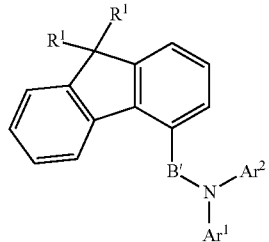

formula (12)

where the above definitions apply to the symbols and indices used.

In a furthermore especially preferred embodiment, the present invention relates to a compound of the general formula (13)

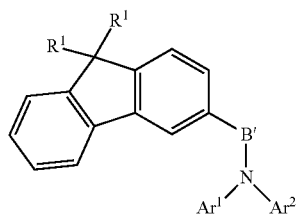

formula (13)

where the above definitions apply to the symbols and indices used.

In a furthermore especially preferred embodiment, the present invention relates to a compound of the general formula (14)

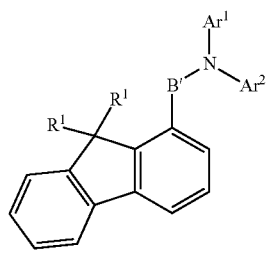

formula (14)

where the above definitions apply to the symbols and indices used.

Preference is furthermore given to a compound of the formulae (1) to (14) indicated above in which B' is selected from the groups of the formulae (15) to (36b), where these groups may also be substituted by one or more radicals $R^4$, which are independent of one another, and where $R^4$ is defined as indicated above:

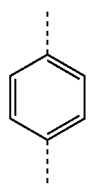

formula (15)

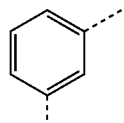

formula (16)

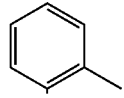

formula (17)

formula (18)

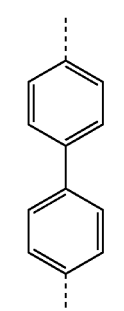

formula (19)

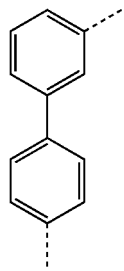

formula (20)

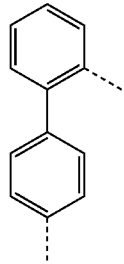

formula (21)

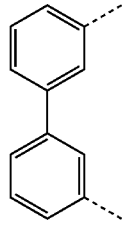

formula (22)

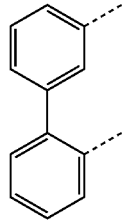

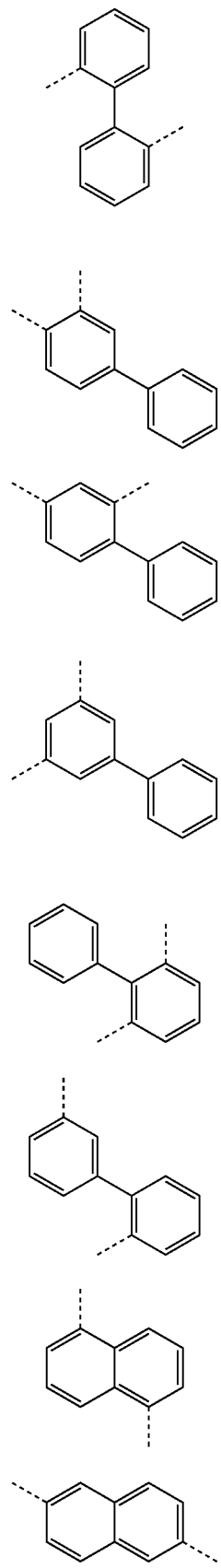
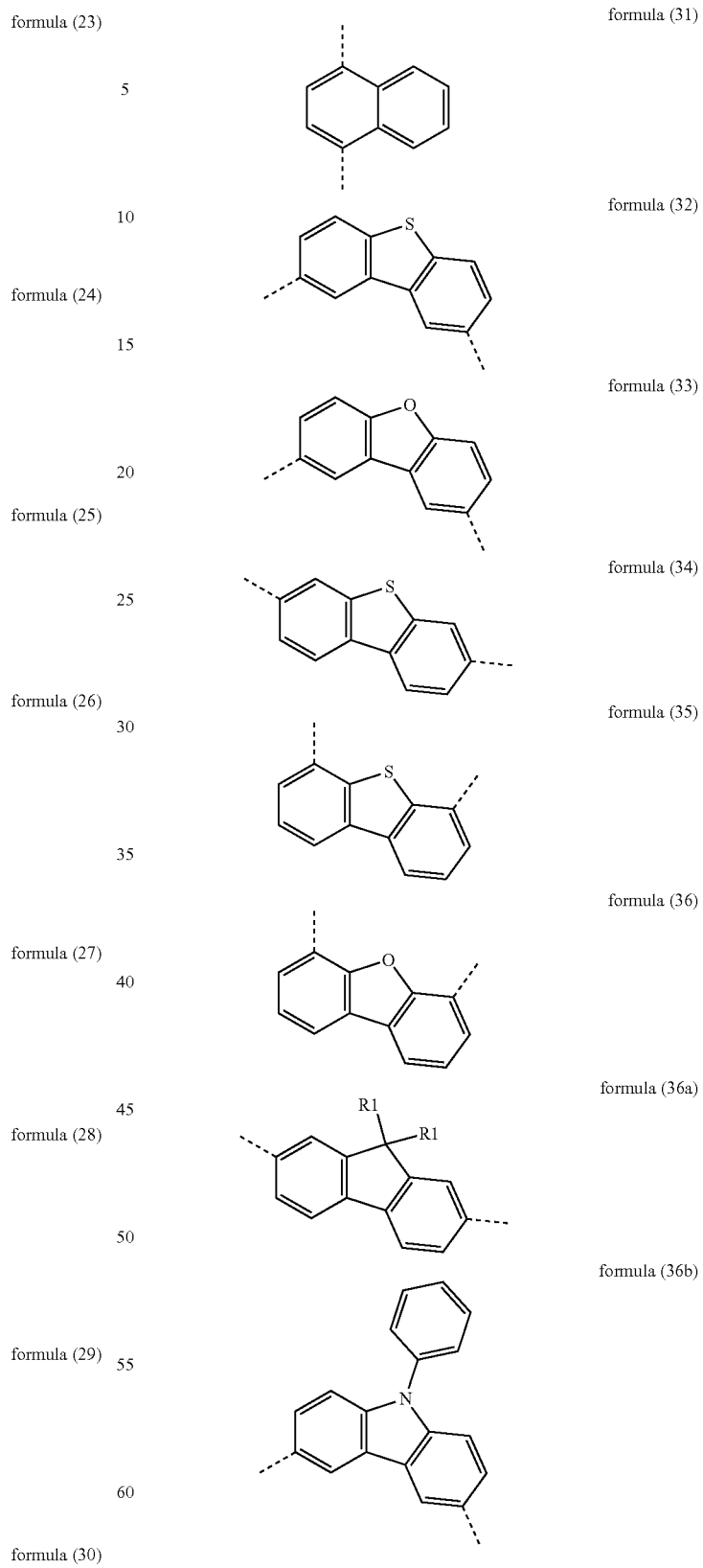
where the dashed lines denote the linking positions.
Particular preference is given to a compound of the formulae (1) to (14) indicated above in which B' is selected from the groups of the formulae (15) to (36b), where, in a very particularly preferred embodiment, these groups are unsubstituted.

Very particular preference is given to a compound of the formulae (1) to (14) indicated above in which B' conforms to the formulae (15) to (17), where these groups are preferably unsubstituted.

$Ar^1$ and $Ar^2$ are preferably selected from a phenyl, phenylpyridyl, phenylnaphthyl, biphenyl, terphenyl or quaterphenyl group, which may be substituted by one or more radicals $R^6$, which may be identical to or different from one another, where two of the aromatic or heteroaromatic rings in $Ar^1$ may additionally be bridged by a divalent group —O—, —S—, $C(R^6)_2$ or —Si$(R^6)_2$— or two of the aromatic or heteroaromatic rings in $Ar^2$ may additionally be bridged by a divalent group —O—, —S—, $C(R^6)_2$ or —Si$(R^6)_2$—, where it is preferred for no additional bridging to be present, and where an aromatic or heteroaromatic ring from $Ar^1$ may be bridged to an aromatic or heteroaromatic ring from $Ar^2$ by a divalent group —O—, —S—, —Si$(R^6)_2$—, —NR$^6$— or —C$(R^6)_2$—, where unbridged groups $Ar^1$ and $Ar^2$ are preferred and where at least one of the two groups $Ar^1$ and $Ar^2$ contains a fluorene group.

In a very preferred embodiment of the present invention, $Ar^1$ and $Ar^2$ are selected from the following groups of the formulae (37) to (122g), which may be substituted by one or more radicals $R^6$ and where at least one of the two groups $Ar^1$ and $Ar^2$ contains a fluorene group:

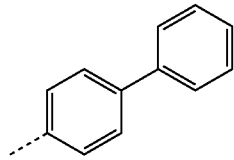

formula (37)

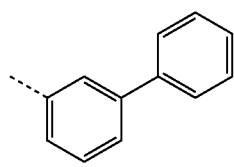

formula (38)

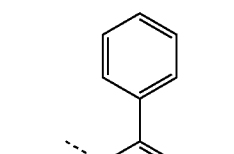

formula (39)

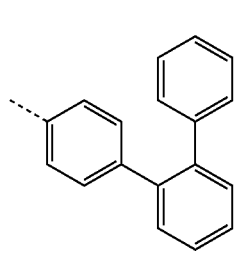

formula (40)

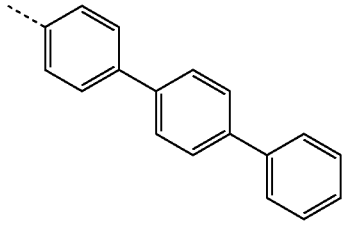

formula (41)

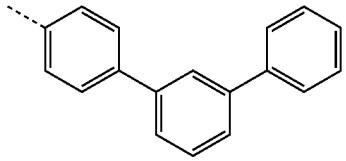

formula (42)

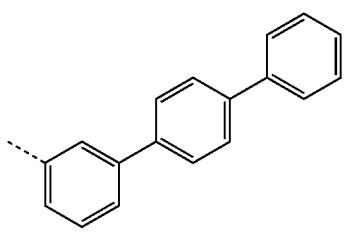

formula (43)

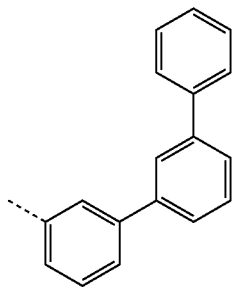

formula (44)

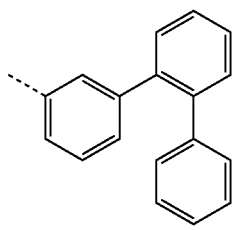

formula (45)

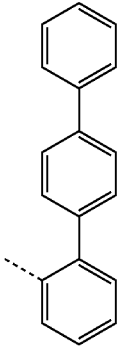

formula (46)

formula (47)
formula (48)
formula (49)
formula (50)
formula (51)
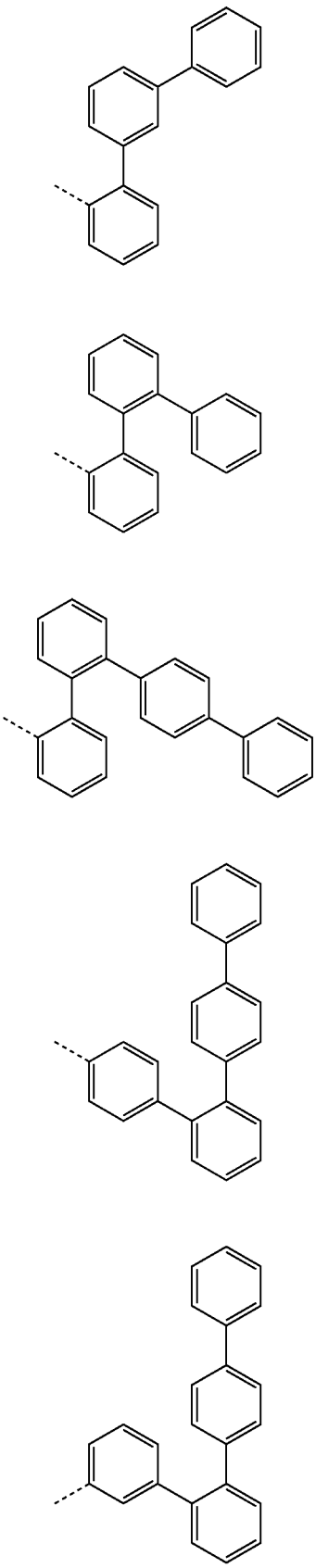
formula (52)
formula (53)
formula (54)
formula (55)
formula (56)
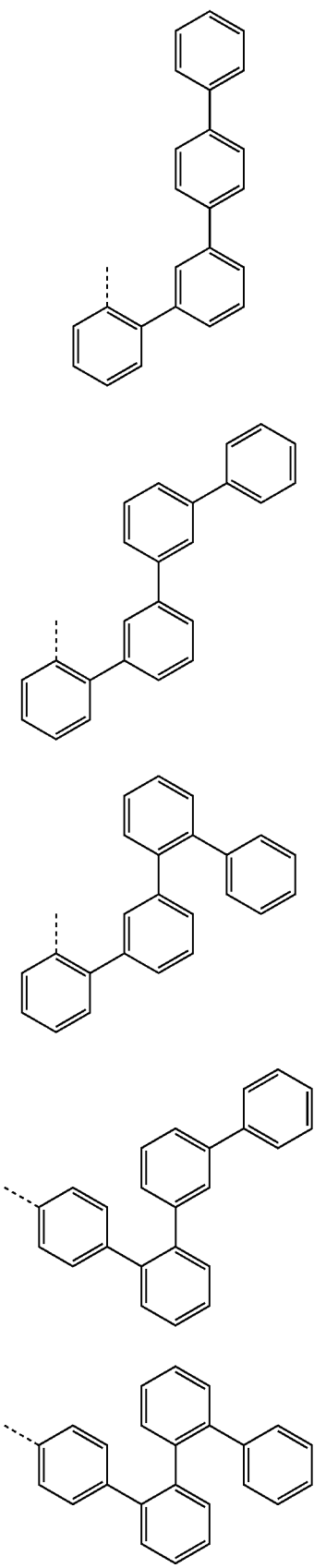

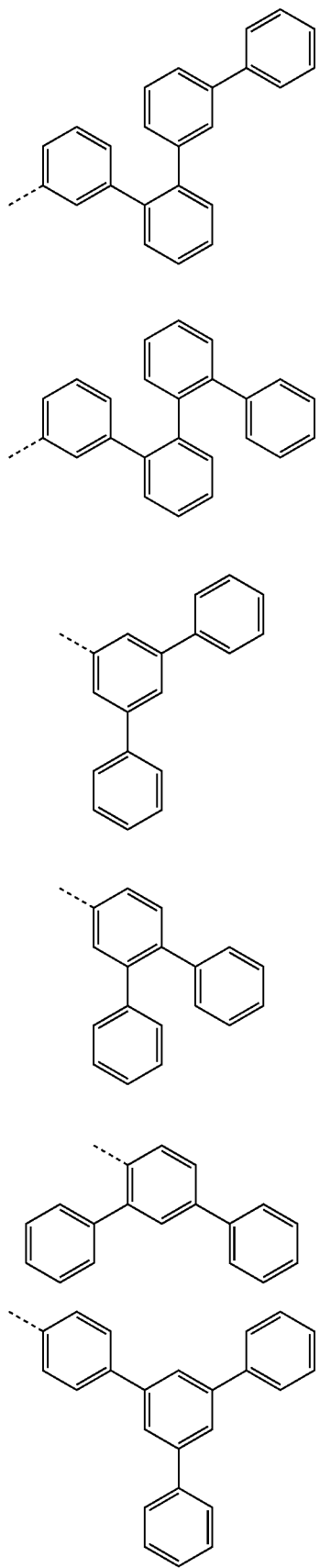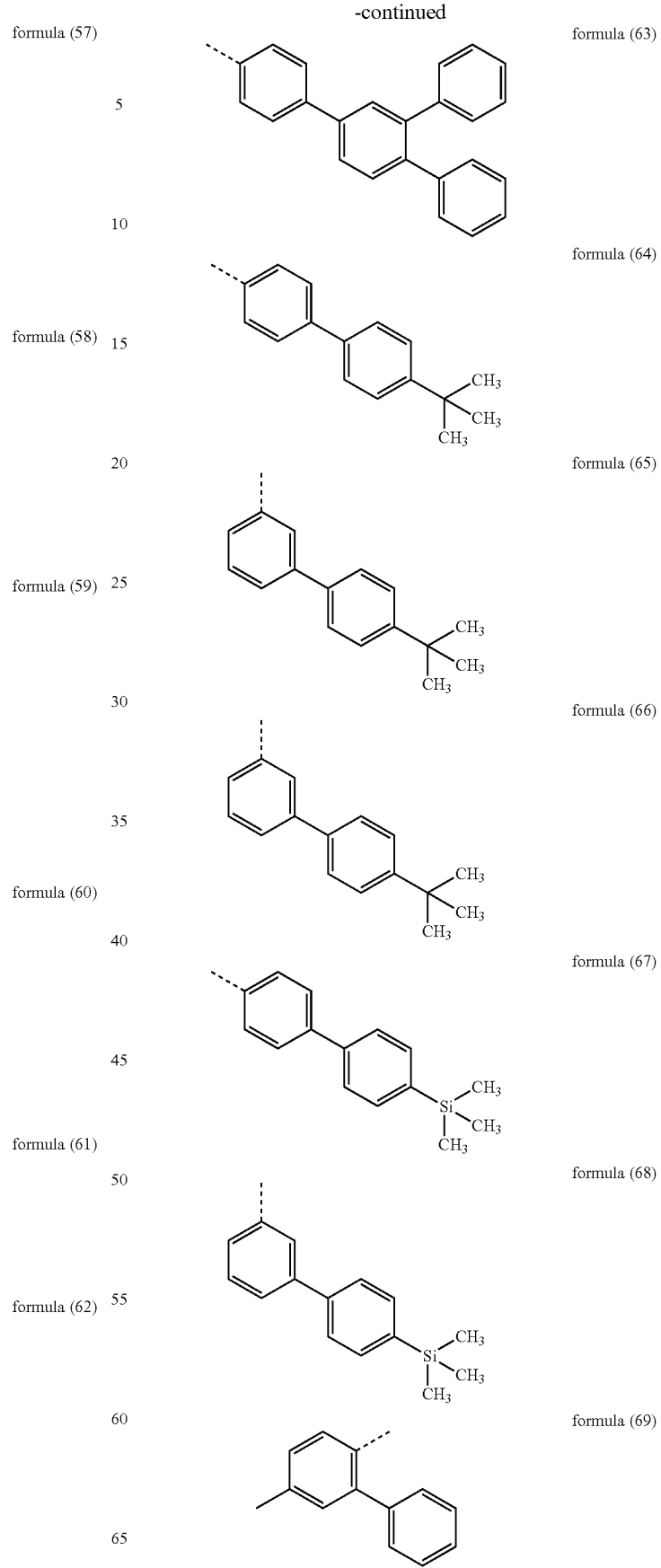

-continued
formula (70)
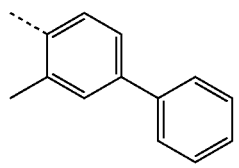
formula (71)
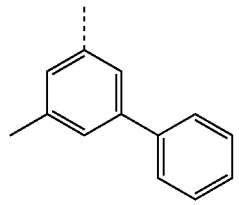
formula (72)
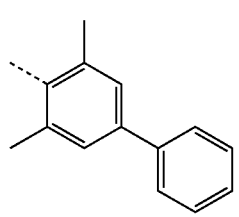
formula (73)
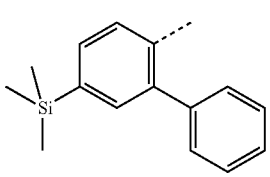
formula (74)
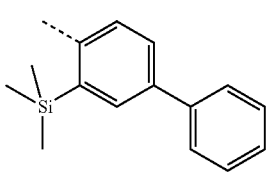
formula (75)
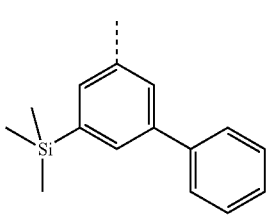
formula (76)
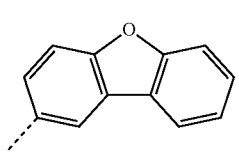
formula (77)
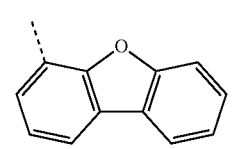
formula (78)
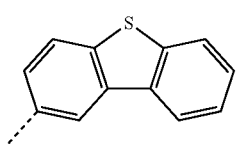
-continued
formula (79)
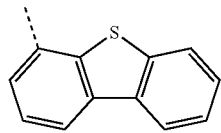
formula (80)
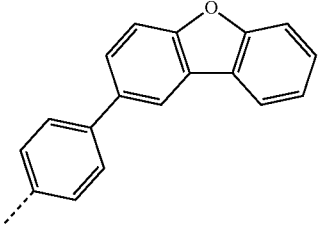
formula (81)
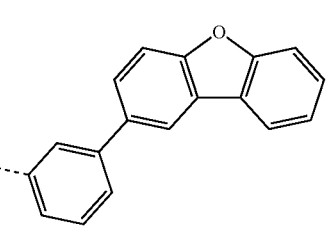
formula (82)
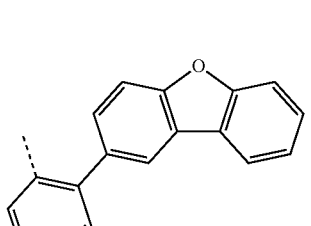
formula (83)
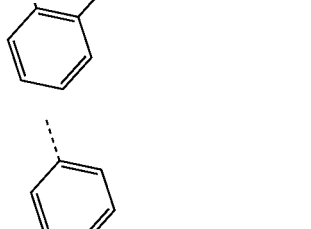
formula (84)
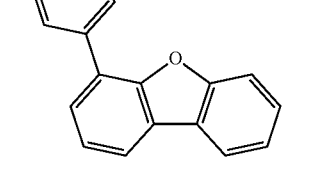
formula (85)
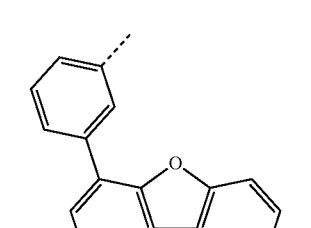

-continued
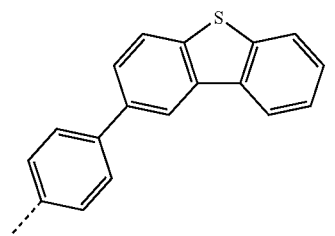
formula (86)
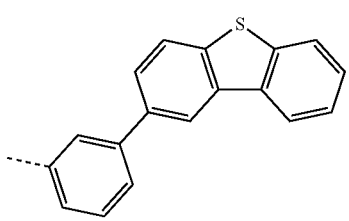
formula (87)
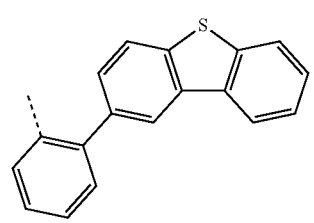
formula (88)
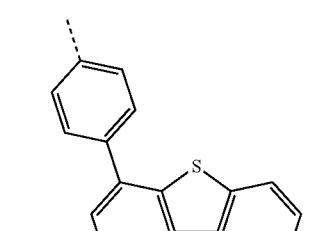
formula (89)
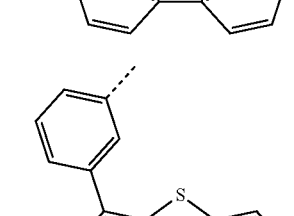
formula (90)
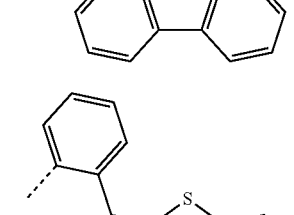
formula (91)
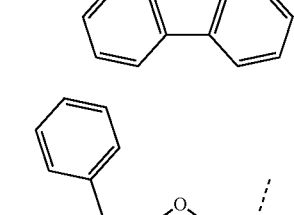
formula (92)
-continued
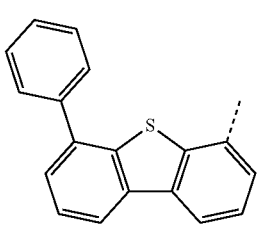
formula (93)
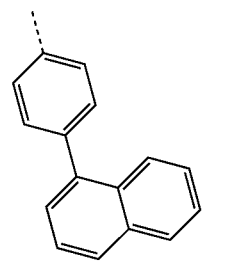
formula (94)
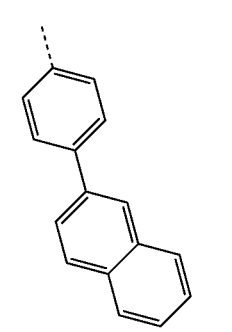
formula (95)
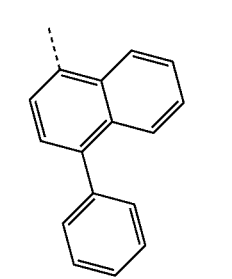
formula (96)
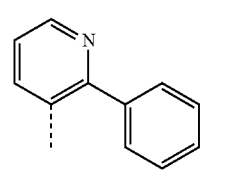
formula (97)
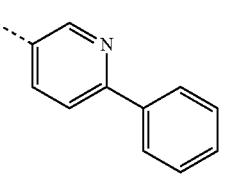
formula (98)
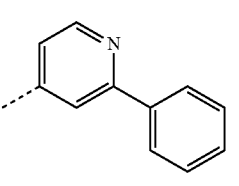
formula (99)

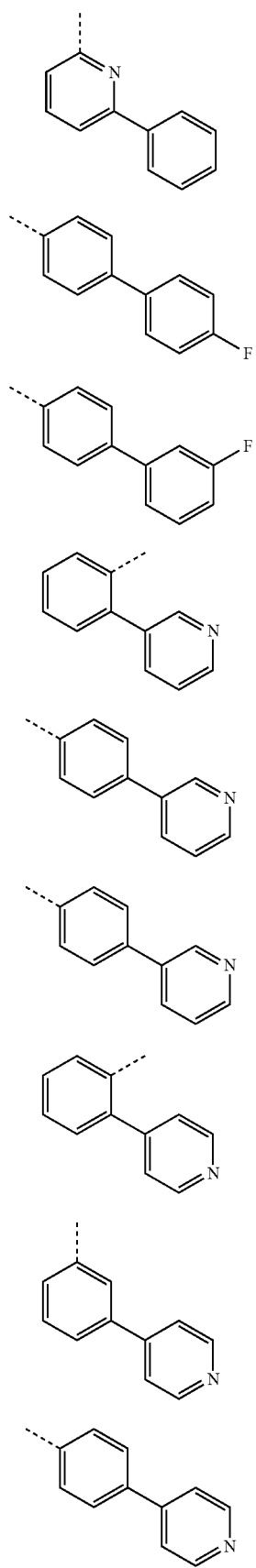
formula (100)
formula (101)
formula (102)
formula (103)
formula (104)
formula (105)
formula (106)
formula (107)
formula (108)
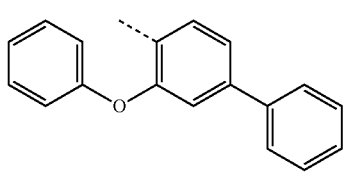
formula (109)
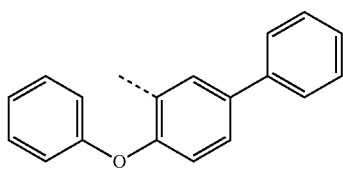
formula (110)
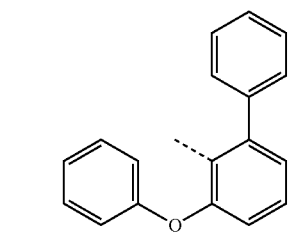
formula (111)
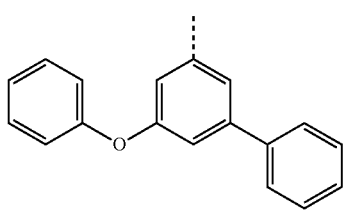
formula (112)
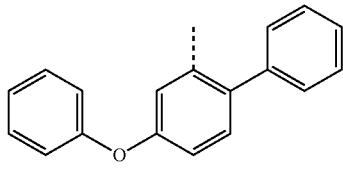
formula (113)
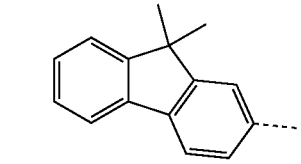
formula (114)
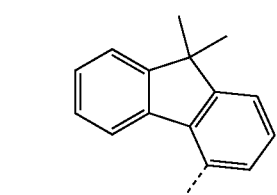
formula (115)
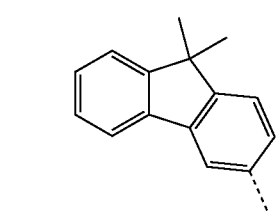
formula (116)

-continued formula (117)
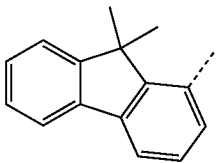

formula (118)
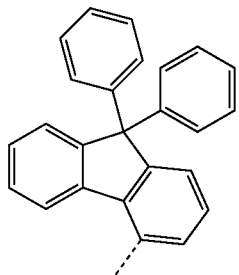

formula (119)
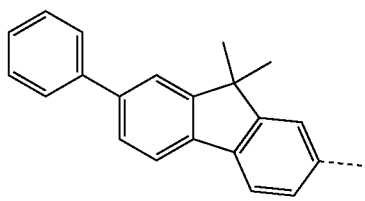

formula (120)
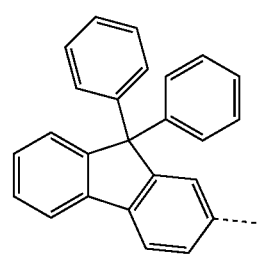

formula (121)
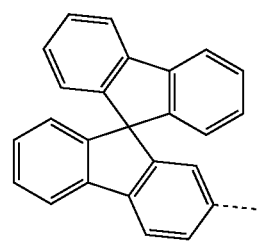

formula (122)
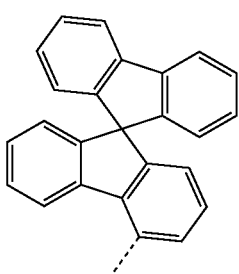

formula (122a)
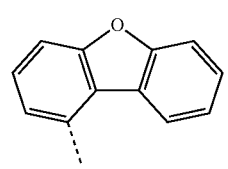

formula (122b)
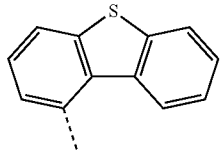

formula (122c)
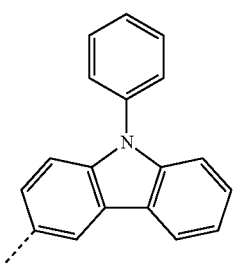

formula (122d)
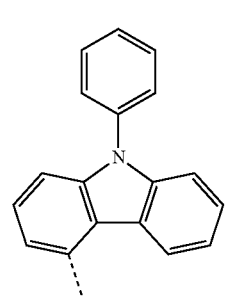

formula (122e)
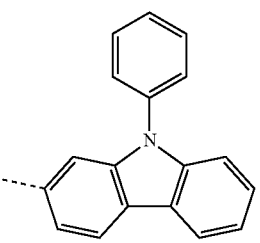

formula (122f)
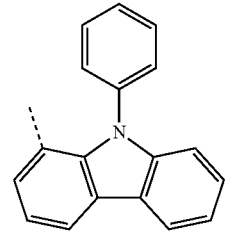

formula (122g)
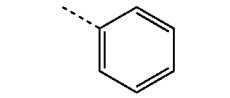

where the dashed line denotes the linking position to the nitrogen atom.

The at least one fluorene group of the groups $Ar^1$ and $Ar^2$ is, in a preferred embodiment of the present invention, bonded directly to the nitrogen atom of the groups $Z^a_1$, $Z^b_1$ or $Z^c_1$. It is very preferred for the at least one fluorene group of the groups $Ar^1$ and $Ar^2$ to be bonded to the nitrogen atom of the groups $Z^a_1$, $Z^b_1$ or $Z^c_1$ via its positions 1, 2, 3 and 4, where bonding via position 2 is very particularly preferred.

In a preferred embodiment, the present invention relates to a compound of the general formula (6), where the following applies to the symbols used:

$R^1$
is on each occurrence, identically or differently, preferably identically, a straight-chain alkyl group having 1 to 20 C atoms or a branched or cyclic alkyl group having 3 to 20 C atoms, where the above-mentioned groups may each be substituted by one or more radicals $R^4$, or an aromatic or heteroaromatic ring system having 6 to 30 aromatic ring atoms, which may in each case be substituted by one or more radicals $R^4$, where the two radicals $R^1$ may be linked to one another and may form a ring, so that a Spiro compound forms in position 9 of the fluorene, where spirobifluorenes are excluded;

$R^2$
is equal to H, a straight-chain alkyl group having 1 to 20 C atoms or a branched or cyclic alkyl group having 3 to 20 C atoms, where the groups may be substituted by one or more radicals $R^4$, an aromatic or heteroaromatic ring system having 6 to 30 aromatic ring atoms, which may be substituted by one or more radicals $R^4$;

$R^3$
is equal to H, D, F, Cl, Br, I, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^4$, or an aryloxy group having 5 to 60 aromatic ring atoms, which may be substituted by one or more radicals $R^4$, or an aralkyl group having 5 to 60 aromatic ring atoms, which may in each case be substituted by one or more radicals $R^4$, where two or more radicals $R^3$ may be linked to one another and may form a ring;

B'
is selected from the groups of the formulae (15) to (36), preferably (15) to (17), where these groups may also be substituted by one or more radicals $R^4$, which are independent of one another, and where $R^4$ is defined as indicated above;

$Ar^1$, $Ar^2$
are a phenyl, phenylpyridyl, phenylnaphthyl, biphenyl, terphenyl or quaterphenyl group, which may be substituted by one or more radicals $R^6$, which may be identical to or different from one another, where two of the aromatic or heteroaromatic rings in $Ar^1$ may additionally be bridged by a divalent group —O—, —S—, $C(R^6)_2$ or —$Si(R^6)_2$— or two of the aromatic or heteroaromatic rings in $Ar^2$ may additionally be bridged by a divalent group —O—, —S—, $C(R^6)_2$ or —$Si(R^6)_2$—, where it is preferred for no additional bridging to be present and where an aromatic or heteroaromatic ring from $Ar^1$ may be bridged to an aromatic or heteroaromatic ring from $Ar^2$ by a divalent group —O—, —S—, —$Si(R^6)_2$—, —$NR^6$— or —$C(R^6)_2$—, where unbridged groups $Ar^1$ and $Ar^2$ are preferred and where at least one of the two groups $Ar^1$ and $Ar^2$ contains a fluorene group.

In a very preferred embodiment, the present invention relates to a compound of the general formula (6), where the following applies to the symbols used:

$R^1$
is on each occurrence, identically or differently, preferably identically, a straight-chain alkyl group having 1 to 20 C atoms, where the said group may be substituted by one or more radicals $R^4$, or an aromatic or heteroaromatic ring system having 6 to 30 aromatic ring atoms, which may in each case be substituted by one or more radicals $R^4$, where the two radicals $R^1$ may be linked to one another and may form a ring, so that a spiro compound forms in position 9 of the fluorene, where spirobifluorenes are excluded;

$R^2$
is equal to H, a straight-chain alkyl group having 1 to 20 C atoms or a branched or cyclic alkyl group having 3 to 20 C atoms, where the groups may be substituted by one or more radicals $R^4$, an aromatic or heteroaromatic ring system having 6 to 30 aromatic ring atoms, which may be substituted by one or more radicals $R^4$;

$R^3$
is equal to H or an aromatic or heteroaromatic ring system having 6 to 30 aromatic ring atoms, which may in each case be substituted by one or more radicals $R^4$, where $R^3$ equal to H is especially preferred;

B'
is a phenylene group;

$Ar^1$, $Ar^2$
are a phenyl, biphenyl, terphenyl or quaterphenyl group, which may be substituted by one or more radicals $R^6$, which may be identical to or different from one another, where the rings in $Ar^1$ and $Ar^2$ are unbridged, $Ar^1$ and $Ar^2$ are especially preferably a biphenyl group, which may be substituted by one or more radicals $R^6$, which may be identical to or different from one another, and where at least one of the two groups $Ar^1$ and $Ar^2$ contains a fluorene group.

In a very particularly preferred embodiment, the present invention relates to a compound of the general formula (6), where the following applies to the symbols used:

$R^1$
is identical on each occurrence and is a straight-chain alkyl group having 1 to 5 C atoms, preferably a methyl group or ethyl group, where the said group may be substituted by one or more radicals $R^4$, or represents a phenyl, biphenyl or pyridyl group, which may in each case be substituted by one or more radicals $R^4$, where the two alkyl groups in accordance with $R^1$ may be linked to one another and may form a ring, so that a spiro compound forms in position 9 of the fluorene, where spirobifluorenes are excluded;

$R^2$
is equal to H, a straight-chain alkyl group having 1 to 20 C atoms or a branched or cyclic alkyl group having 3 to 20 C atoms, where the groups may be substituted by one or more radicals $R^4$, or an aromatic or heteroaromatic ring system having 6 to 30 aromatic ring atoms, which may be substituted by one or more radicals $R^4$;

$R^3$
is equal to H or an aromatic or heteroaromatic ring system having 6 to 30 aromatic ring atoms, which may in each case be substituted by one or more radicals $R^4$, where $R^3$ equals H is especially preferred;

B'
is a phenylene group;

$Ar^1$, $Ar^2$
are a phenyl, biphenyl, terphenyl or quaterphenyl group, which may be substituted by one or more radicals $R^6$, which may be identical to or different from one another, where the rings in $Ar^1$ and $Ar^2$ are unbridged, $Ar^1$ and $Ar^2$ are especially preferably a biphenyl group, which may be substituted by one or more radicals $R^6$, which may be identical to or different from one another, and where at least one of the two groups $Ar^1$ and $Ar^2$ contains a fluorene group.

Consequently, particular preference is given to a compound of the general formula (123)

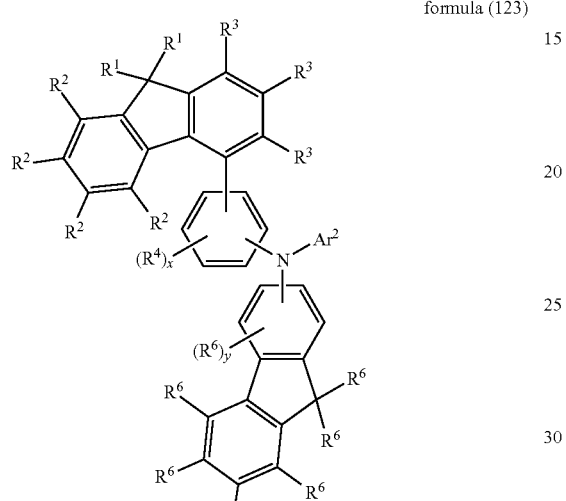

formula (123)

where x is equal to 0, 1, 2, 3 or 4 and where y is equal to 0, 1, 2 or 3.

Preference is furthermore also given to a compound of the general formula (124)

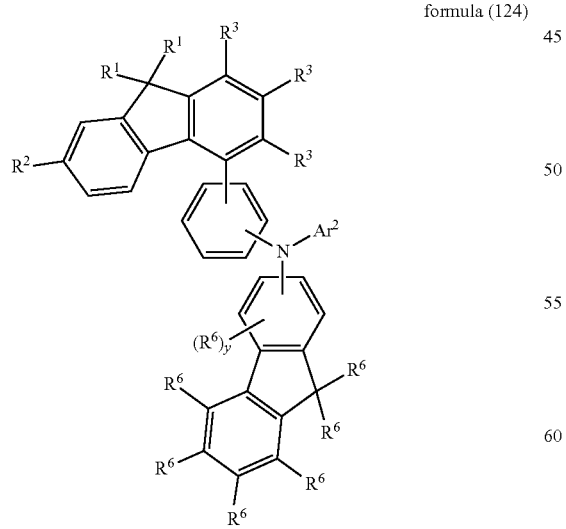

formula (124)

Greater preference is given to a compound of the general formula (125)

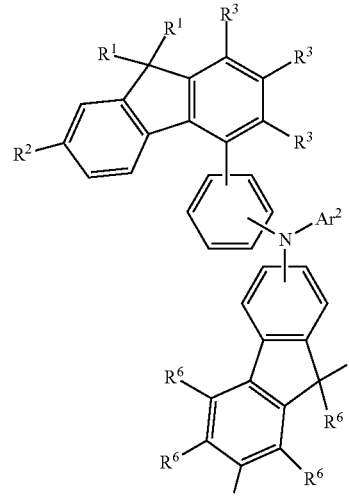

formula (125)

Still greater preference is given to a compound of the general formula (126)

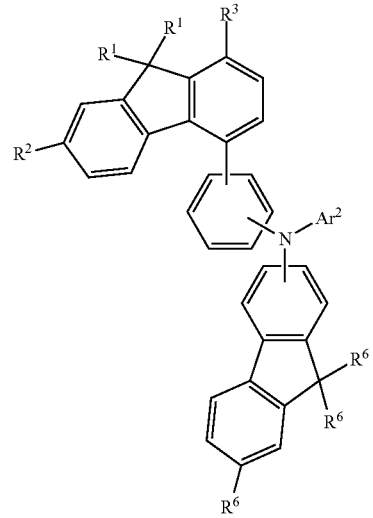

formula (126)

And still greater preference is given to a compound of the general formula (127)

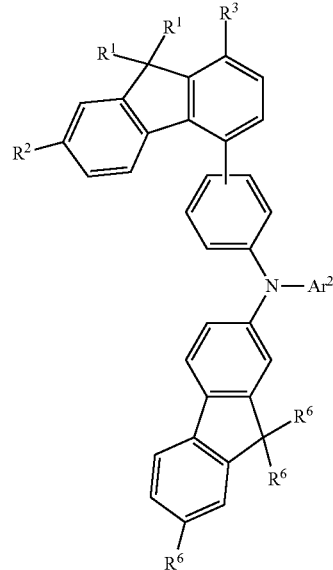

formula (127)

Finally, the compound of the following formula (128) represents an especially preferred embodiment of the present invention:

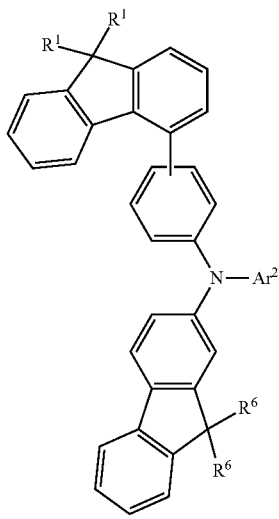

formula (128)

In a further preferred embodiment, the present invention relates to a compound of the general formula (8), where the following applies to the symbols used:

$R^1$
is on each occurrence, identically or differently, preferably identically, a straight-chain alkyl group having 1 to 20 C atoms or a branched or cyclic alkyl group having 3 to 20 C atoms, where the above-mentioned groups may each be substituted by one or more radicals $R^4$, or an aromatic or heteroaromatic ring system having 6 to 30 aromatic ring atoms, which may in each case be substituted by one or more radicals $R^4$, where the two radicals $R^1$ may be linked to one another and may form a ring, so that a spiro compound forms in position 9 of the fluorene, where spirobifluorenes are excluded;

$R^2$
is equal to H, a straight-chain alkyl group having 1 to 20 C atoms or a branched or cyclic alkyl group having 3 to 20 C atoms, where the groups may be substituted by one or more radicals $R^4$, or an aromatic or heteroaromatic ring system having 6 to 30 aromatic ring atoms, which may be substituted by one or more radicals $R^4$;

$R^3$
is equal to H, D, F, Cl, Br, I, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^4$, or an aryloxy group having 5 to 60 aromatic ring atoms, which may be substituted by one or more radicals $R^4$, or an aralkyl group having 5 to 60 aromatic ring atoms, which may in each case be substituted by one or more radicals $R^4$, where two or more radicals $R^3$ may be linked to one another and may form a ring;

B'
is selected from the groups of the formulae (15) to (36), preferably (15) to (17), where these groups may also be substituted by one or more radicals $R^4$, which are independent of one another, and where $R^4$ is defined as indicated above;

$Ar^1$, $Ar^2$
are a phenyl, phenylpyridyl, phenylnaphthyl, biphenyl, terphenyl or quaterphenyl group, which may be substituted by one or more radicals $R^6$, which may be identical to or different from one another, where two or heteroaromatic rings in $Ar^1$ may additionally be bridged by a divalent group —O—, —S—, $C(R^6)_2$ or $—Si(R^6)_2—$ or two aromatic or heteroaromatic rings in $Ar^2$ may additionally be bridged by a divalent group —O—, —S—, $C(R^6)_2$ or $—Si(R^6)_2—$, where it is preferred for no additional bridging to be present and where an aromatic or heteroaromatic ring from $Ar^1$ may be bridged to an aromatic or heteroaromatic ring from $Ar^2$ by a divalent group —O—, —S—, $—Si(R^6)_2—$, $—NR^6—$ or $—C(R^6)_2—$, where unbridged groups $Ar^1$ and $Ar^2$ are preferred and where at least one of the two groups $Ar^1$ and $Ar^2$ contains a fluorene group.

In a very preferred embodiment, the present invention relates to a compound of the general formula (8), where the following applies to the symbols used:

$R^1$
is on each occurrence, identically or differently, preferably identically, a straight-chain alkyl group having 1 to 20 C atoms, where the said group may be substituted by one or more radicals $R^4$, or an aromatic or heteroaromatic ring system having 6 to 30 aromatic ring atoms, which may in each case be substituted by one or more radicals $R^4$, where the two radicals $R^1$ may be linked to one another and may form a ring, so that a spiro compound forms in position 9 of the fluorene, where spirobifluorenes are excluded;

$R^2$
is equal to H, a straight-chain alkyl group having 1 to 20 C atoms or a branched or cyclic alkyl group having 3 to 20 C atoms, where the groups may be substituted by one or more radicals $R^4$, an aromatic or heteroaromatic ring system having 6 to 30 aromatic ring atoms, which may be substituted by one or more radicals $R^4$;

$R^3$
is equal to H or an aromatic or heteroaromatic ring system having 6 to 30 aromatic ring atoms, which may in each case be substituted by one or more radicals $R^4$, where $R^3$ equal to H is especially preferred;

B'
is a phenylene group;

$Ar^1$, $Ar^2$
are a phenyl, biphenyl, terphenyl or quaterphenyl group, which may be substituted by one or more radicals $R^6$, which may be identical to or different from one another, where the rings in $Ar^1$ and $Ar^2$ are not additionally bridged, $Ar^1$ and $Ar^2$ are especially preferably a biphenyl group, which may be substituted by one or more radicals $R^6$, which may be identical to or different from one another, and where at least one of the two groups $Ar^1$ and $Ar^2$ contains a fluorene group.

In a very particularly preferred embodiment, the present invention relates to a compound of the general formula (8), where the following applies to the symbols used:

$R^1$
is identical on each occurrence and is a straight-chain alkyl group having 1 to 5 C atoms, preferably a methyl group or ethyl group, where the said group may be substituted by one or more radicals $R^4$, or represents a phenyl, biphenyl or pyridyl group, which may in each case be substituted by one or more radicals $R^4$, where the two alkyl groups in accordance with $R^1$ may be linked to one another and may form a ring, so that a spiro compound forms in position 9 of the fluorene, where spirobifluorenes are excluded;

$R^2$
is equal to H, a straight-chain alkyl group having 1 to 20 C atoms or a branched or cyclic alkyl group having 3 to 20 C atoms, where the groups may be substituted by one or more radicals $R^4$, or an aromatic or heteroaromatic ring system having 6 to 30 aromatic ring atoms, which may be substituted by one or more radicals $R^4$;

$R^3$
is equal to H or an aromatic or heteroaromatic ring system having 6 to 30 aromatic ring atoms, which may in each case be substituted by one or more radicals $R^4$, where $R^3$ equal to H is especially preferred;

B'
is a phenylene group;

$Ar^1$, $Ar^2$
are a phenyl, biphenyl, terphenyl or quaterphenyl group, which may be substituted by one or more radicals $R^6$, which may be identical to or different from one another, where the rings in $Ar^1$ and $Ar^2$ are not additionally bridged, $Ar^1$ and $Ar^2$ are especially preferably a biphenyl group, which may be substituted by one or more radicals $R^6$, which may be identical to or different from one another, and where at least one of the two groups $Ar^1$ and $Ar^2$ contains a fluorene group.

In an especially preferred embodiment, the present invention relates to compounds of the general formula (1), characterised in that they are monoamine compounds.

Consequently, particular preference is given to a compound of the general formula (129)

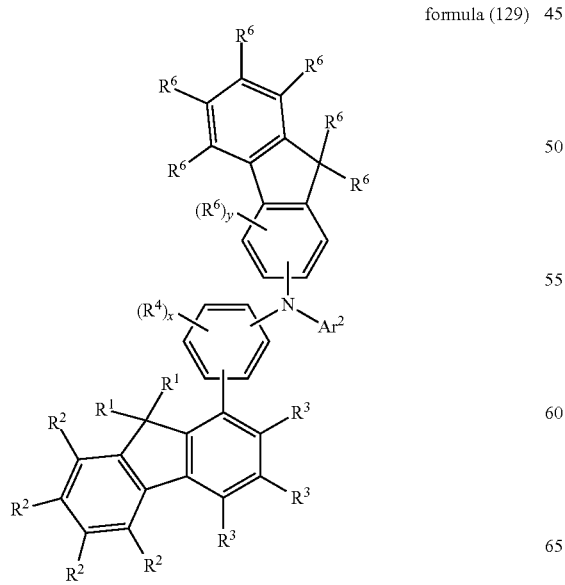

formula (129)

where x is equal to 0, 1, 2, 3 or 4 and where y is equal to 0, 1, 2 or 3.

Preference is furthermore also given to a compound of the general formula (130)

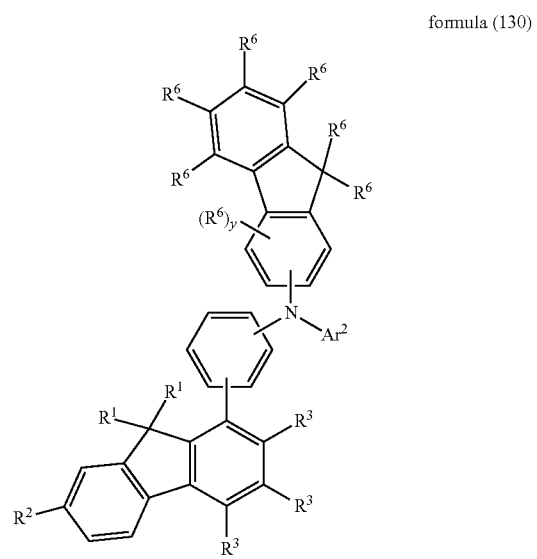

formula (130)

Greater preference is given to a compound of the general formula (131)

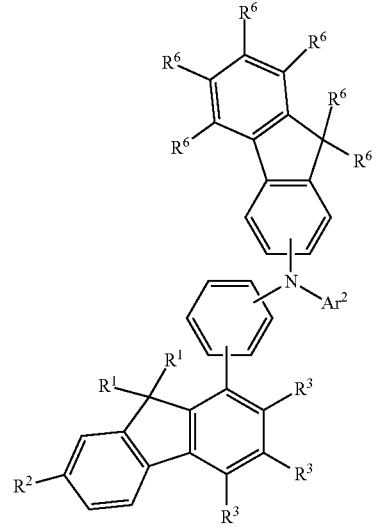

formula (131)

Still greater preference is given to a compound of the general formula (132)

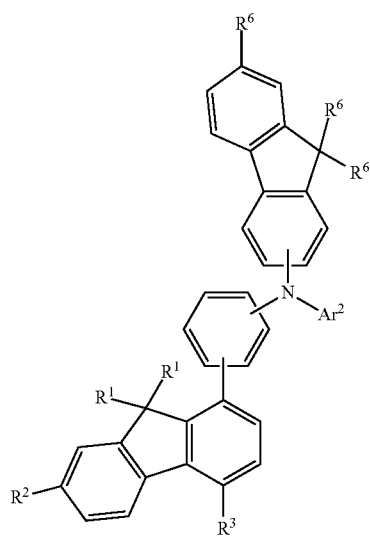

formula (132)

And still greater preference is given to a compound of the general formula (133)

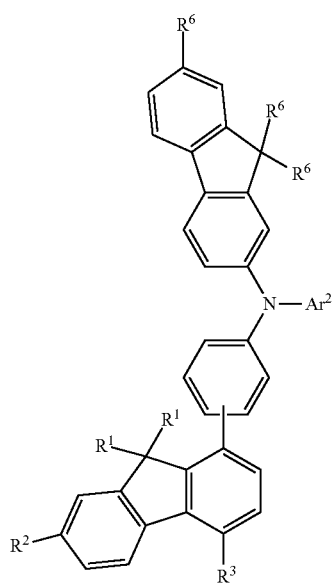

formula (133)

Finally, the compound of the following formula (134) represents an especially preferred embodiment of the present invention:

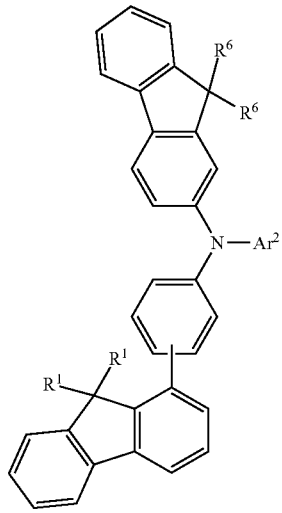

formula (134)

The following reaction scheme shows a preferred synthetic route for the preparation of the compounds of the formula (1) according to the invention. For the synthesis of the compounds according to the invention, the fluorene compound A is firstly converted into a compound B by methods familiar to the person skilled in the art (such as, for example, boronation and Suzuki coupling) and reacted further by a Buchwald coupling to an amine C of the formula $Ar^1$—NH—$Ar^2$ to give the compound according to the invention,

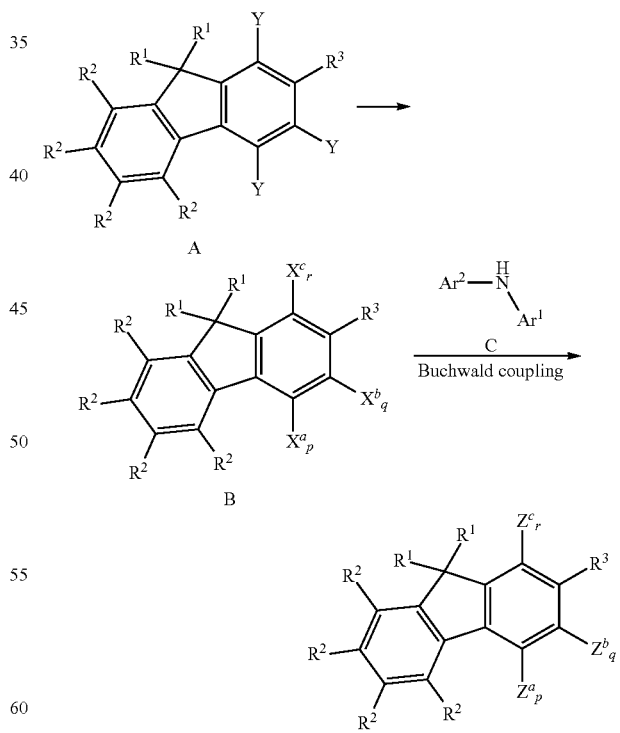

where the above definitions apply to the symbols and indices used and where
Y is a leaving group, preferably halogen;
$X^a{}_0$, $X^b{}_0$, $X^c{}_0$ are, identically or differently on each occurrence, equal to $R^3$ and $X^a{}_1$, $X^b{}_1$, $X^c{}_1$ are equal to —B'—Y, where Y is a leaving group, for example halogen.

Another preferred synthetic route for the preparation of the compounds according to the invention is depicted in the following reaction scheme. The synthetic route comprises two coupling reactions: firstly, the fluorene compound B is reacted with an amine D of the formula $Ar^1$—$NH_2$ in a first Buchwald coupling. Finally, a second Buchwald coupling is carried out to a compound F, for example with a bromoaryl compound,

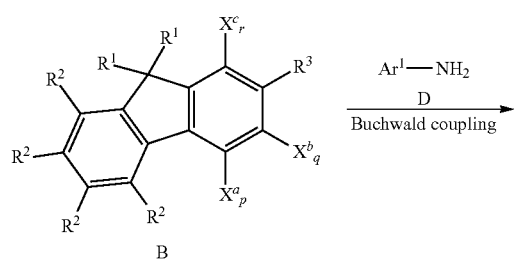

B

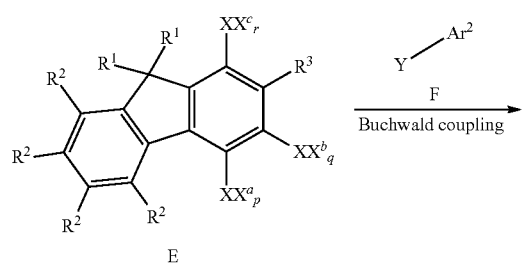

E

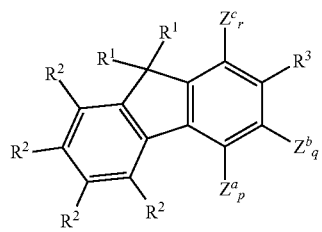

where Y is again a leaving group, preferably halogen; and where
$XX^a{}_0$, $XX^b{}_0$, $XX^c{}_0$ are, identically or differently on each occurrence, equal to $R^3$ and
$XX^a{}_1$, $XX^b{}_1$, $XX^c{}_1$ are equal to —B'—NH—$Ar^1$.

Another preferred synthetic route for the preparation of the compounds according to the invention is depicted in the following reaction scheme. To this end, the fluorene compound A is converted into the compound according to the invention by one of the C—C coupling methods familiar to the person skilled in the art (such as, for example, Suzuki coupling)

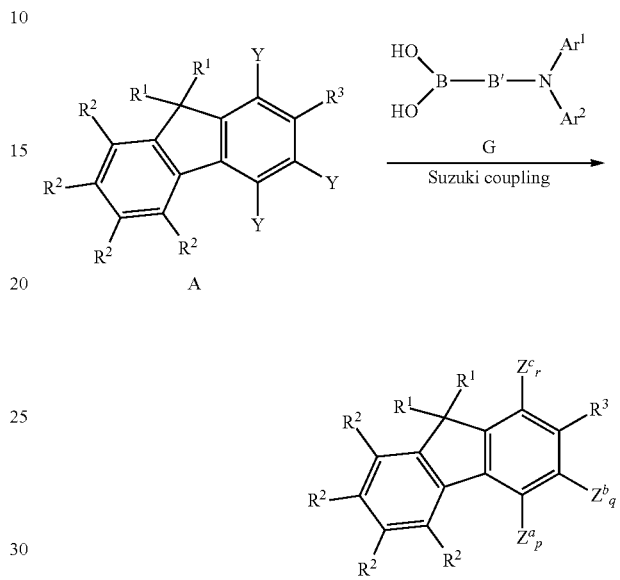

The following scheme shows a further preferred synthetic route for the preparation of the compounds according to the invention. To this end, benzochromenones H serve as starting point. The addition of an organometallic reagent, for example a Grignard or organolithium reagent, and subsequent acid-catalysed cyclisation of the intermediate alcoholate leads to the corresponding 4-hydroxyfluorene I. The hydroxyl group is subsequently converted into a leaving group Y or —B'—Y (=$X^a{}_1$), for example into a triflate (TfO) or a halide (preferably Br or Cl), and further into the compound according to the invention by a method familiar to the person skilled in the art (C—C coupling, such as Suzuki, Negishi, Yamamoto, Grignard-Cross, Stille, Heck coupling, etc.; C—N coupling, such as Buchwald coupling), where a Buchwald coupling or a Suzuki coupling is preferred. In the case of $X^a{}_1$, only Y is of course the leaving group.

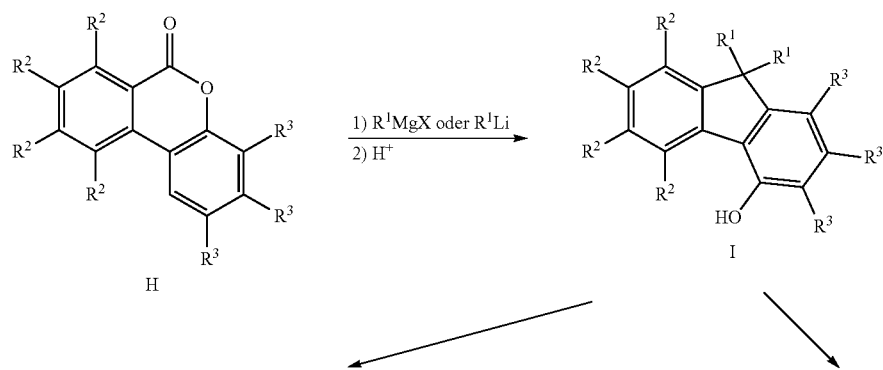

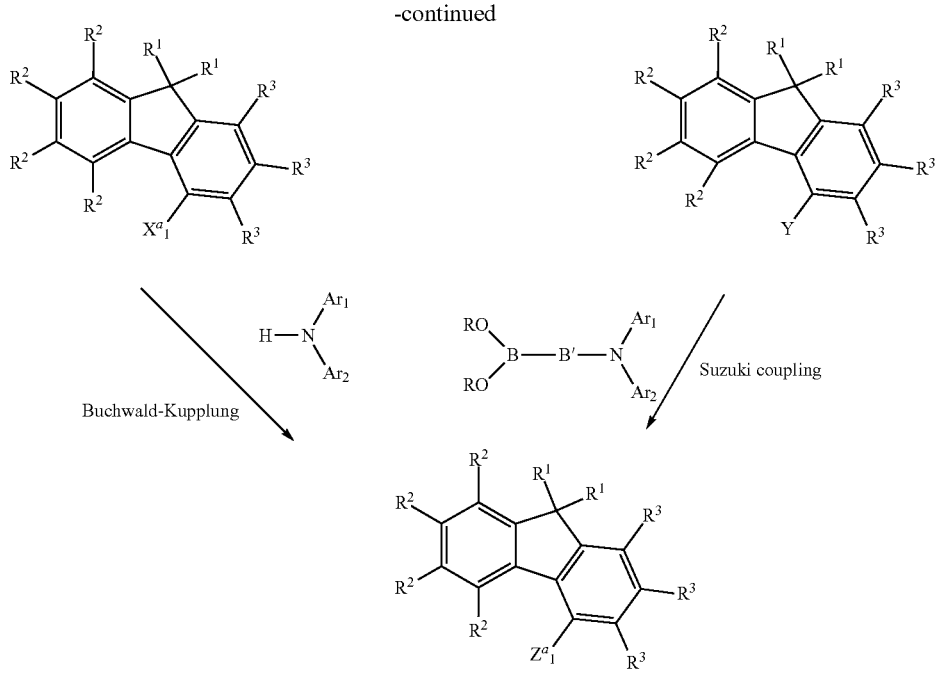

where the indices used are defined as indicated above and B stands for a boron atom.

This enables the preparation of fluorenes which have the amine in the preferred position 4.

Fluorenes according to the invention which have the amine in position 1 of the fluorene can be prepared entirely analogously thereto.

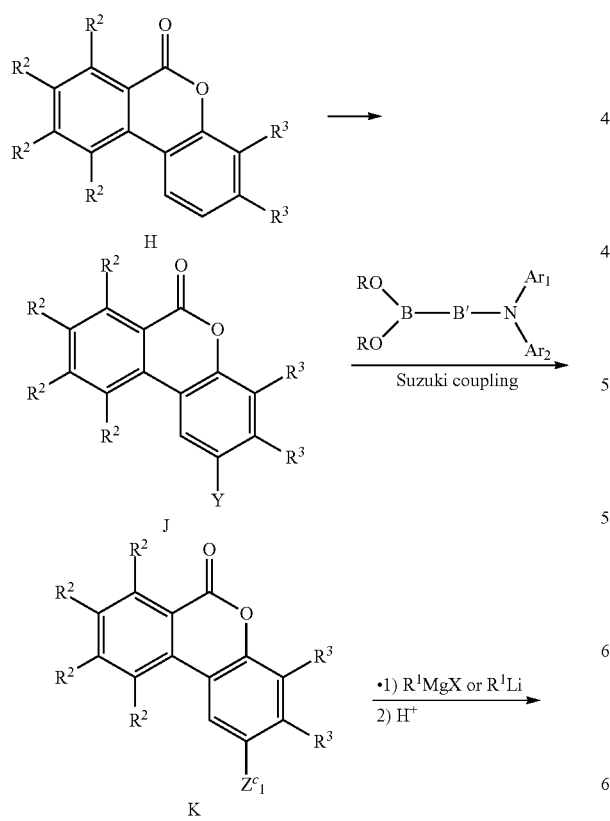

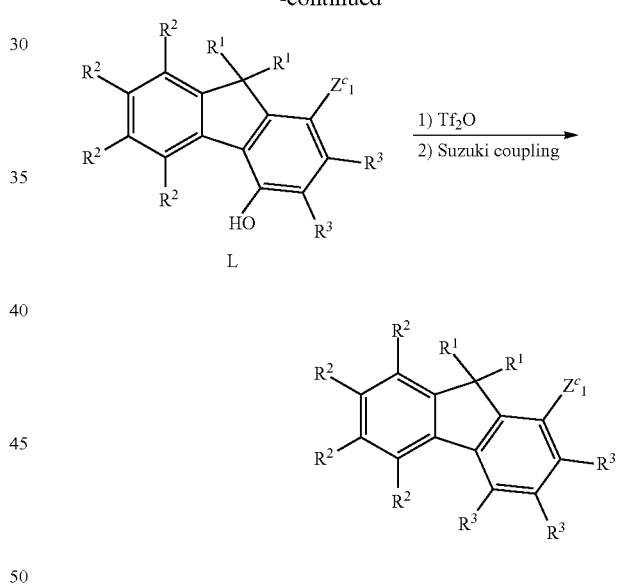

The boronic acid esters containing the groups R employed for the Suzuki coupling are well known to the person skilled in the art.

Synthetic routes for the starting compounds and intermediate compounds A, B, C, D, E, F, G, H, I, J, K and L which are employed in the synthesis of the compounds according to the invention are familiar to the person skilled in the art. Furthermore, some explicit synthesis processes are described in detail in the working examples.

Preferred coupling reactions for the preparation of the compounds of the general formula (1) are Buchwald couplings and Suzuki couplings.

Preferred compounds according to the invention are shown by way of example in the following table:

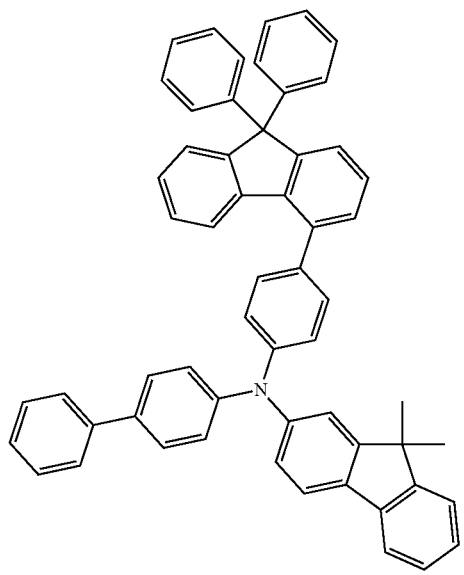 [SMILES: CC1(C)c2ccccc2-c2ccc(N(c3ccc(-c4ccccc4)cc3)c3ccc(-c4cccc5c4-c4ccccc4C5(c4ccccc4)c4ccccc4)cc3)cc21]
formula (A-1)
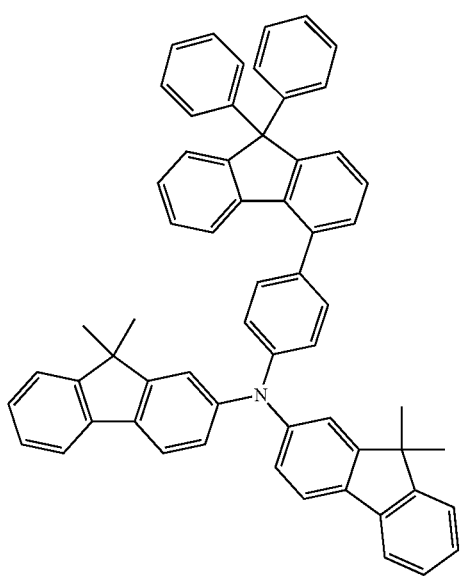 [SMILES: CC1(C)c2ccccc2-c2ccc(N(c3ccc(-c4cccc5c4-c4ccccc4C5(c4ccccc4)c4ccccc4)cc3)c3ccc4c(c3)C(C)(C)c3ccccc3-4)cc21]
formula (A-2)
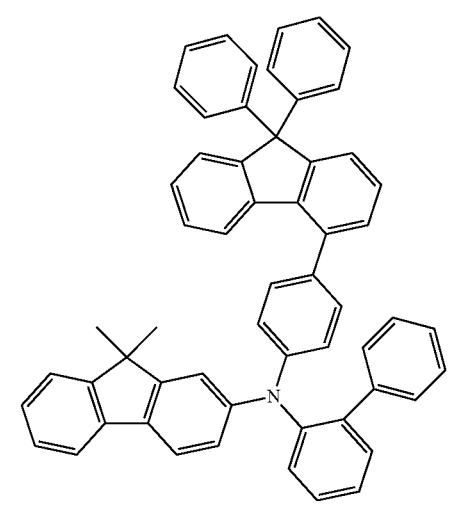 [SMILES: CC1(C)c2ccccc2-c2ccc(N(c3ccc(-c4cccc5c4-c4ccccc4C5(c4ccccc4)c4ccccc4)cc3)c3ccccc3-c3ccccc3)cc21]
formula (A-3)

-continued
formula (A-4)
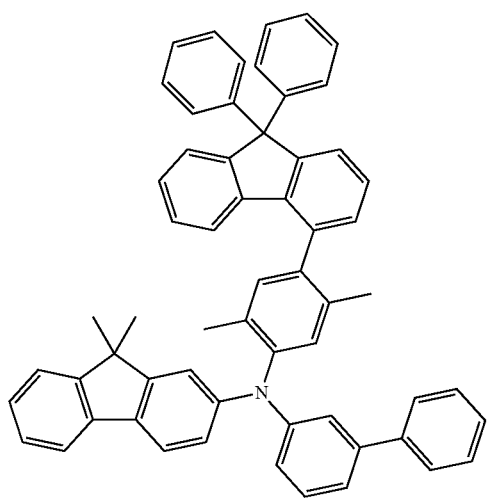 [SMILES: Cc1cc(N(c2cccc(-c3ccccc3)c2)c2ccc3c(c2)C(C)(C)c2ccccc2-3)c(C)cc1-c1cccc2c1-c1ccccc1C2(c1ccccc1)c1ccccc1]
formula (A-5)
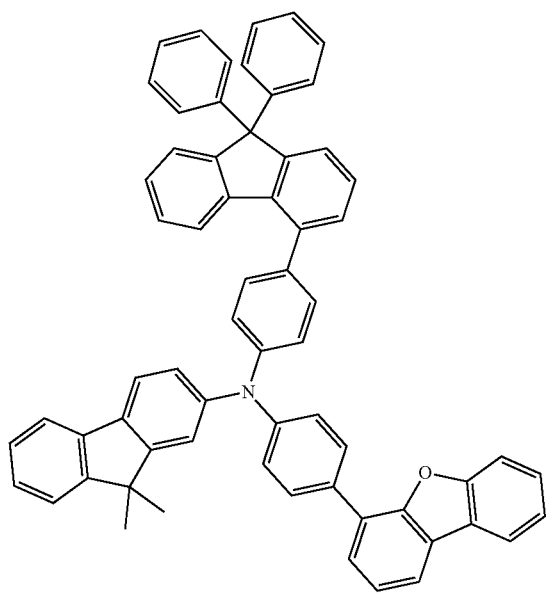 [SMILES: CC1(C)c2ccccc2-c2ccc(N(c3ccc(-c4cccc5c4-c4ccccc4C5(c4ccccc4)c4ccccc4)cc3)c3ccc(-c4cccc5c4oc4ccccc45)cc3)cc21]
formula (A-6)
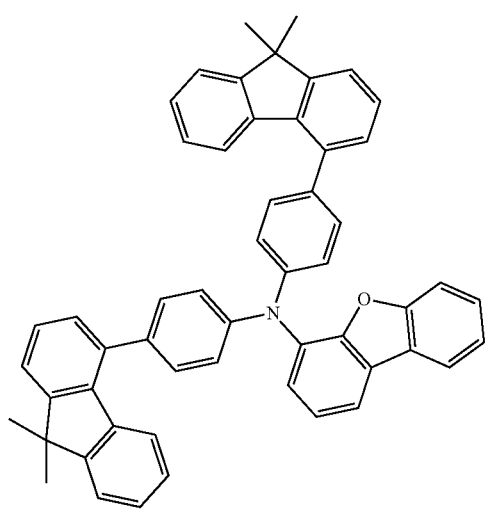 [SMILES: CC1(C)c2ccccc2-c2c(-c3ccc(N(c4ccc(-c5cccc6c5-c5ccccc5C6(C)C)cc4)c4cccc5c4oc4ccccc45)cc3)cccc21]

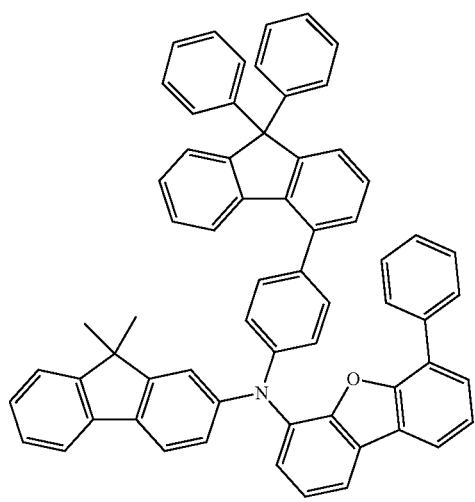 [SMILES: CC1(C)c2ccccc2-c2ccc(N(c3ccc(-c4cccc5c4-c4ccccc4C5(c4ccccc4)c4ccccc4)cc3)c3cccc4c3oc3c(-c5ccccc5)cccc34)cc21]
formula (A-7)
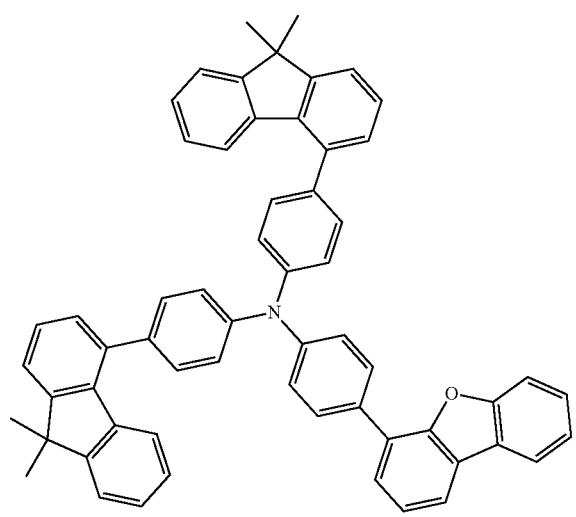 [SMILES: CC1(C)c2ccccc2-c2c(-c3ccc(N(c4ccc(-c5cccc6c5-c5ccccc5C6(C)C)cc4)c4ccc(-c5cccc6c5oc5ccccc56)cc4)cc3)cccc21]
formula (A-8)
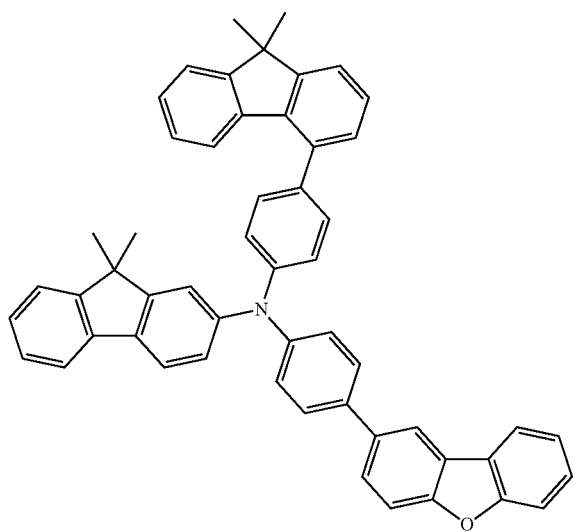
formula (A-9)

-continued
formula (A-10)
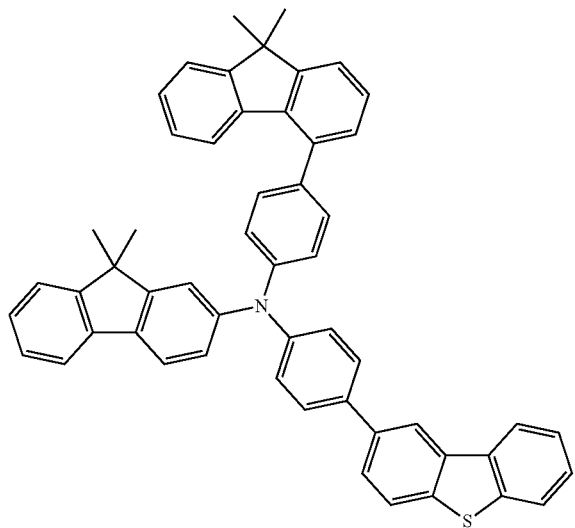 [SMILES: CC1(C)c2ccccc2-c2ccc(N(c3ccc(-c4ccc5oc6ccccc6c5c4)cc3)c3ccc(-c4cccc5c4-c4ccccc4C5(C)C)cc3)cc21]
formula (A-11)
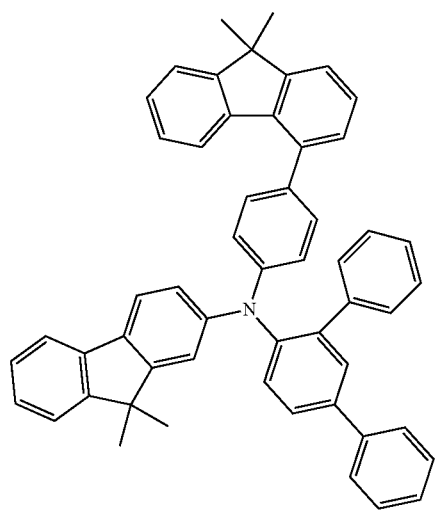 [SMILES: CC1(C)c2ccccc2-c2ccc(N(c3ccc(-c4cccc5c4-c4ccccc4C5(C)C)cc3)c3ccc(-c4ccccc4)cc3-c3ccccc3)cc21]
formula (A-12)
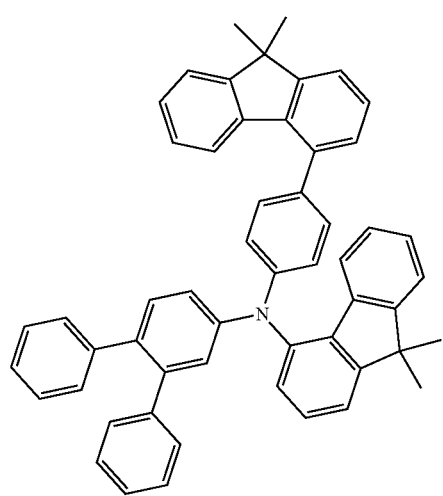 [SMILES: CC1(C)c2ccccc2-c2c(-c3ccc(N(c4ccc(-c5ccccc5)c(-c5ccccc5)c4)c4cccc5c4-c4ccccc4C5(C)C)cc3)cccc21]

formula (A-13)
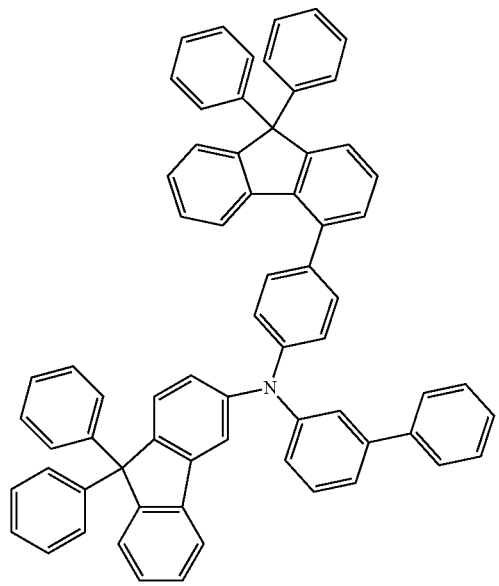 [SMILES: c1ccc(-c2cccc(N(c3ccc(-c4cccc5c4-c4ccccc4C5(c4ccccc4)c4ccccc4)cc3)c3ccc4c(c3)-c3ccccc3C4(c3ccccc3)c3ccccc3)c2)cc1]
formula (A-14)
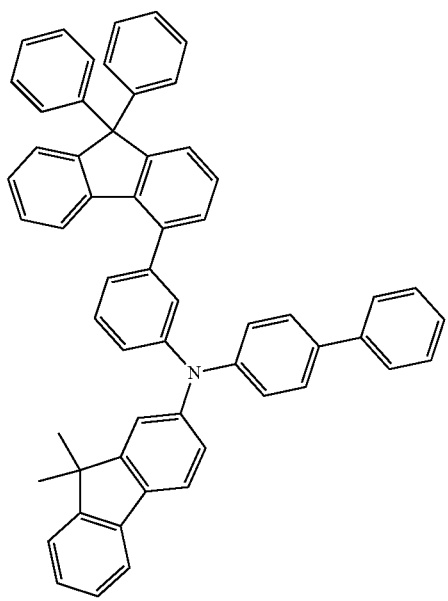 [SMILES: CC1(C)c2ccccc2-c2ccc(N(c3ccc(-c4ccccc4)cc3)c3cccc(-c4cccc5c4-c4ccccc4C5(c4ccccc4)c4ccccc4)c3)cc21]

formula (A-15)
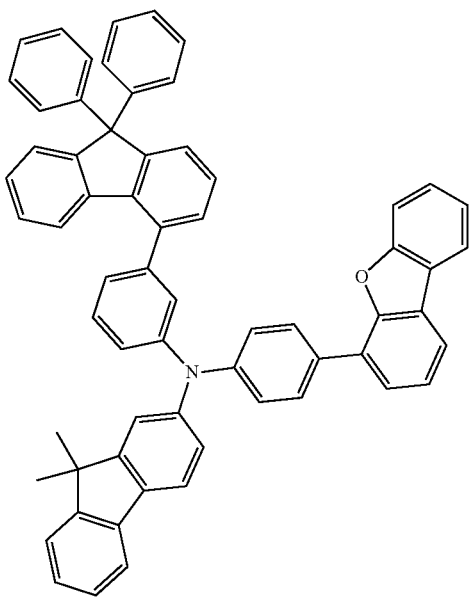 [SMILES: CC1(C)c2ccccc2-c2ccc(N(c3ccc(-c4cccc5c4oc4ccccc45)cc3)c3cccc(-c4cccc5c4-c4ccccc4C5(c4ccccc4)c4ccccc4)c3)cc21]
formula (A-16)
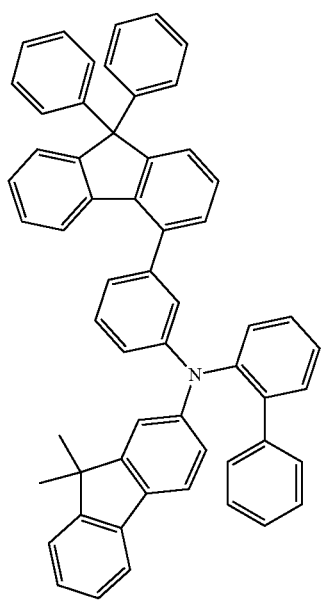 [SMILES: CC1(C)c2ccccc2-c2ccc(N(c3cccc(-c4cccc5c4-c4ccccc4C5(c4ccccc4)c4ccccc4)c3)c3ccccc3-c3ccccc3)cc21]

formula (A-17)
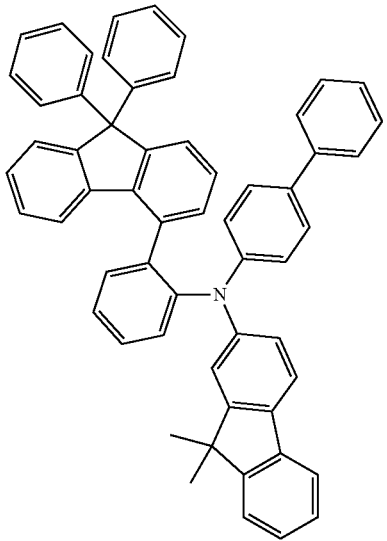 [SMILES: CC1(C)c2ccccc2-c2ccc(N(c3ccc(-c4ccccc4)cc3)c3ccccc3-c3cccc4c3-c3ccccc3C4(c3ccccc3)c3ccccc3)cc21]
formula (A-18)
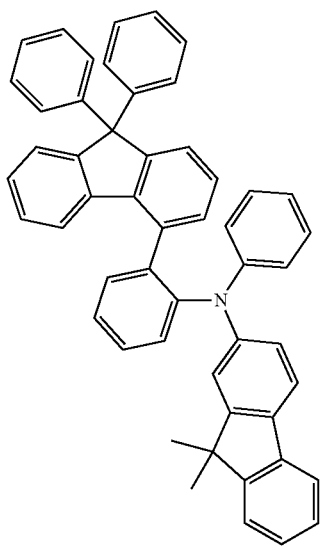 [SMILES: CC1(C)c2ccccc2-c2ccc(N(c3ccccc3)c3ccccc3-c3cccc4c3-c3ccccc3C4(c3ccccc3)c3ccccc3)cc21]
formula (A-19)
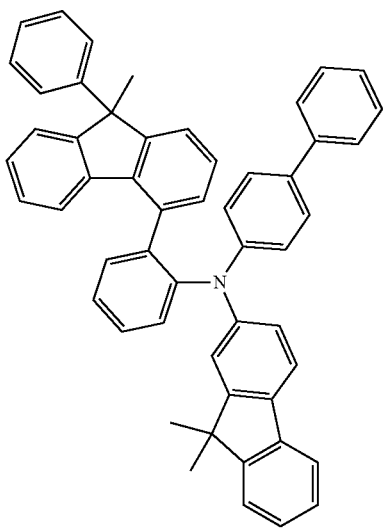 [SMILES: CC1(C)c2ccccc2-c2ccc(N(c3ccc(-c4ccccc4)cc3)c3ccccc3-c3cccc4c3-c3ccccc3C4(C)c3ccccc3)cc21]

formula (A-20)
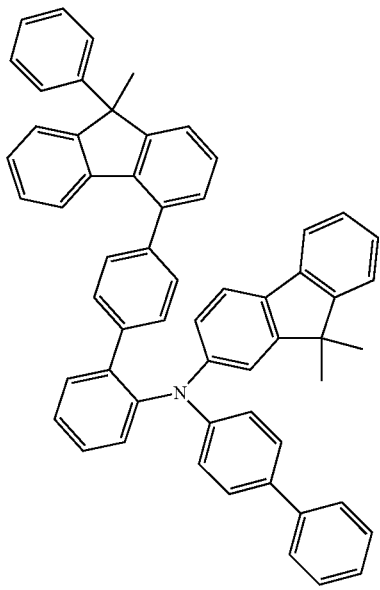 [SMILES: CC1(C)c2ccccc2-c2ccc(N(c3ccc(-c4ccccc4)cc3)c3ccccc3-c3ccc(-c4cccc5c4-c4ccccc4C5(C)c4ccccc4)cc3)cc21]
formula (A-21)
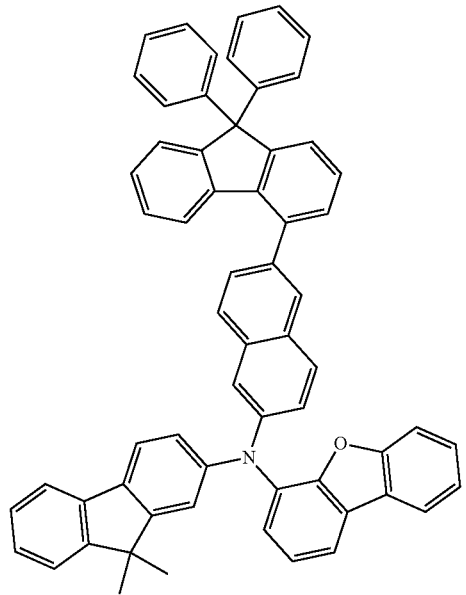 [SMILES: CC1(C)c2ccccc2-c2ccc(N(c3ccc4cc(-c5cccc6c5-c5ccccc5C6(c5ccccc5)c5ccccc5)ccc4c3)c3cccc4c3oc3ccccc34)cc21]

formula (A-22)
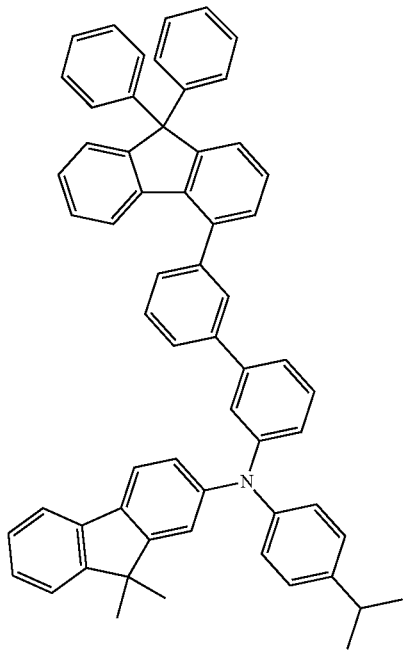 [SMILES: CC(C)c1ccc(N(c2cccc(-c3cccc(-c4cccc5c4-c4ccccc4C5(c4ccccc4)c4ccccc4)c3)c2)c2ccc3c(c2)C(C)(C)c2ccccc2-3)cc1]
formula (A-23)
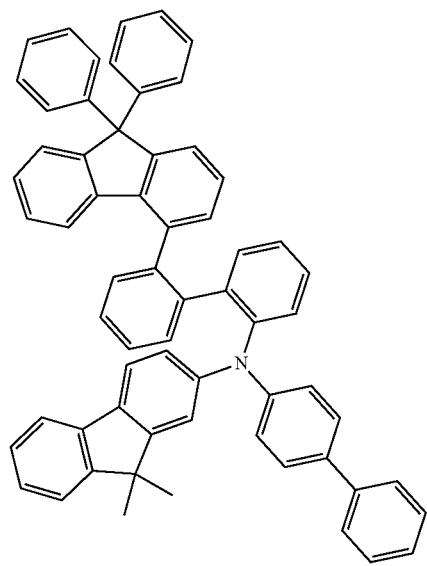 [SMILES: CC1(C)c2ccccc2-c2ccc(N(c3ccc(-c4ccccc4)cc3)c3ccccc3-c3ccccc3-c3cccc4c3-c3ccccc3C4(c3ccccc3)c3ccccc3)cc21]

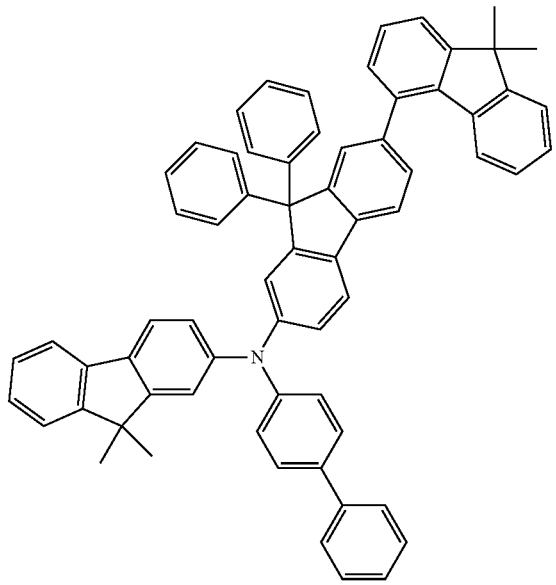 [SMILES: CC1(C)c2ccccc2-c2ccc(N(c3ccc(-c4ccccc4)cc3)c3ccc4c(c3)C(c3ccccc3)(c3ccccc3)c3cc(-c5cccc6c5-c5ccccc5C6(C)C)ccc3-4)cc21]
formula (A-24)
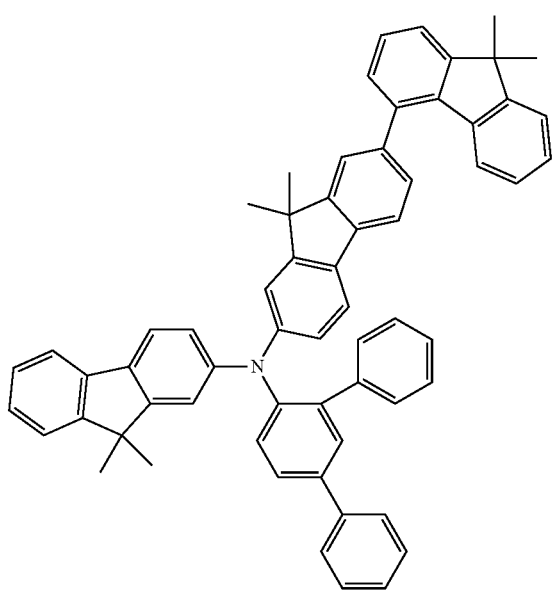 [SMILES: CC1(C)c2ccccc2-c2ccc(N(c3ccc4c(c3)C(C)(C)c3cc(-c5cccc6c5-c5ccccc5C6(C)C)ccc3-4)c3ccc(-c4ccccc4)cc3-c3ccccc3)cc21]
formula (A-25)

formula (A-26)
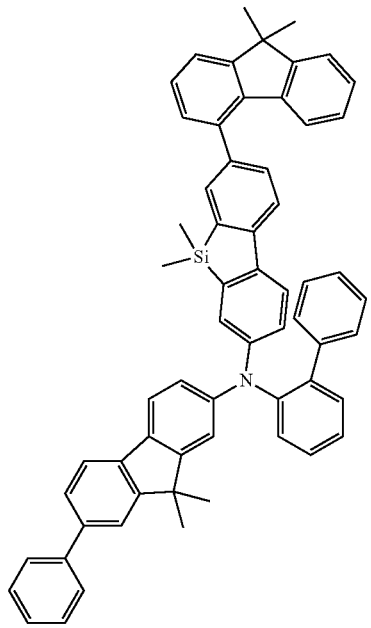 [SMILES: CC1(C)c2cc(-c3ccccc3)ccc2-c2ccc(N(c3ccc4c(c3)[Si](C)(C)c3cc(-c5cccc6c5-c5ccccc5C6(C)C)ccc3-4)c3ccccc3-c3ccccc3)cc21]
formula (A-27)
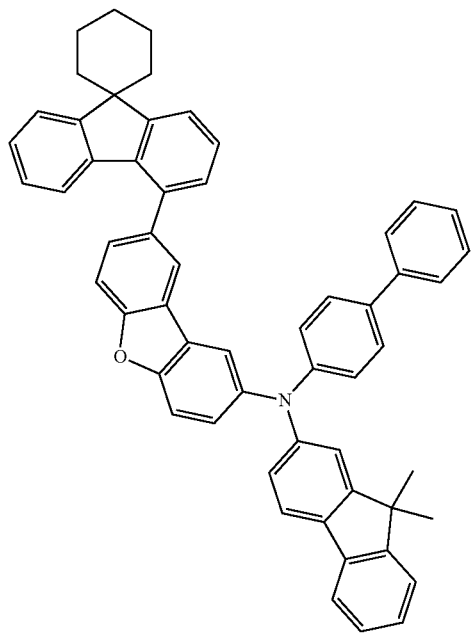 [SMILES: CC1(C)c2ccccc2-c2ccc(N(c3ccc(-c4ccccc4)cc3)c3ccc4oc5ccc(-c6cccc7c6-c6ccccc6C76CCCCC6)cc5c4c3)cc21]

-continued
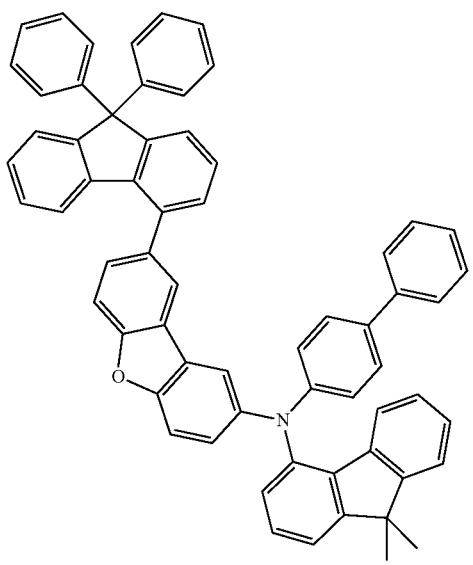 [SMILES: CC1(C)c2ccccc2-c2c(N(c3ccc(-c4ccccc4)cc3)c3ccc4oc5ccc(-c6cccc7c6-c6ccccc6C7(c6ccccc6)c6ccccc6)cc5c4c3)cccc21]
formula (A-28)
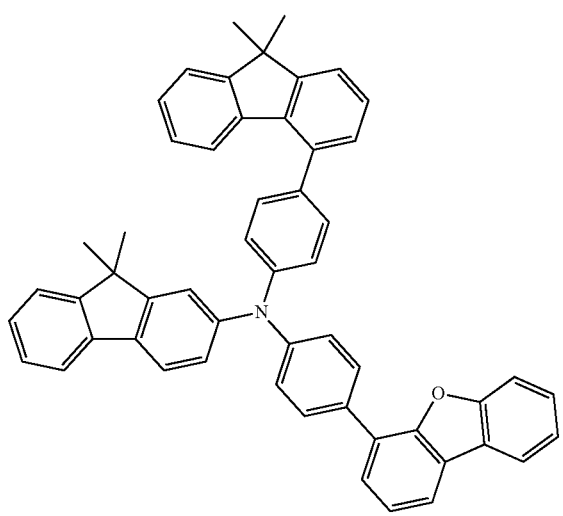 [SMILES: CC1(C)c2ccccc2-c2ccc(N(c3ccc(-c4cccc5c4-c4ccccc4C5(C)C)cc3)c3ccc(-c4cccc5c4oc4ccccc45)cc3)cc21]
formula (A-29)
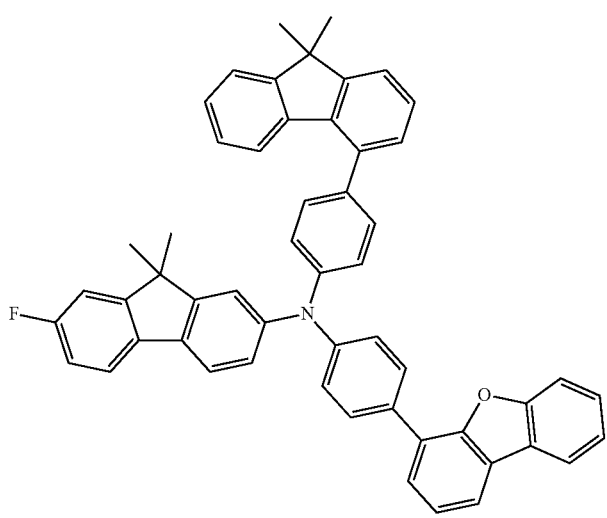 [SMILES: CC1(C)c2cc(F)ccc2-c2ccc(N(c3ccc(-c4cccc5c4-c4ccccc4C5(C)C)cc3)c3ccc(-c4cccc5c4oc4ccccc45)cc3)cc21]
formula (A-30)

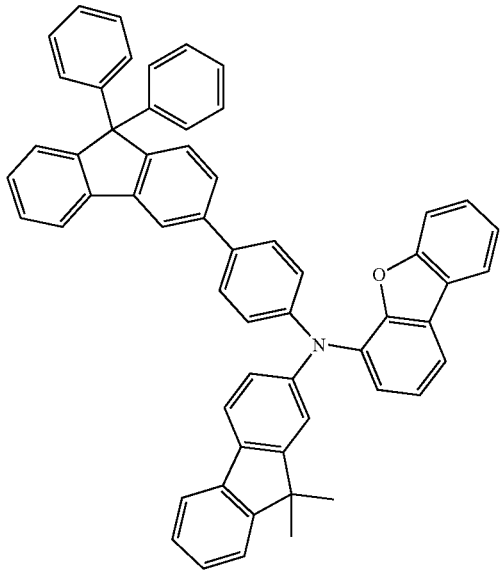 [SMILES: CC1(C)c2ccccc2-c2ccc(N(c3ccc(-c4ccc5c(c4)-c4ccccc4C5(c4ccccc4)c4ccccc4)cc3)c3cccc4c3oc3ccccc34)cc21]
formula (A-31)
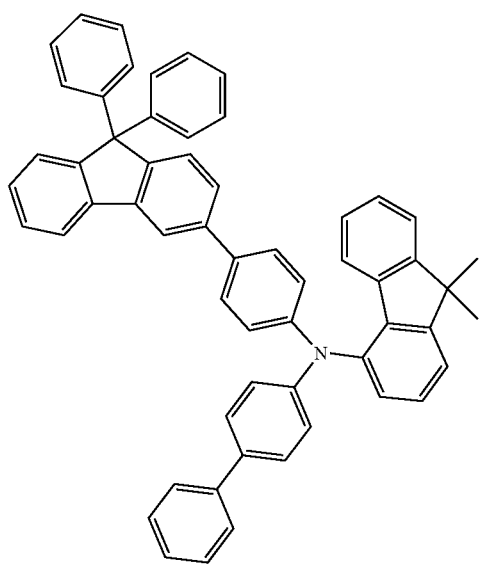 [SMILES: CC1(C)c2ccccc2-c2c(N(c3ccc(-c4ccccc4)cc3)c3ccc(-c4ccc5c(c4)-c4ccccc4C5(c4ccccc4)c4ccccc4)cc3)cccc21]
formula (A-32)
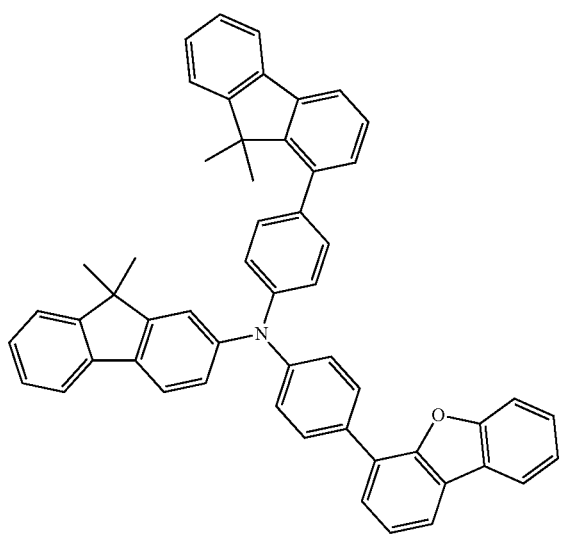 [SMILES: CC1(C)c2ccccc2-c2ccc(N(c3ccc(-c4cccc5c4C(C)(C)c4ccccc4-5)cc3)c3ccc(-c4cccc5c4oc4ccccc45)cc3)cc21]
formula (A-33)

-continued
formula (A-34)
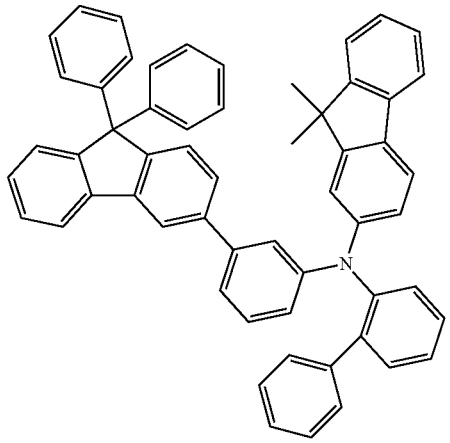 [SMILES: CC1(C)c2ccccc2-c2ccc(N(c3cccc(-c4ccc5c(c4)-c4ccccc4C5(c4ccccc4)c4ccccc4)c3)c3ccccc3-c3ccccc3)cc21]
formula (A-35)
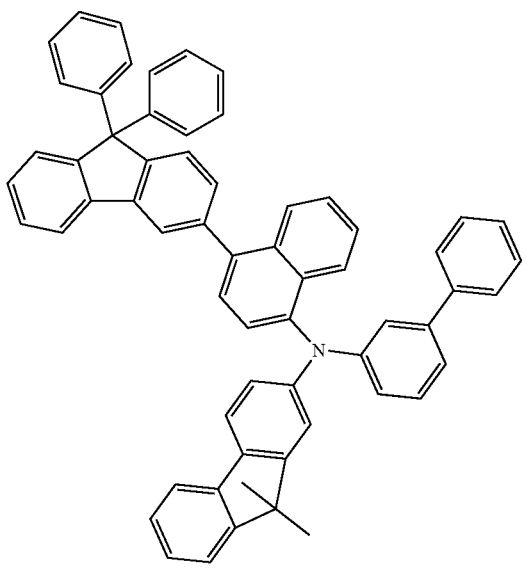
formula (A-36)
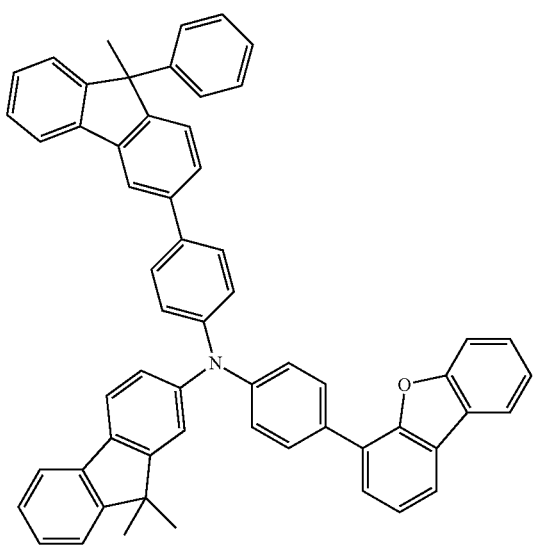 [SMILES: CC1(C)c2ccccc2-c2ccc(N(c3ccc(-c4ccc5c(c4)-c4ccccc4C5(C)c4ccccc4)cc3)c3ccc(-c4cccc5c4oc4ccccc45)cc3)cc21]

formula (A-37)
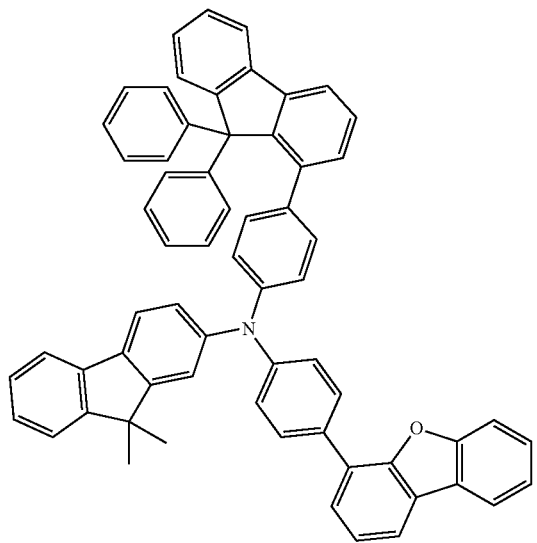 [SMILES: CC1(C)c2ccccc2-c2ccc(N(c3ccc(-c4cccc5c4C(c4ccccc4)(c4ccccc4)c4ccccc4-5)cc3)c3ccc(-c4cccc5c4oc4ccccc45)cc3)cc21]
formula (A-38)
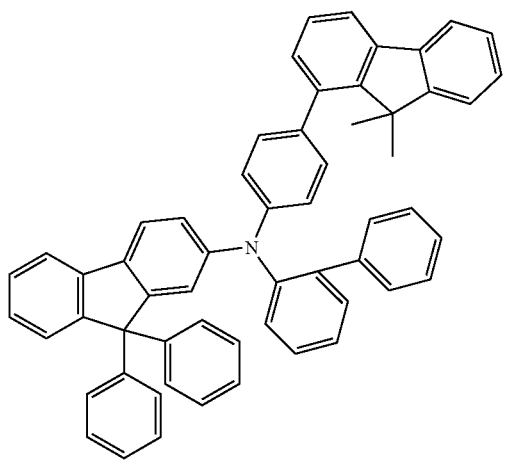 [SMILES: CC1(C)c2ccccc2-c2cccc(-c3ccc(N(c4ccc5c(c4)C(c4ccccc4)(c4ccccc4)c4ccccc4-5)c4ccccc4-c4ccccc4)cc3)c21]
formula (A-39)
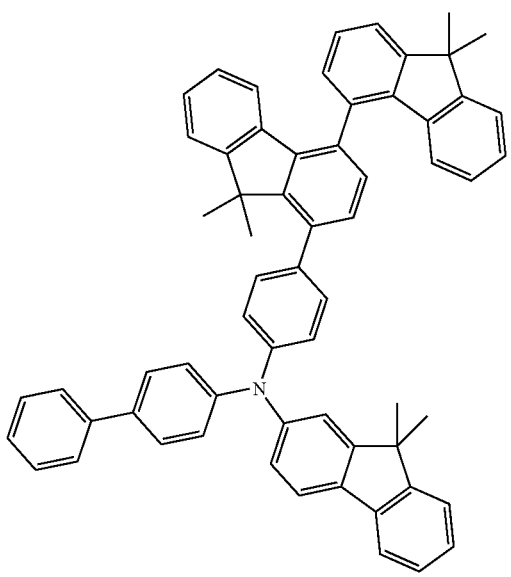 [SMILES: CC1(C)c2ccccc2-c2ccc(N(c3ccc(-c4ccccc4)cc3)c3ccc(-c4ccc(-c5cccc6c5-c5ccccc5C6(C)C)c5c4C(C)(C)c4ccccc4-5)cc3)cc21]

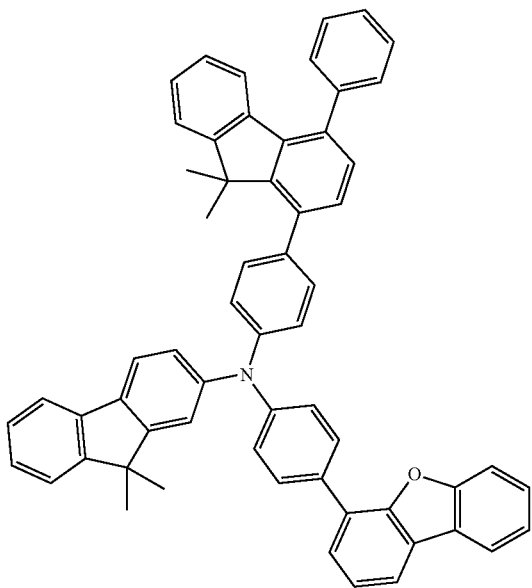 [SMILES: CC1(C)c2ccccc2-c2ccc(N(c3ccc(-c4ccc(-c5ccccc5)c5c4C(C)(C)c4ccccc4-5)cc3)c3ccc(-c4cccc5c4oc4ccccc45)cc3)cc21]
formula (A-40)
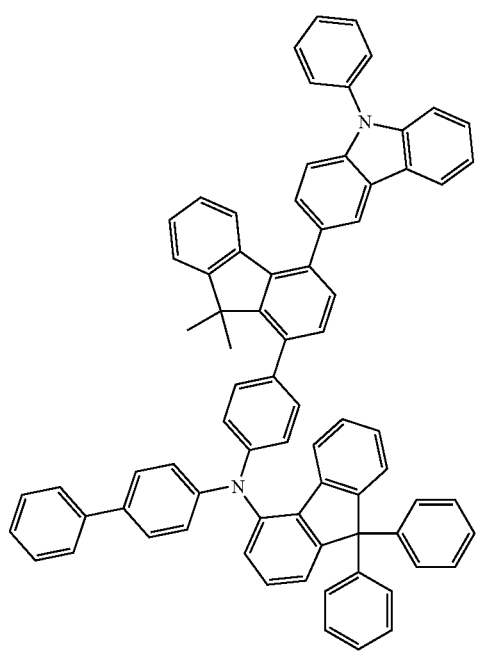 [SMILES: CC1(C)c2ccccc2-c2c(-c3ccc4c(c3)c3ccccc3n4-c3ccccc3)ccc(-c3ccc(N(c4ccc(-c5ccccc5)cc4)c4cccc5c4-c4ccccc4C5(c4ccccc4)c4ccccc4)cc3)c21]
formula (A-41)

formula (A-42)
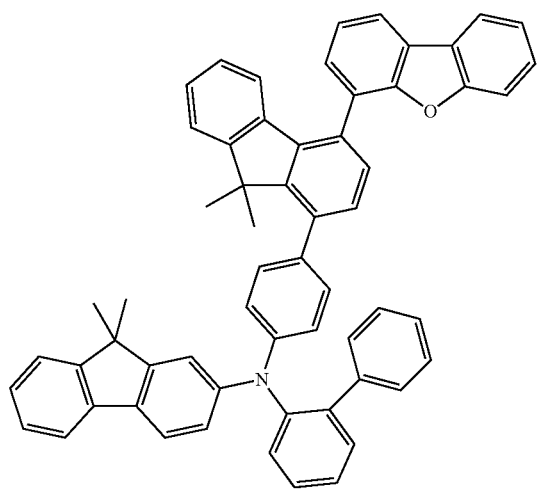 [SMILES: CC1(C)c2ccccc2-c2ccc(N(c3ccc(-c4ccc(-c5cccc6c5oc5ccccc56)c5c4C(C)(C)c4ccccc4-5)cc3)c3ccccc3-c3ccccc3)cc21]
formula (A-43)
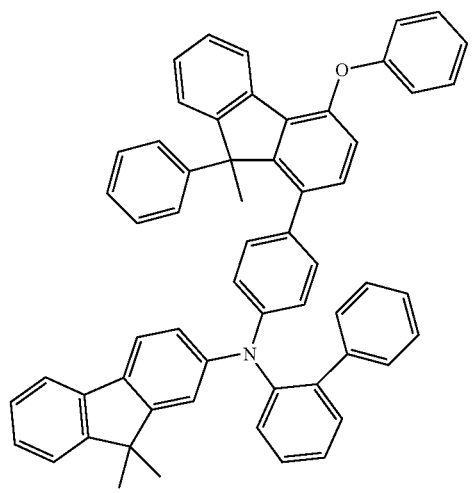 [SMILES: CC1(C)c2ccccc2-c2ccc(N(c3ccc(-c4ccc(Oc5ccccc5)c5c4C(C)(c4ccccc4)c4ccccc4-5)cc3)c3ccccc3-c3ccccc3)cc21]
formula (A-44)
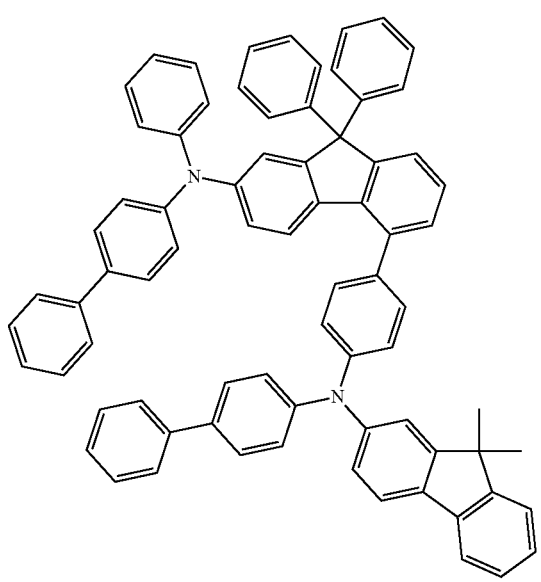 [SMILES: CC1(C)c2ccccc2-c2ccc(N(c3ccc(-c4ccccc4)cc3)c3ccc(-c4cccc5c4-c4ccc(N(c6ccccc6)c6ccc(-c7ccccc7)cc6)cc4C5(c4ccccc4)c4ccccc4)cc3)cc21]

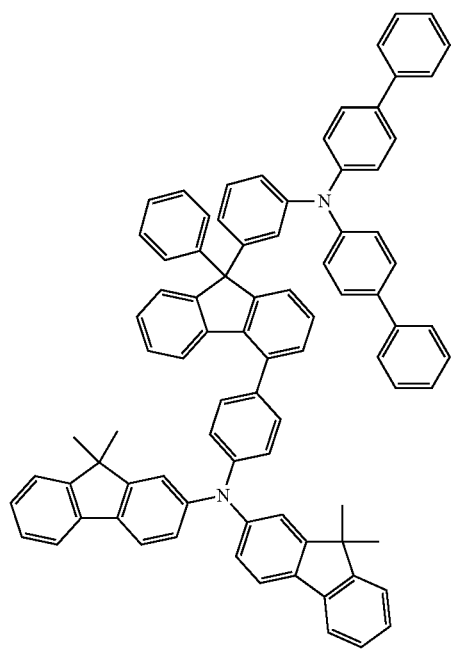 [SMILES: CC1(C)c2ccccc2-c2ccc(N(c3ccc(-c4cccc5c4-c4ccccc4C5(c4ccccc4)c4cccc(N(c5ccc(-c6ccccc6)cc5)c5ccc(-c6ccccc6)cc5)c4)cc3)c3ccc4c(c3)C(C)(C)c3ccccc3-4)cc21]
formula (A-45)
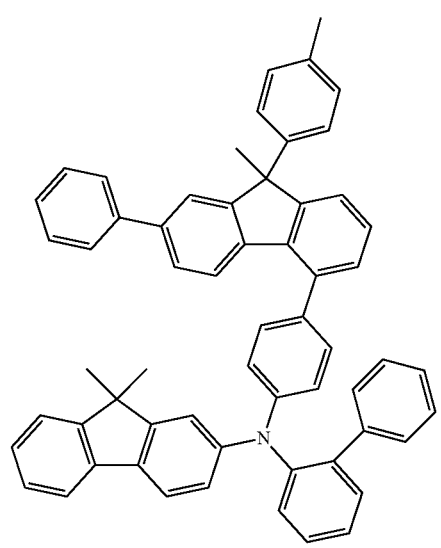 [SMILES: Cc1ccc(C2(C)c3cc(-c4ccccc4)ccc3-c3c(-c4ccc(N(c5ccc6c(c5)C(C)(C)c5ccccc5-6)c5ccccc5-c5ccccc5)cc4)cccc32)cc1]
formula (A-46)

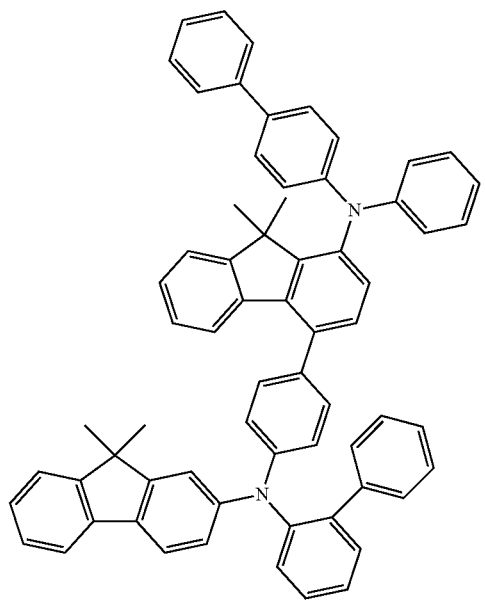 [SMILES: CC1(C)c2ccccc2-c2ccc(N(c3ccc(-c4ccc(N(c5ccccc5)c5ccc(-c6ccccc6)cc5)c5c4-c4ccccc4C5(C)C)cc3)c3ccccc3-c3ccccc3)cc21]
formula (A-47)
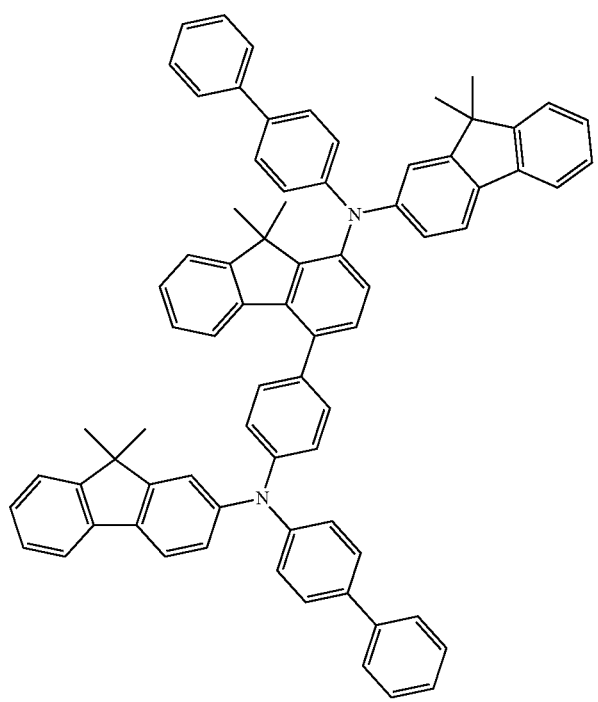 [SMILES: CC1(C)c2ccccc2-c2ccc(N(c3ccc(-c4ccccc4)cc3)c3ccc(-c4ccc(N(c5ccc(-c6ccccc6)cc5)c5ccc6c(c5)C(C)(C)c5ccccc5-6)c5c4-c4ccccc4C5(C)C)cc3)cc21]
formula (A-48)

formula (A-49)
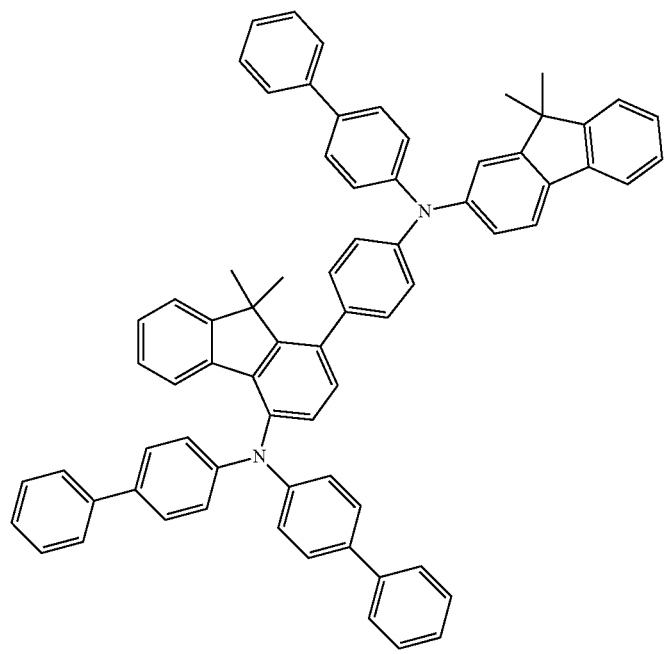 [SMILES: CC1(C)c2ccccc2-c2ccc(N(c3ccc(-c4ccccc4)cc3)c3ccc(-c4ccc(N(c5ccc(-c6ccccc6)cc5)c5ccc(-c6ccccc6)cc5)c5c4C(C)(C)c4ccccc4-5)cc3)cc21]
formula (A-50)
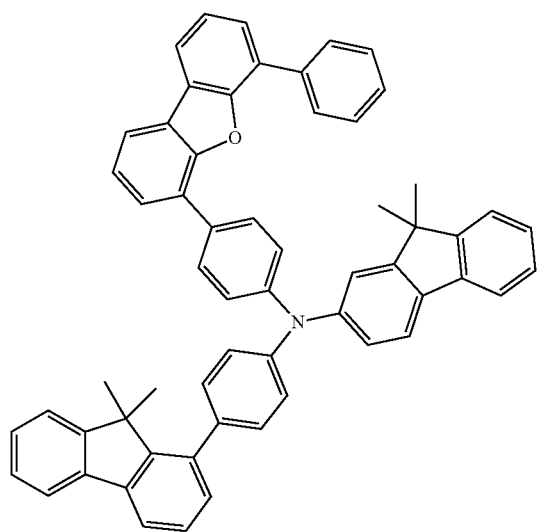 [SMILES: CC1(C)c2ccccc2-c2ccc(N(c3ccc(-c4cccc5c4C(C)(C)c4ccccc4-5)cc3)c3ccc(-c4cccc5c4oc4c(-c6ccccc6)cccc45)cc3)cc21]

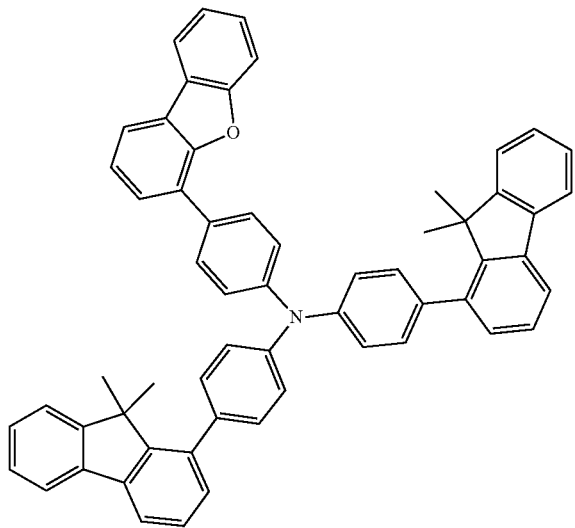 [SMILES: CC1(C)c2ccccc2-c2cccc(-c3ccc(N(c4ccc(-c5cccc6c5C(C)(C)c5ccccc5-6)cc4)c4ccc(-c5cccc6c5oc5ccccc56)cc4)cc3)c21]
formula (A-51)
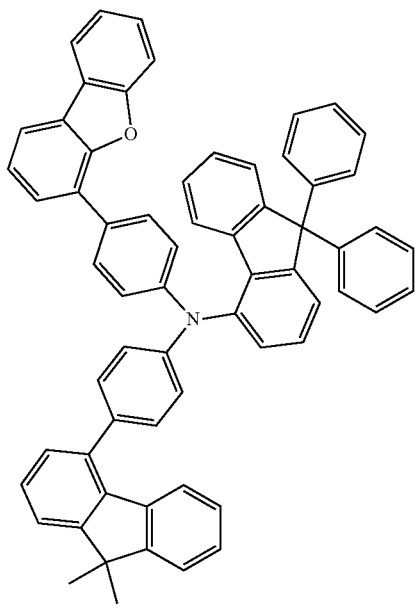 [SMILES: CC1(C)c2ccccc2-c2c(-c3ccc(N(c4ccc(-c5cccc6c5oc5ccccc56)cc4)c4cccc5c4-c4ccccc4C5(c4ccccc4)c4ccccc4)cc3)cccc21]
formula (A-52)

-continued
formula (A-53)
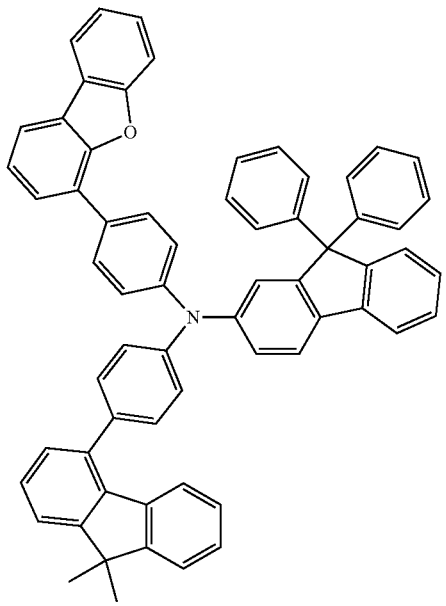 [SMILES: CC1(C)c2ccccc2-c2c(-c3ccc(N(c4ccc(-c5cccc6c5oc5ccccc56)cc4)c4ccc5c(c4)C(c4ccccc4)(c4ccccc4)c4ccccc4-5)cc3)cccc21]
formula (A-54)
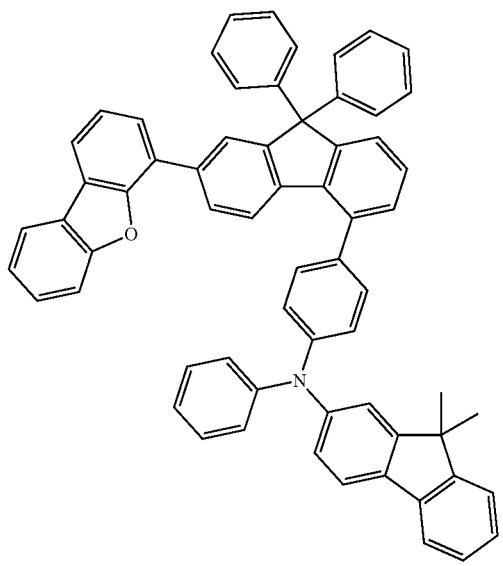 [SMILES: CC1(C)c2ccccc2-c2ccc(N(c3ccccc3)c3ccc(-c4cccc5c4-c4ccc(-c6cccc7c6oc6ccccc67)cc4C5(c4ccccc4)c4ccccc4)cc3)cc21]

formula (A-55)
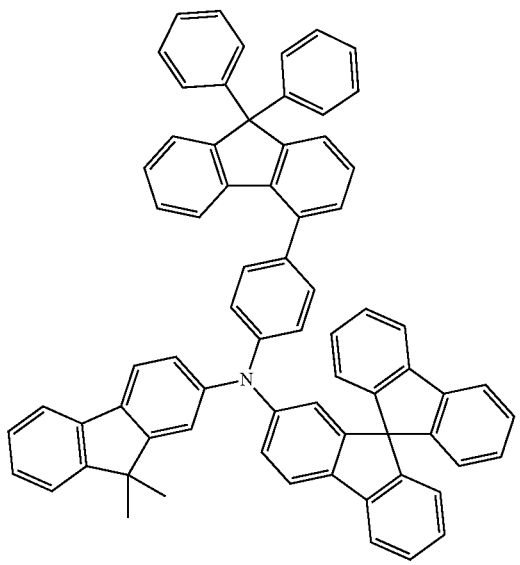 [SMILES: CC1(C)c2ccccc2-c2ccc(N(c3ccc(-c4cccc5c4-c4ccccc4C5(c4ccccc4)c4ccccc4)cc3)c3ccc4c(c3)C3(c5ccccc5-c5ccccc53)c3ccccc3-4)cc21]
formula (A-56)
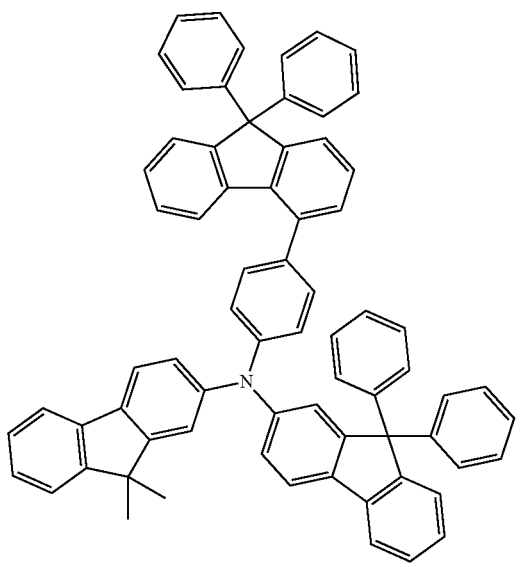 [SMILES: CC1(C)c2ccccc2-c2ccc(N(c3ccc(-c4cccc5c4-c4ccccc4C5(c4ccccc4)c4ccccc4)cc3)c3ccc4c(c3)C(c3ccccc3)(c3ccccc3)c3ccccc3-4)cc21]

-continued
formula (A-57)
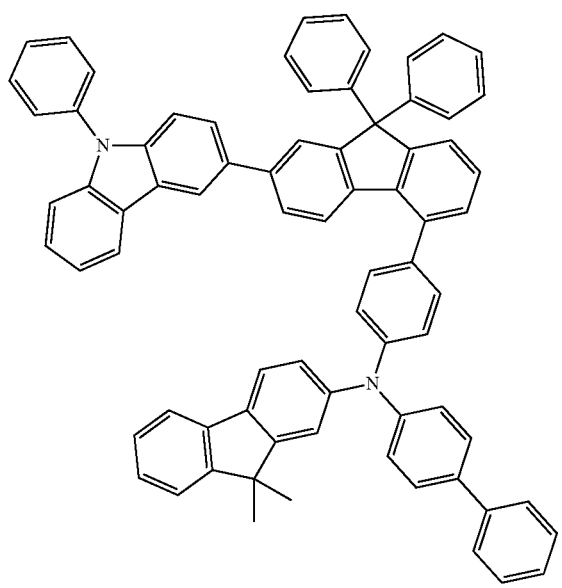 [SMILES: CC1(C)c2ccccc2-c2ccc(N(c3ccc(-c4ccccc4)cc3)c3ccc(-c4cccc5c4-c4ccc(-c6ccc7c(c6)c6ccccc6n7-c6ccccc6)cc4C5(c4ccccc4)c4ccccc4)cc3)cc21]
formula (A-59)
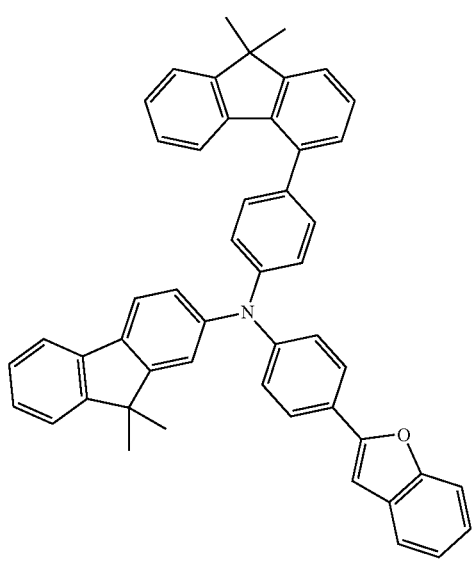 [SMILES: CC1(C)c2ccccc2-c2ccc(N(c3ccc(-c4cc5ccccc5o4)cc3)c3ccc(-c4cccc5c4-c4ccccc4C5(C)C)cc3)cc21]

formula (A-60)
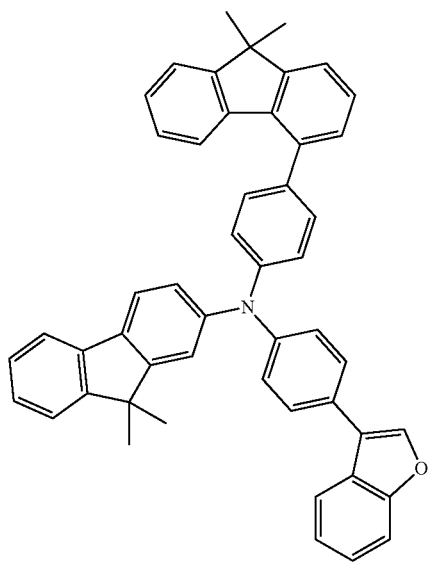 [SMILES: CC1(C)c2ccccc2-c2ccc(N(c3ccc(-c4cccc5c4-c4ccccc4C5(C)C)cc3)c3ccc(-c4coc5ccccc45)cc3)cc21]
formula (A-61)
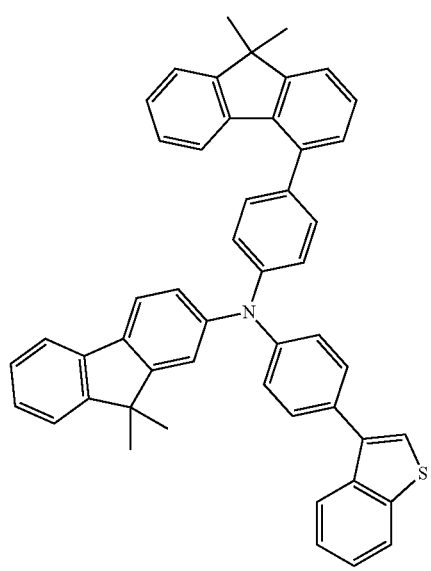 [SMILES: CC1(C)c2ccccc2-c2ccc(N(c3ccc(-c4cccc5c4-c4ccccc4C5(C)C)cc3)c3ccc(-c4csc5ccccc45)cc3)cc21]

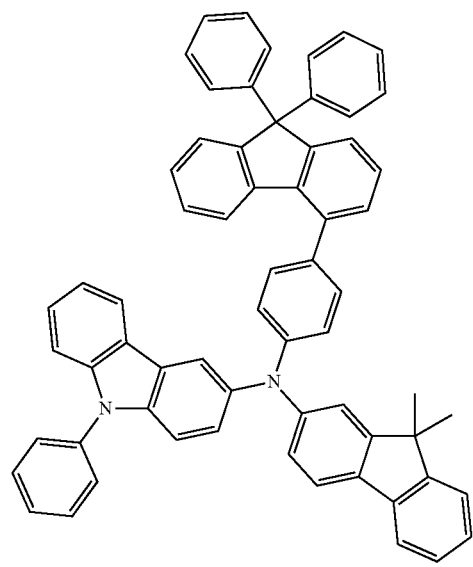 [SMILES: CC1(C)c2ccccc2-c2ccc(N(c3ccc(-c4cccc5c4-c4ccccc4C5(c4ccccc4)c4ccccc4)cc3)c3ccc4c(c3)c3ccccc3n4-c3ccccc3)cc21]
formula (A-62)
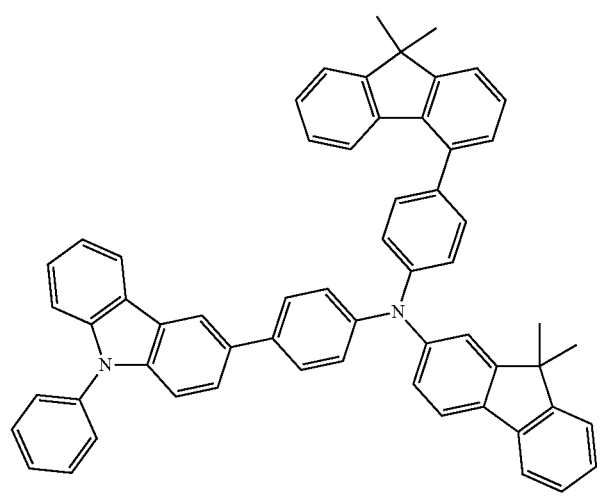 [SMILES: CC1(C)c2ccccc2-c2ccc(N(c3ccc(-c4ccc5c(c4)c4ccccc4n5-c4ccccc4)cc3)c3ccc(-c4cccc5c4-c4ccccc4C5(C)C)cc3)cc21]
formula (A-63)

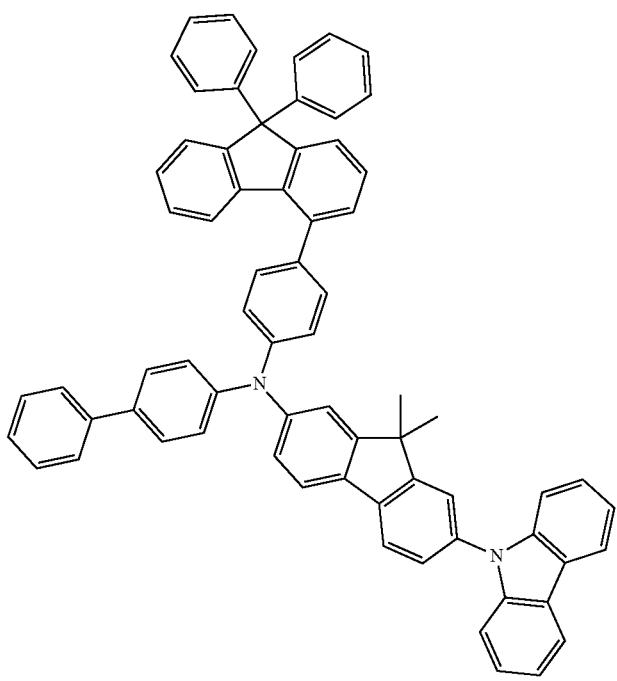 [SMILES: CC1(C)c2cc(N(c3ccc(-c4ccccc4)cc3)c3ccc(-c4cccc5c4-c4ccccc4C5(c4ccccc4)c4ccccc4)cc3)ccc2-c2ccc(-n3c4ccccc4c4ccccc43)cc21]
formula (A-64)
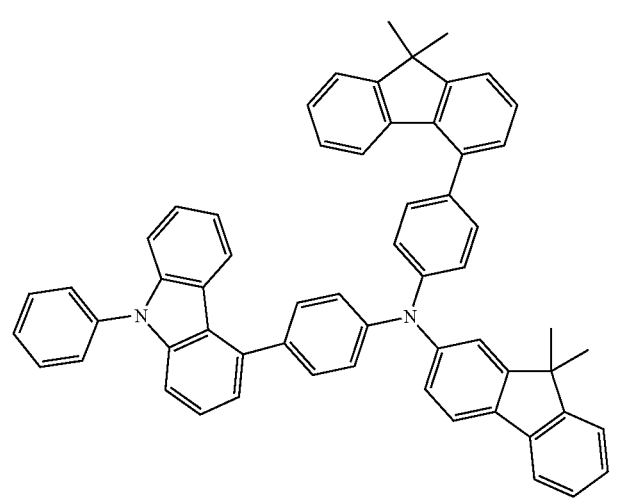 [SMILES: CC1(C)c2ccccc2-c2ccc(N(c3ccc(-c4cccc5c4-c4ccccc4C5(C)C)cc3)c3ccc(-c4cccc5c4c4ccccc4n5-c4ccccc4)cc3)cc21]
formula (A-65)

-continued
formula (A-66)
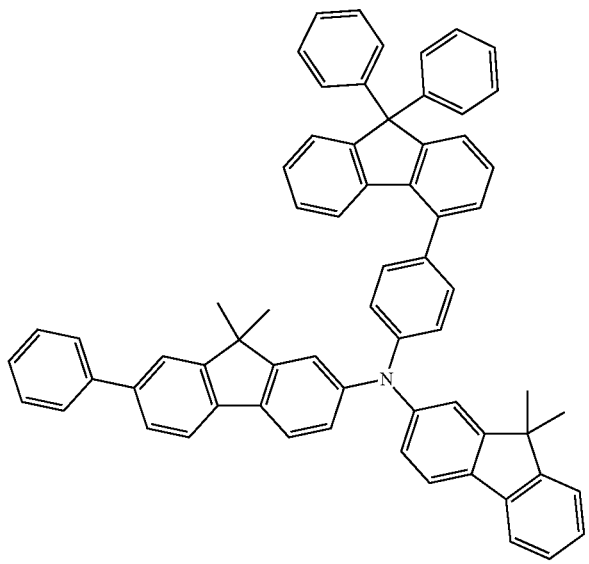 [SMILES: CC1(C)c2ccccc2-c2ccc(N(c3ccc(-c4cccc5c4-c4ccccc4C5(c4ccccc4)c4ccccc4)cc3)c3ccc4c(c3)C(C)(C)c3cc(-c5ccccc5)ccc3-4)cc21]
formula (A-67)
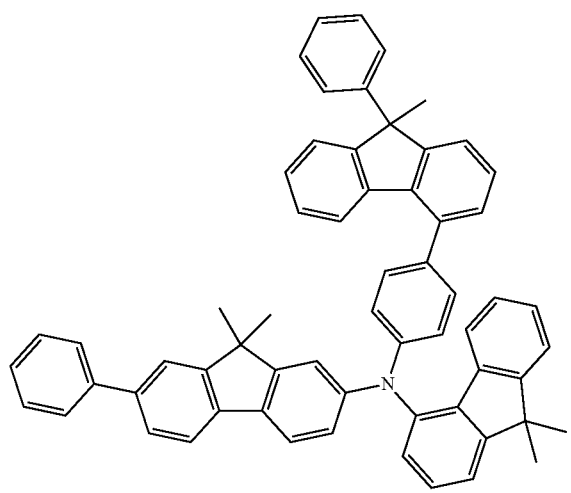 [SMILES: CC1(C)c2cc(-c3ccccc3)ccc2-c2ccc(N(c3ccc(-c4cccc5c4-c4ccccc4C5(C)c4ccccc4)cc3)c3cccc4c3-c3ccccc3C4(C)C)cc21]
formula (A-68)
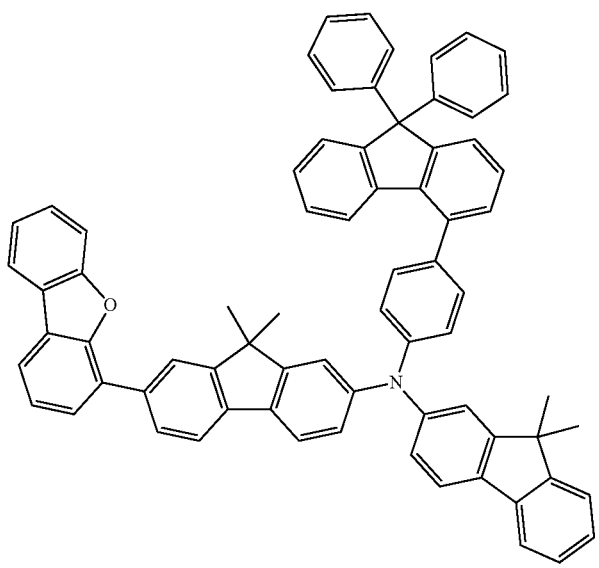 [SMILES: CC1(C)c2ccccc2-c2ccc(N(c3ccc(-c4cccc5c4-c4ccccc4C5(c4ccccc4)c4ccccc4)cc3)c3ccc4c(c3)C(C)(C)c3cc(-c5cccc6c5oc5ccccc56)ccc3-4)cc21]

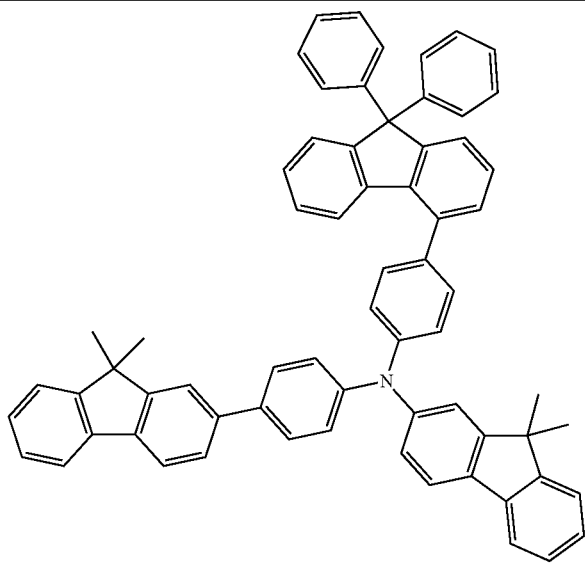

formula (A-69)

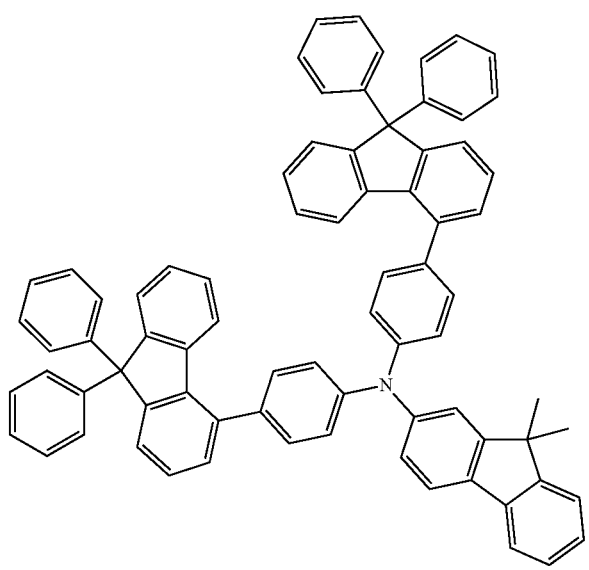 [SMILES: CC1(C)c2ccccc2-c2ccc(N(c3ccc(-c4cccc5c4-c4ccccc4C5(c4ccccc4)c4ccccc4)cc3)c3ccc(-c4cccc5c4-c4ccccc4C5(c4ccccc4)c4ccccc4)cc3)cc21]

formula (A-70)

The compounds of the formula (1) described above may be substituted by reactive leaving groups, such as bromine, iodine, chlorine, boronic acid or boronic acid ester. These can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (1), where the bond(s) to the polymer, oligomer or dendrimer may be localised at any desired possible positions in formula (1). Depending on the linking of the compound of the formula (1), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (1) may be linked via a trivalent or polyvalent group, for example via a trivalent or polyvalent aromatic or heteroaromatic group, to form a branched or dendritic oligomer or polymer.

The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

The compounds, polymers, oligomers and dendrimers according to the invention can be employed as compositions with other organically functional materials which are used in electronic devices. A large number of possible organically functional materials is known to the person skilled in the art from the prior art.

The present invention therefore also relates to a composition comprising one or more compounds of the formula (1) according to the invention or at least one polymer, oligomer or dendrimer according to the invention and at least one further organically functional material selected from the group consisting of fluorescent emitters, phosphorescent emitters, host materials, matrix materials, electron-transport materials, electron-injection materials, hole-conductor materials, hole-injection materials, electron-blocking materials, hole-blocking materials and p-dopants.

Preference is given here to compositions comprising one or more compounds of the formula (1) according to the invention or at least one polymer, oligomer or dendrimer according to the invention and at least one further organic semiconductor material selected from the group consisting of electron-transport materials.

Preference is furthermore given to compositions comprising one or more compounds of the formula (1) according to the invention or at least one polymer, oligomer or dendrimer according to the invention and at least one further organic semiconductor material selected from the group consisting of hole-transport materials.

Preference is furthermore given to compositions comprising one or more compounds of the formula (1) according to the invention or at least one polymer, oligomer or dendrimer according to the invention and at least one p-dopant.

Preference is furthermore given to compositions comprising one or more compounds of the formula (1) according to the invention or at least one polymer, oligomer or dendrimer according to the invention and at least one further organic semiconductor material selected from the group consisting of the matrix materials.

For the processing of the compounds according to the invention from the liquid phase, for example by spin coating or by printing processes, formulations of the compounds according to the invention are necessary. These formulations can be, for example, solutions, dispersions or mini-emulsions. It may be preferred to use mixtures of two or more solvents for this purpose.

The invention therefore furthermore relates to a formulation, in particular a solution, dispersion or mini-emulsion, comprising at least one compound of the formula (1), a composition comprising at least one compound of the formula (1) or at least one polymer, oligomer or dendrimer containing at least one unit of the formula (1), and at least one solvent, preferably an organic solvent. The way in which solutions of this type can be prepared is known to the person skilled in the art and is described, for example, in WO 2002/072714, WO 2003/019694 and the literature cited therein.

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol mono-butyl ether, tripropylene glycol dimethyl ether, tetraethylene glycol dimethyl ether, 2-isopropylnaphthalene, pentylbenzene, hexylbenzene, heptyl-benzene, octylbenzene, 1,1-bis(3,4-dimethylphenyl)ethane or mixtures of these solvents.

The compounds according to the invention are suitable for use in electronic devices, in particular in organic electroluminescent devices (for example OLEDs or OLECs). Depending on the substitution, the compounds are employed in different functions and layers.

The invention therefore furthermore relates to the use of a compound of the formula (1) in an electronic device, preferably in a hole-transporting layer and/or in an emitting layer.

The electronic device according to the invention is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs, LECs or LEECs), organic laser diodes (O-lasers) and organic light-emit-ting diodes (OLEDs). Particular preference is given to organic electroluminescent devices, very particularly preferably OLECs and OLEDs and especially preferably OLEDs).

The invention relates, as already stated above, to electronic devices comprising at least one compound of the formula (1). The electronic devices here are preferably selected from the devices mentioned above. Particular preference is given to organic electroluminescent devices and very particularly preferably OLEDs comprising an anode, a cathode and at least one emitting layer, characterised in that at least one organic layer, which may be an emitting layer, a hole-transport layer or another layer, comprises at least one compound of the formula (1).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, inter-layers, charge-generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). The compounds according to the invention may be present in such devices in a hole-transport layer, an emitting layer and/or in another layer. It should be noted that, for the generation of white light, an emitter compound used individually which emits in a broad wavelength range may also be suitable instead of a plurality of emitter compounds emitting in a colour.

It is preferred in accordance with the invention for the compound of the formula (1) to be employed in an electroluminescent device comprising one or more phosphorescent dopants. The compound can be used in various layers here, preferably in an hole-transport layer, a hole-injection layer or in an emitting layer. However, the compound of the formula (1) can also be employed in accordance with the invention in an electronic device comprising one or more fluorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybde-num, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to em-ploy further phosphorescent complexes without inventive step in combination with the compounds of the formula (1) in organic electroluminescent devices.

Explicit examples of suitable phosphorescent emitter compounds are furthermore revealed by the following table.

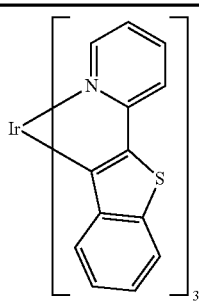

107
-continued
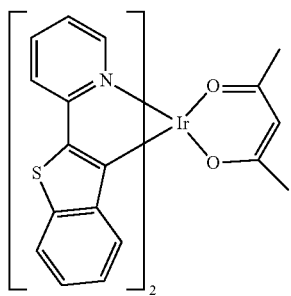
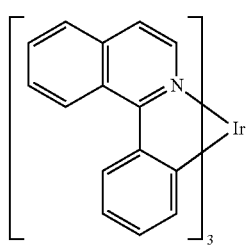
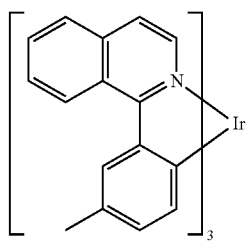
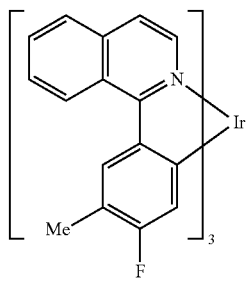
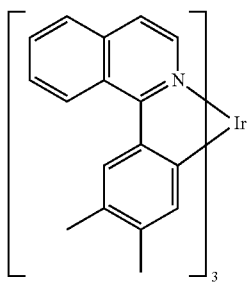
108
-continued
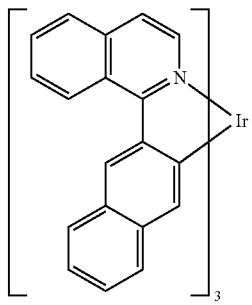
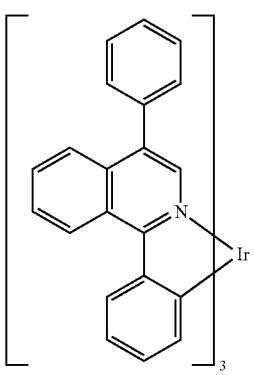
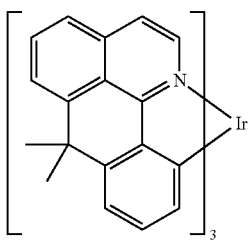
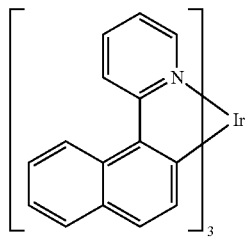
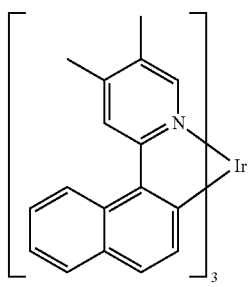

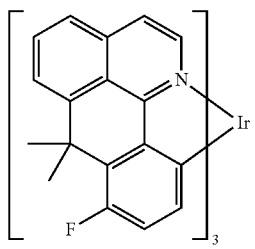
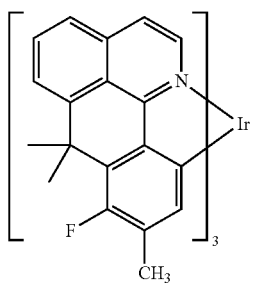
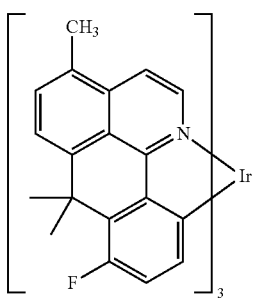
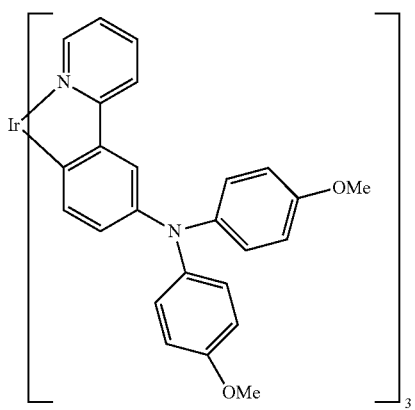
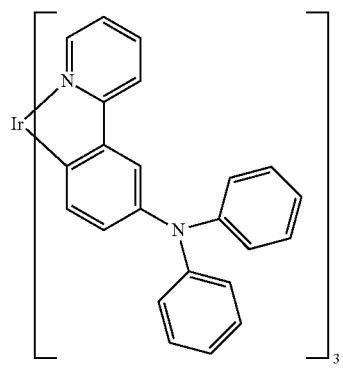
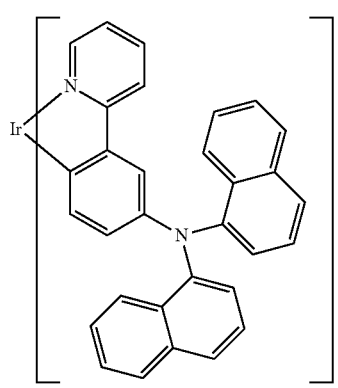
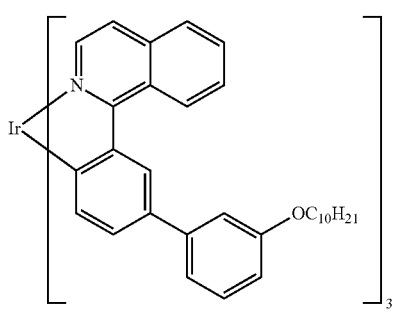
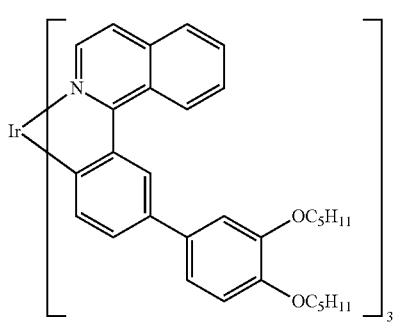
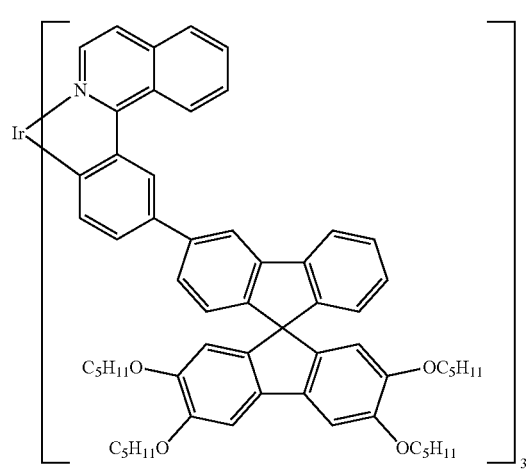

111
-continued
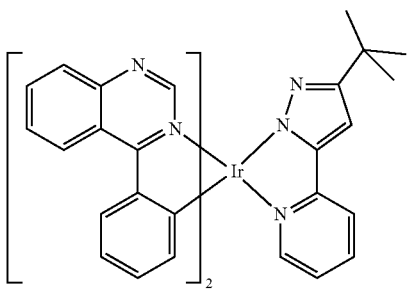
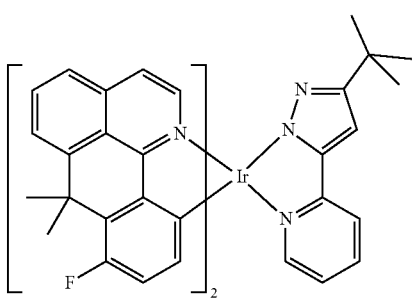
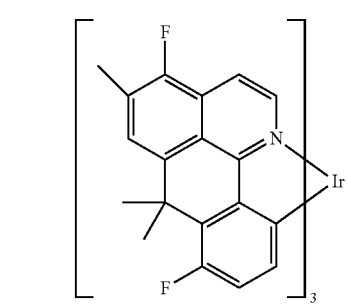
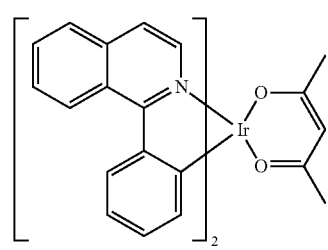
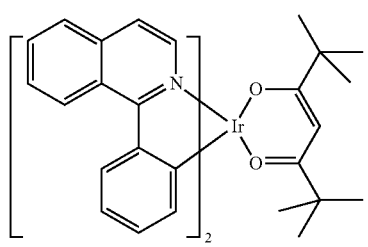
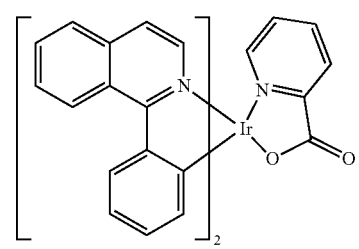
112
-continued
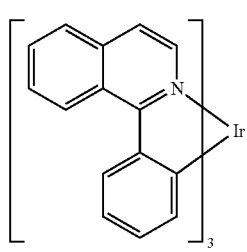
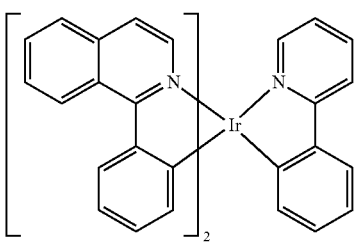
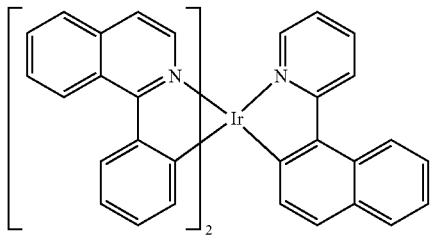
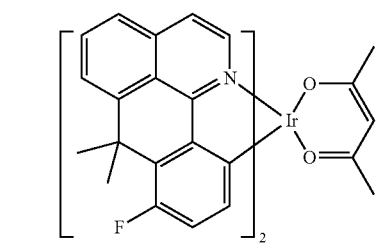
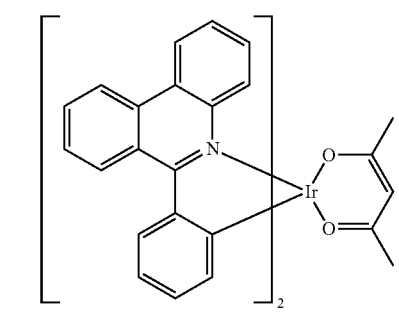
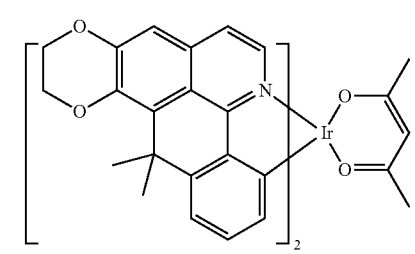

113
-continued
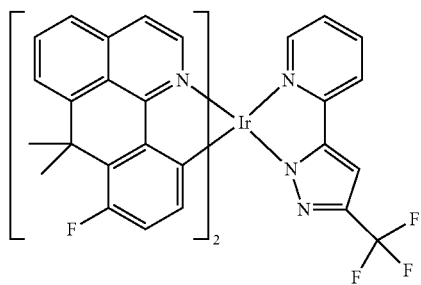
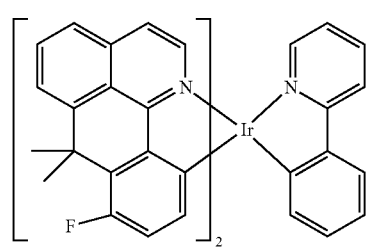
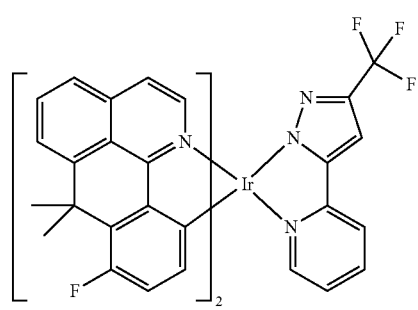
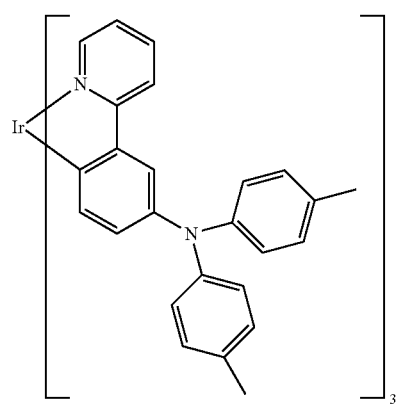
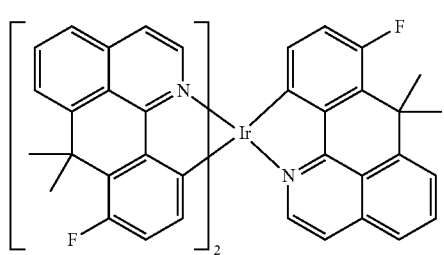
114
-continued
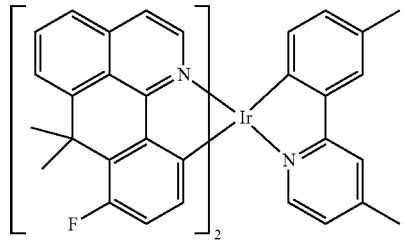
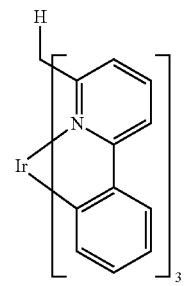
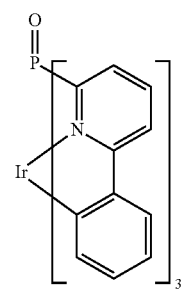
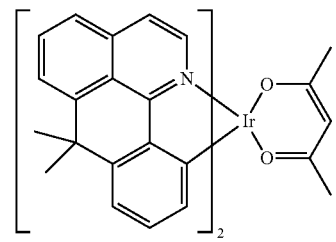
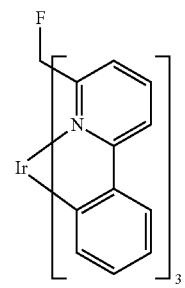
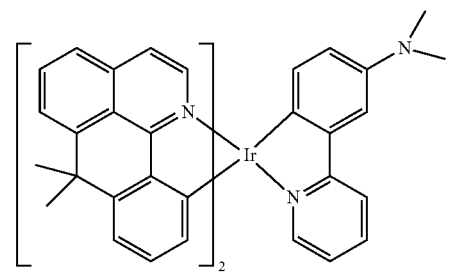

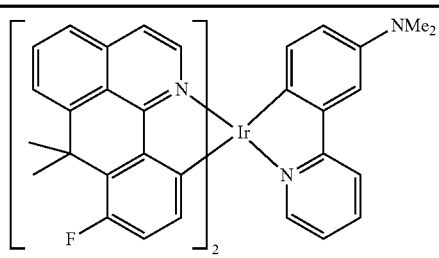
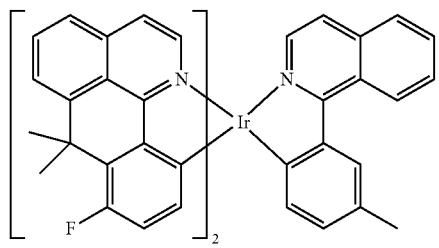
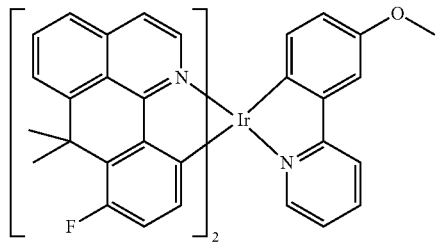
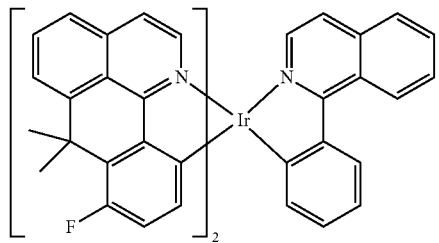
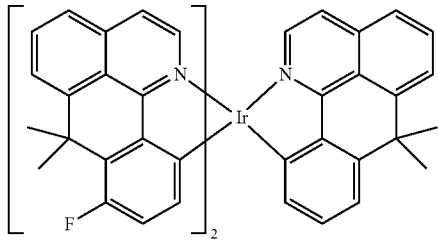
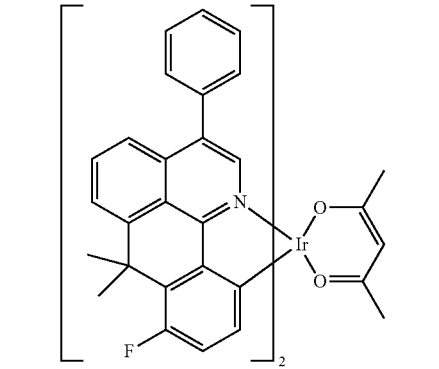
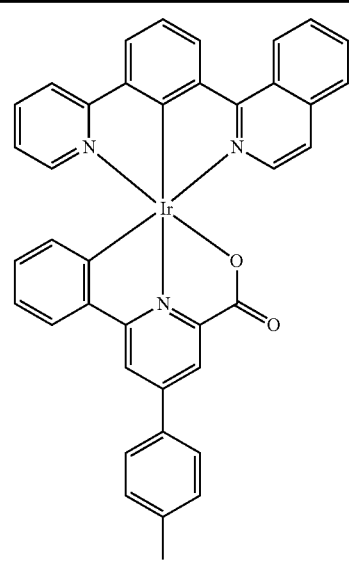
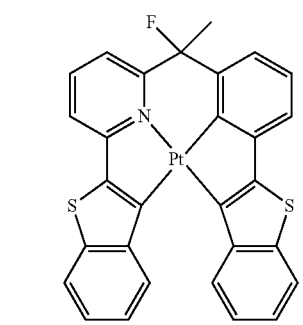
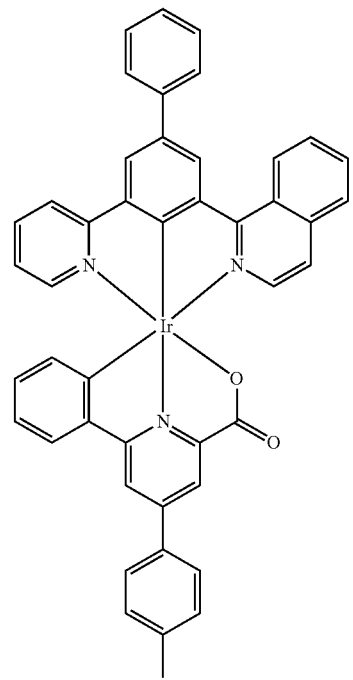

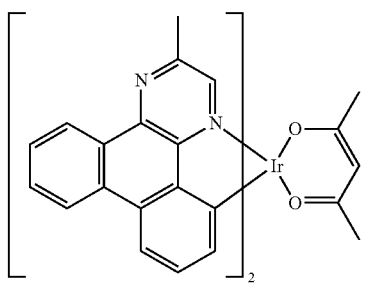
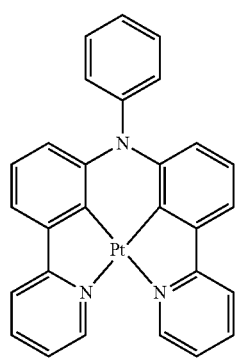
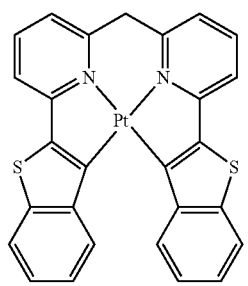
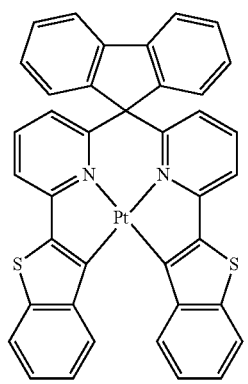
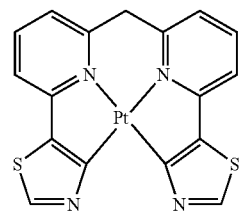
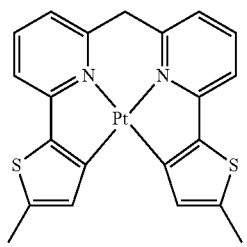
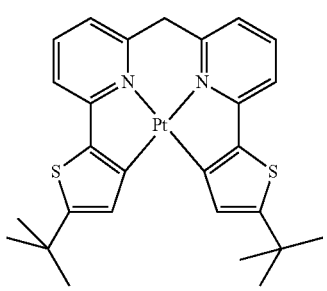
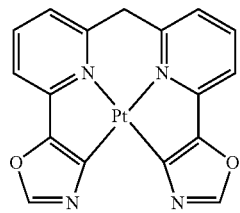
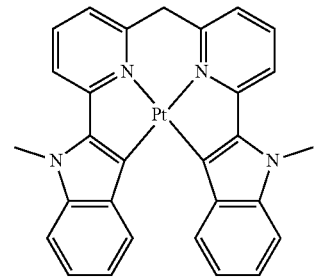
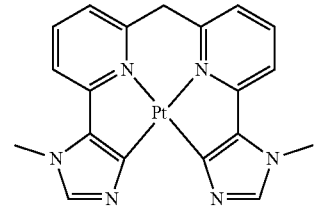

| 119 -continued | 120 -continued |
|---|---|
| 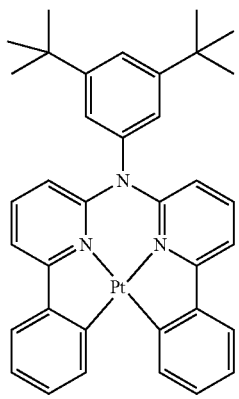 | 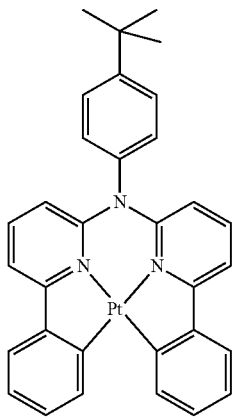 |
| 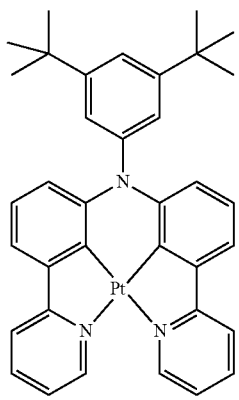 | 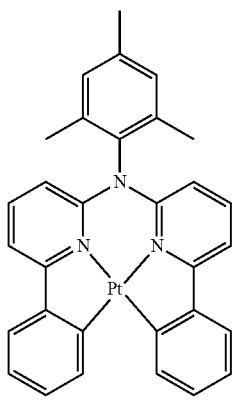 |
| 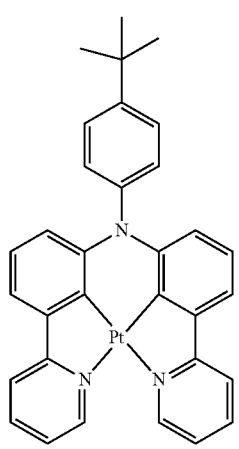 | 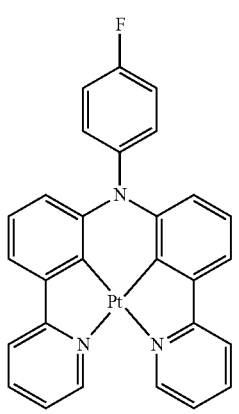 |
| 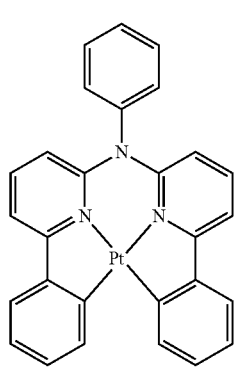 | 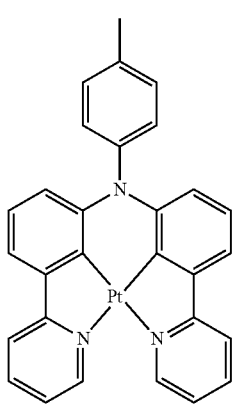 |

| 121 -continued | 122 -continued |
|---|---|
| 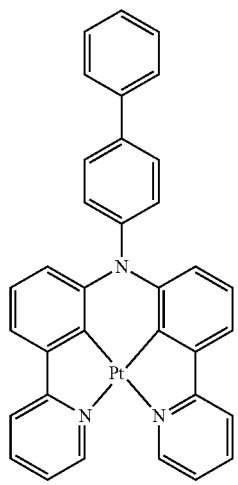 | 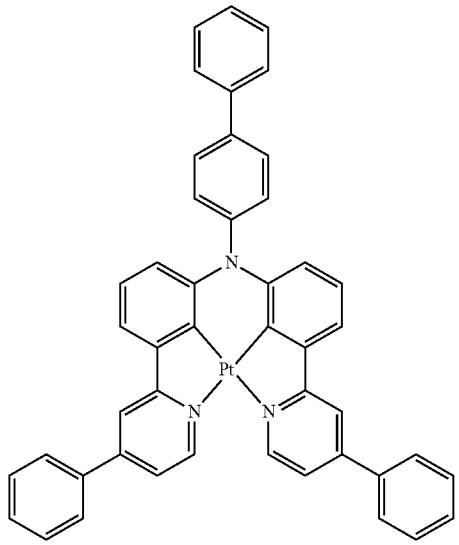 |
| 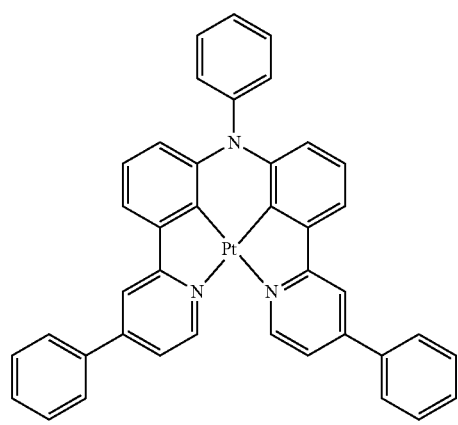 | 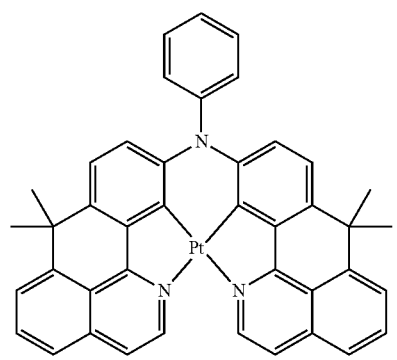 |
| 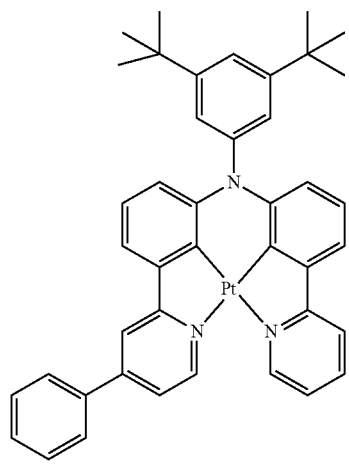 | 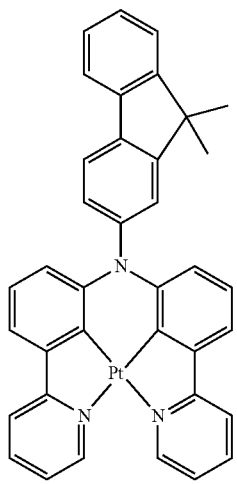 |

123
-continued
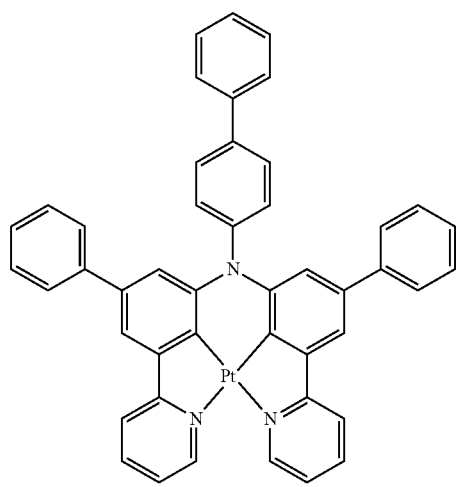
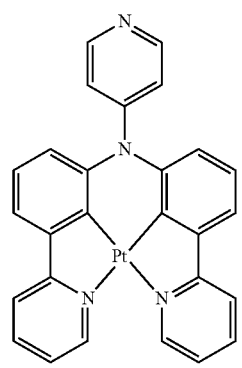
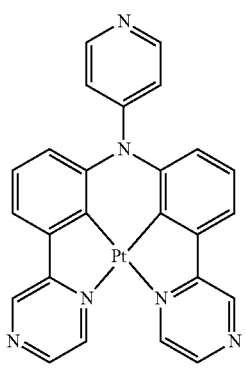
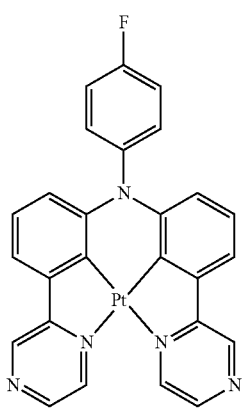
124
-continued
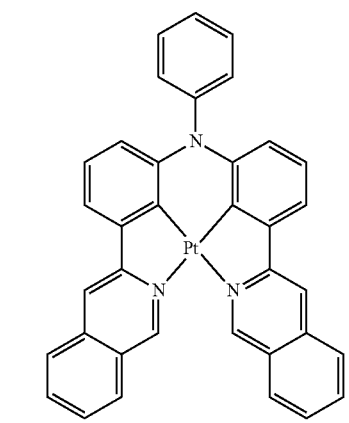
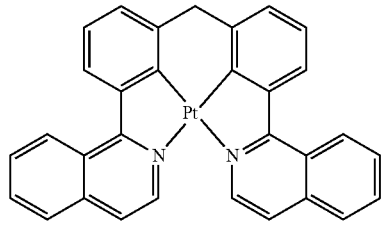
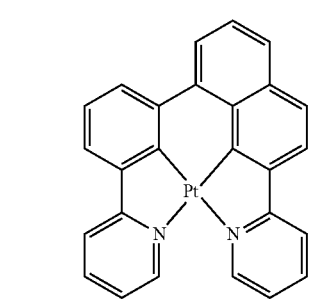
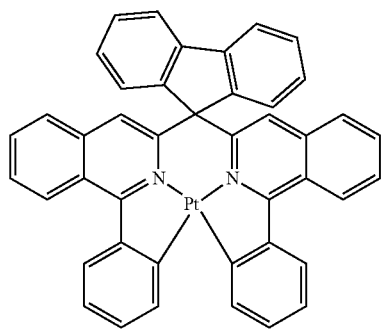
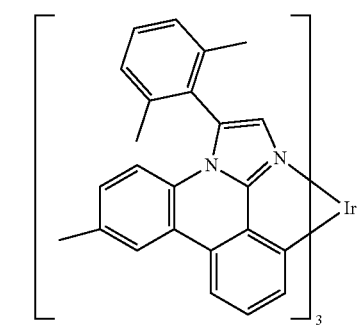

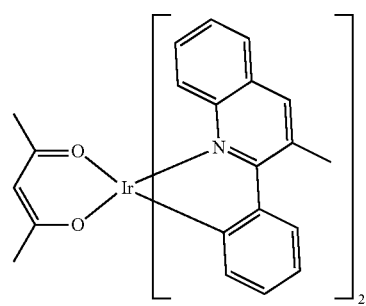
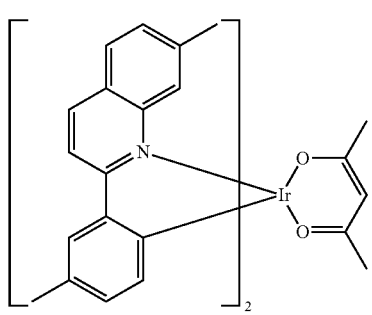
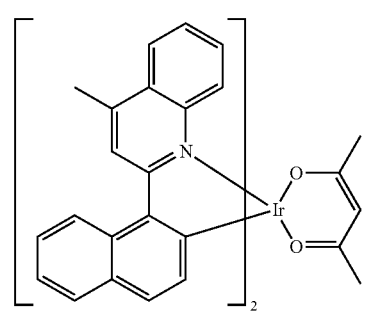
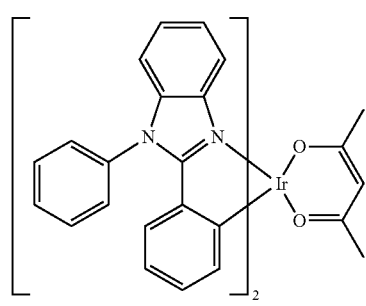
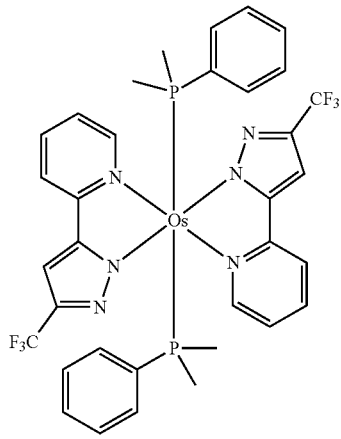
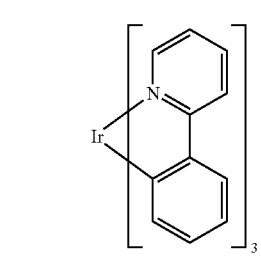
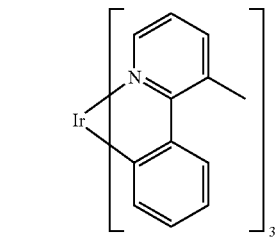
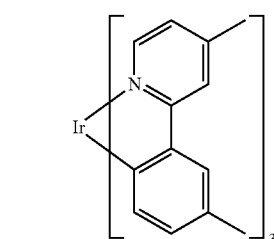
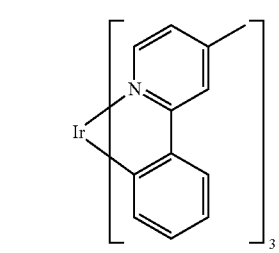

127
-continued
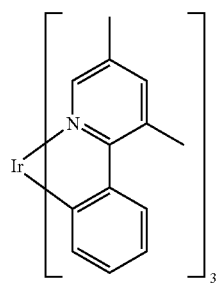
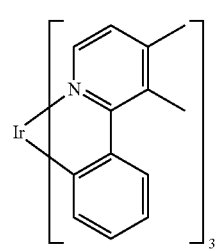
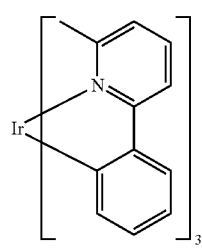
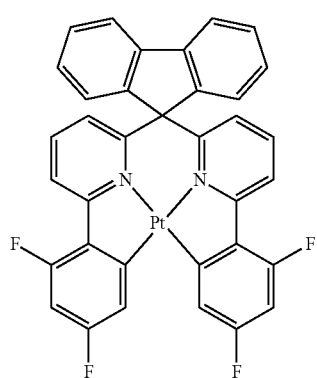
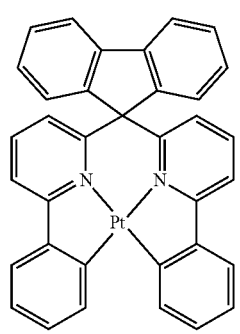
128
-continued
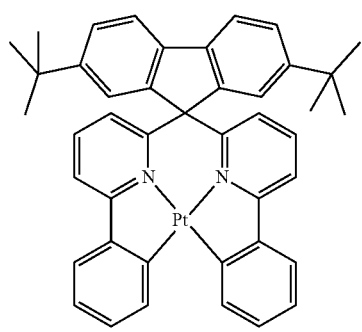
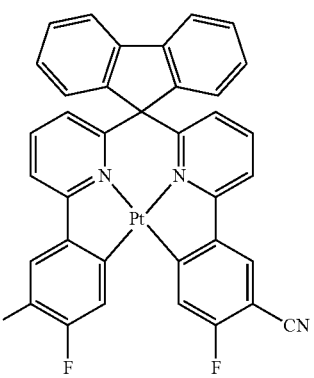
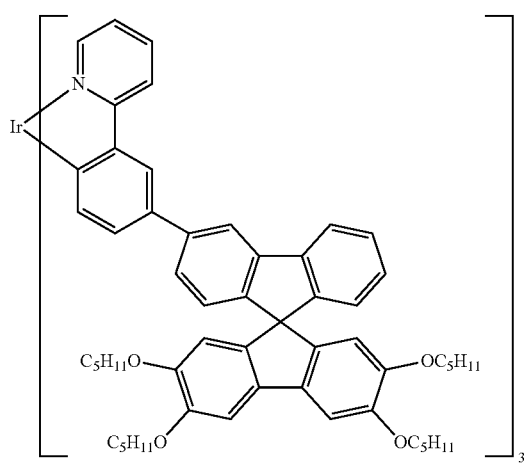
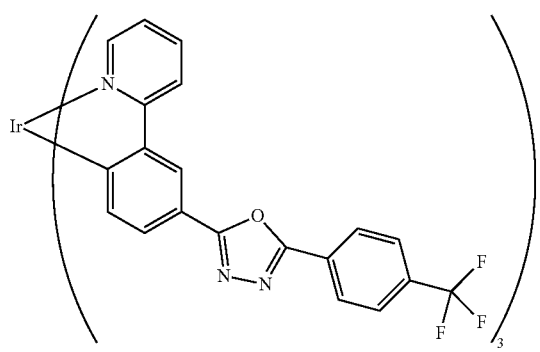

129
-continued
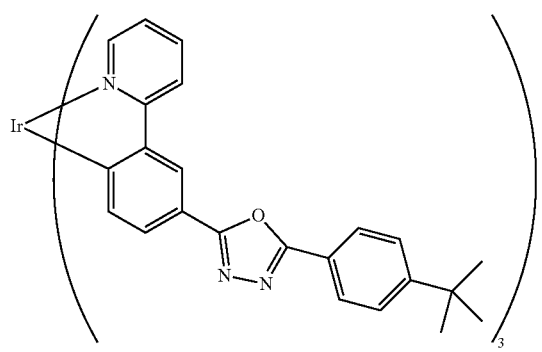
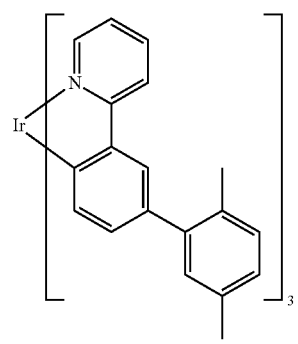
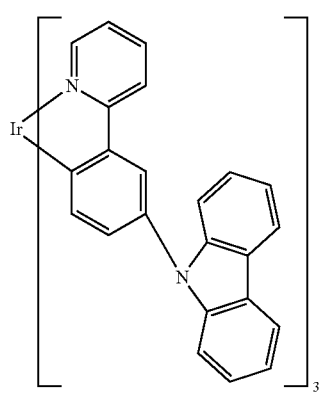
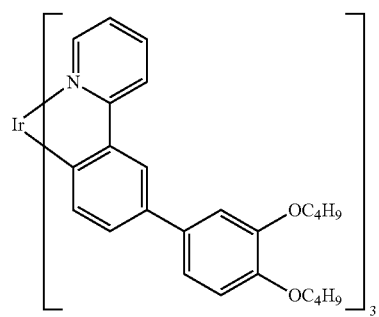
130
-continued
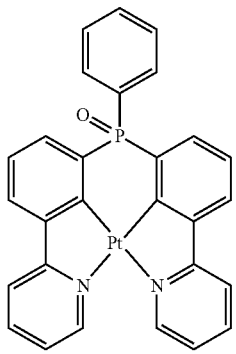
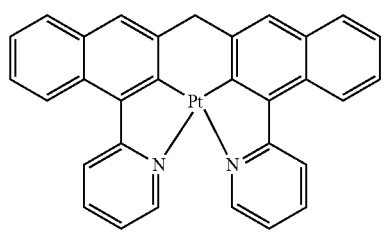
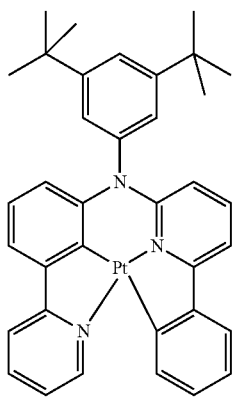
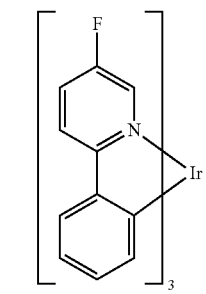
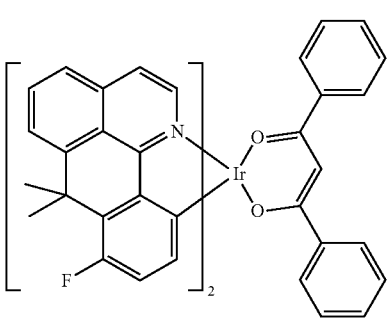

131
-continued
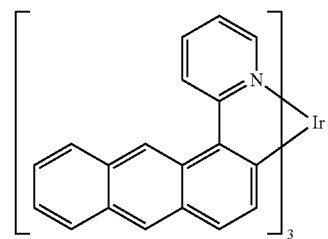
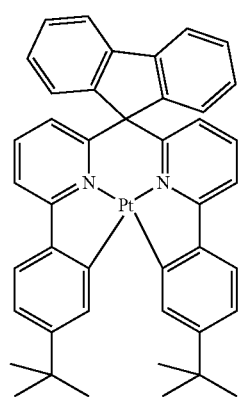
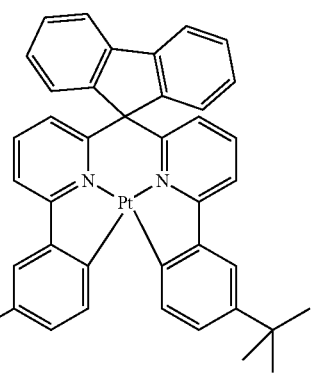
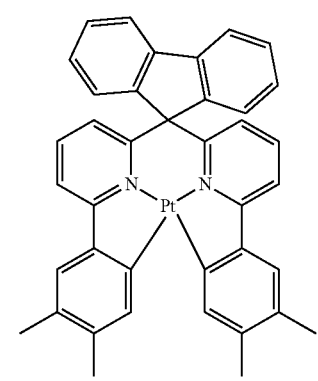
132
-continued
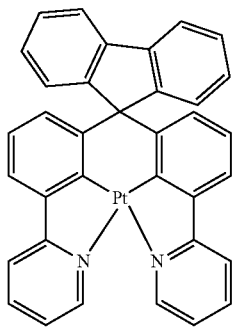
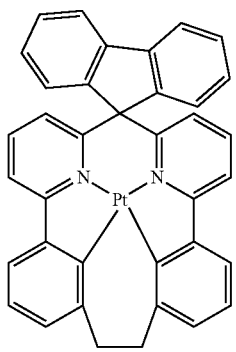
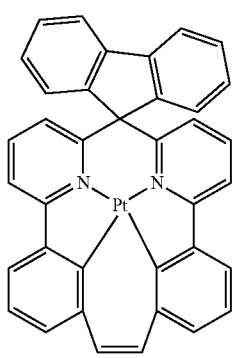
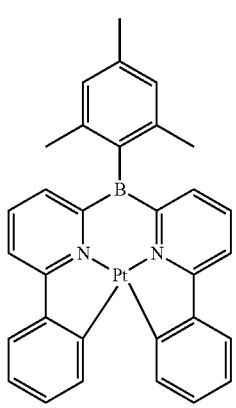

| 133 -continued | 134 -continued |
|---|---|
| 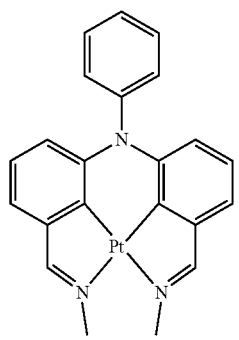 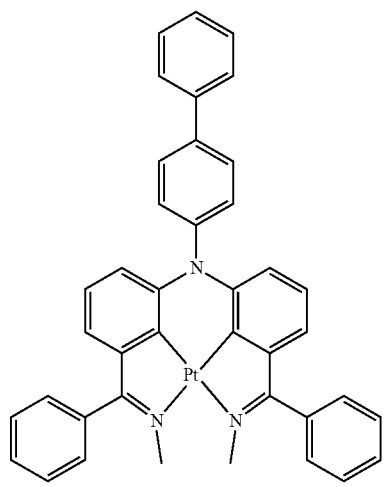 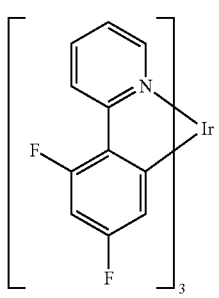 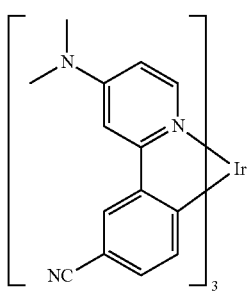 | 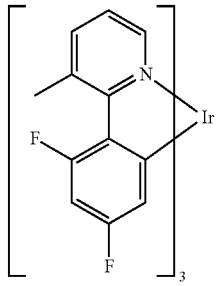 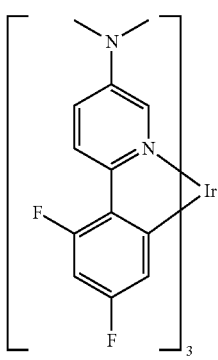 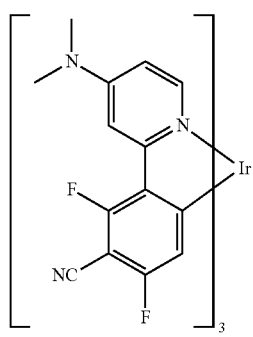 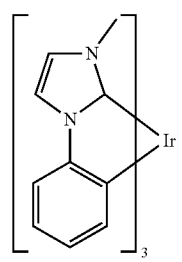 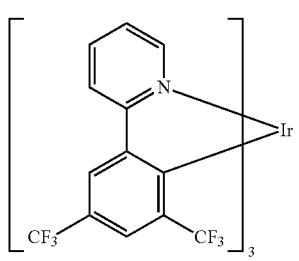 |

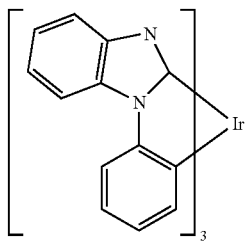
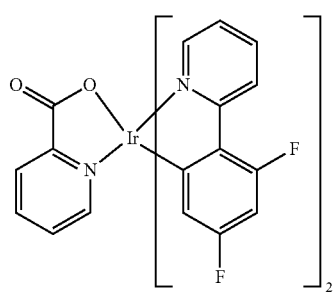
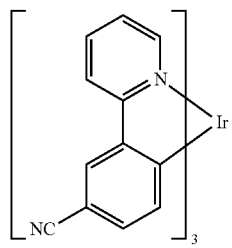
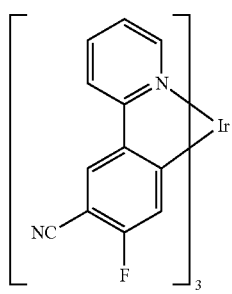
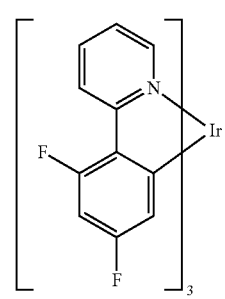
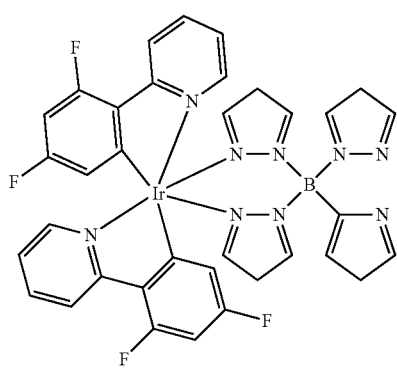
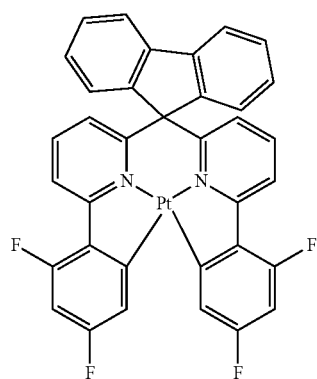
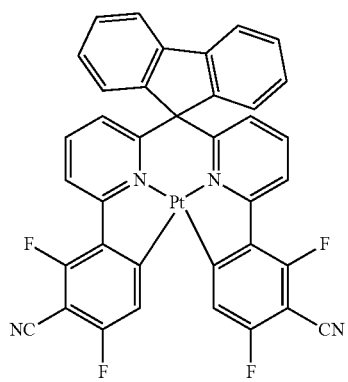
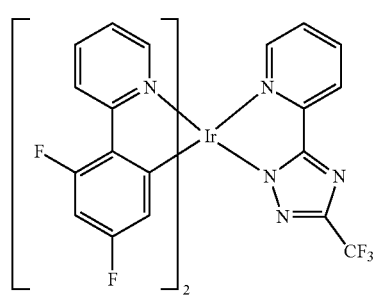

137
-continued
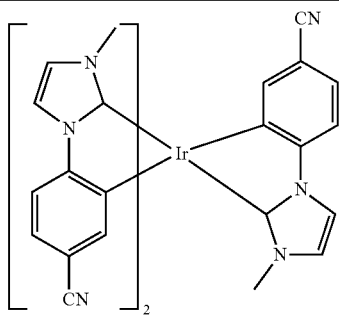
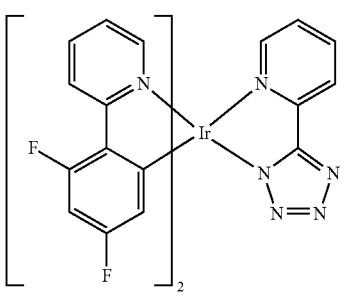
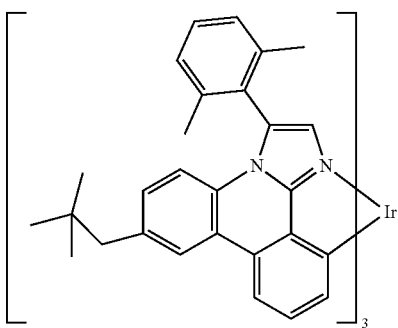
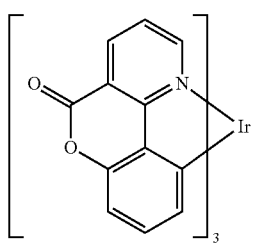
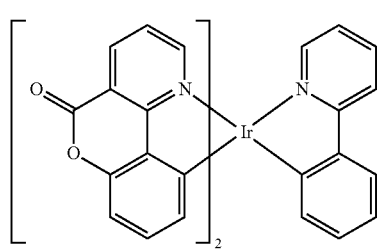
138
-continued
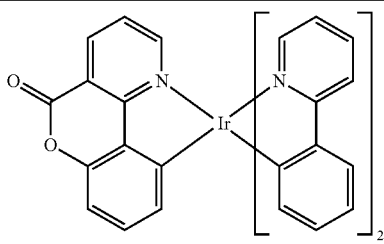
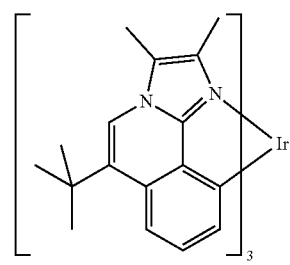
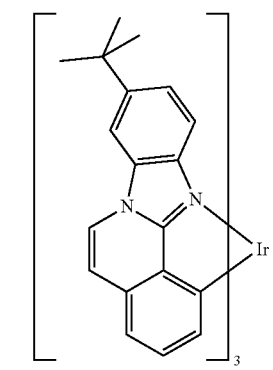
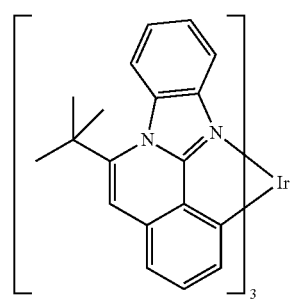
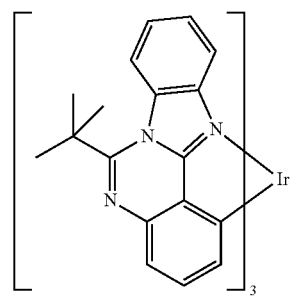

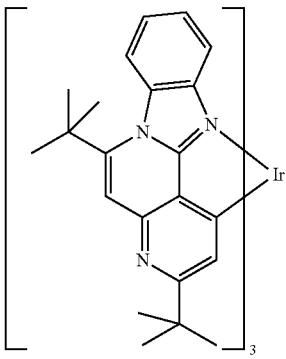

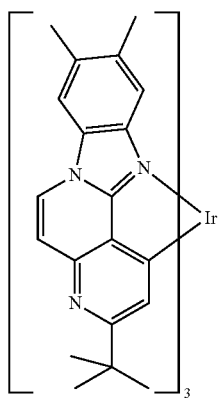

In a preferred embodiment of the invention, the compounds of the general formula (1) are employed as hole-transport material. The compounds are then preferably employed in a hole-transport layer, an electron-blocking layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer. If the compounds of the formula (1) are used as hole-transport material or as hole-injection material, it may be preferred for them to be doped with electron-acceptor compounds (p-doping), for example with $F_4$-TCNQ, $F_6$-TNAP or compounds as described in EP 1476881 or EP 1596445. In a further preferred embodiment of the invention, a compound of the formula (1) is used as hole-transport material in combination with a hexaazatriphenylene derivative, as described in US 2007/0092755. The hexaazatriphenylene derivative here is particularly preferably employed in a separate layer.

If the compounds of the general formula (1) are employed as hole-transport material in a hole-transport layer, the compound may be employed as pure material, i.e. in a proportion of 100%, in the hole-transport layer, or it may be employed in combination with one or more further compounds in the hole-transport layer.

In a further embodiment of the present invention, the compounds of the general formula (1) are employed as emitting materials. For this purpose, the compounds are preferably employed in an emission layer. Besides at least one of the compounds of the general formula (1), the emission layer furthermore comprises at least one host material. The person skilled in the art will be able to make a selection from the known host materials without difficulties and without being inventive.

In a further embodiment of the present invention, the compounds of the general formula (1) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the general formula (1) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more dopants, preferably one or more phosphorescent dopants. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

Preferred phosphorescent dopants for use in mixed-matrix systems are the phosphorescent dopants shown in the above table.

p-Dopants herein are taken to mean oxidants, i.e. electron acceptors. Preferred examples of p-dopants are $F_4$-TCNQ, F$_6$-TNAP, NDP-2 (Novaled), NDP-9 (Novaled), quinones (for example EP 1538684 A1, WO 2006/081780 A1, WO 2009/003455 A1, WO 2010/097433 A1), radialenes (for example EP 1988587 A1, US 2010/102709 A1, EP 2180029 A1, WO 2011/131185 A1, WO 2011134458 A1, US 2012/223296 A1), S-containing transition-metal complexes (for example WO 2007/134873 A1, WO 2008/061517 A2, WO 2008/061518 A2, DE 102008051737 A1, WO 2009/089821 A1, US 2010/096600 A1), bisimidazoles (for example WO 2008/138580 A1), phthalocyanines (for example WO 2008/058525 A2), bora-tetraazapentalenes (for example WO 2007/115540 A1) fullerenes (for example DE 102010046040 A1) and main-group halides (for example WO 2008/128519 A2).

The materials preferably employed in the relevant functions in the devices according to the invention are indicated below.

Preferred fluorescent dopants are selected from the class of the aryl-amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracen-amines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Suitable matrix materials, preferably for fluorescent dopants, besides the compounds according to the invention, are materials from various classes of substance. Preferred matrix materials are selected from the classes of the oligoarylenes (for example 2,2',7,7-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benz-anthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenyl-enes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlq.

Suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magne-sium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, Li$_2$O, BaF$_2$, MgO, NaF, CsF, Cs$_2$CO$_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the general formula (1) can be employed in displays, as light sources in lighting applications and as light sources in medical and/or cosmetic applications (for example light therapy).

Devices comprising the compounds of the general formula (1) can be employed in a very versatile manner. Thus, for example, electroluminescent devices comprising one or more compounds of the general formula (1) can be employed in displays for televisions, mobile telephones, computers and cameras. However, the devices can also be used in lighting applications. Furthermore, electroluminescent devices, for example in OLEDs or OLECs, comprising at least one of the compounds of the general formula (1) can be used for phototherapy in medicine or cosmetics. Thus, a large number of diseases (psoriasis, atopic dermatitis, inflammation, acne, skin cancer, etc.) can be treated or skin wrinkling, skin reddening and skin ageing can be prevented or reduced. Furthermore, the light-emitting devices can be utilised in order to keep drinks, meals or foods fresh or in order to sterilise equipment (for example medical equipment).

The compounds according to the invention and the organic electroluminescent devices according to the invention are distinguished by the following surprising advantages over the prior art:

1. The compounds according to the invention are very suitable for use in a hole-transport layer or a hole-injection layer in electronic devices, such as, for example, in organic electroluminescent devices, in particular owing to their high hole mobility. In particular, they are also suitable here for use in a layer which is directly adjacent to a phosphorescent emitting layer, since the compounds according to the invention do not extinguish the luminescence.

2. The compounds according to the invention, employed as matrix material for fluorescent or phosphorescent emitters, result in very high efficiencies and in long lifetimes. This applies, in particular, if the compounds are employed as matrix material together with a further matrix material and a phosphorescent emitter.

3. The compounds according to the invention, employed in organic electroluminescent devices, result in high efficiencies and in steep cur-rent/voltage curves with low use and operating voltages.

4. The use of the compounds according to the invention in electronic devices, in particular employed as hole-transport or hole-injection material, results in high efficiencies, low operating voltages and in long lifetimes.

5. The compounds according to the invention have a relatively low sublimation temperature, high temperature stability and high oxidation stability and a high glass-transition temperature, which is advantageous both for the processability, for example from solution or from the gas phase, and also for use in electronic devices.

6. The compounds according to the invention have high oxidation stability, which has, in particular, a positive effect on the handling of these compounds and on the shelf life for solutions.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies in particular to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention currently claimed.

The teaching on technical action disclosed with the present invention can be abstracted and combined with other examples.

The invention is explained in greater detail by the following examples, without wishing to restrict it thereby.

EXAMPLES

Example 1

Synthesis of biphenyl-4-yl-(9,9-dimethyl-9H-fluoren-2-yl)-[4-(9-methyl-9-phenyl-9H-fluoren-4-yl)phenyl]amine (1-1) and Compounds (1-2) to (1-7)

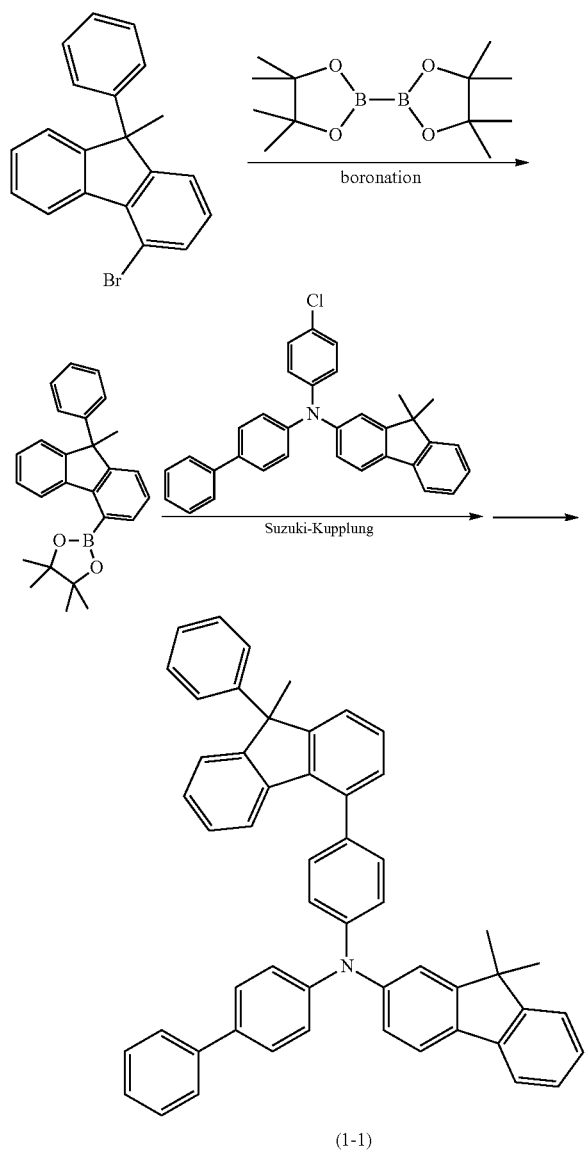

(1-1)

Starting material:
4-Bromo-9-methyl-9-diphenyl-9H-fluorene 50 g (157 mmol) of 2,2'-dibromobiphenyl are dissolved in 500 ml of dried THF in a flask which has been dried by heating. The reaction mixture is cooled to –78° C. At this temperature, 63 ml of a 2.5 M solution of n-BuLi in hexane (157 mmol) are slowly added dropwise (duration: about 1 hour). The batch is stirred at –70° C. for a further 1 h. 18.9 g of acetophenone (119 mmol) are subsequently dissolved in 100 ml of THF and added dropwise at –70° C. When the addition is complete, the reaction mixture is slowly warmed to room temperature, quenched using $NH_4Cl$ and subsequently evaporated in a rotary evaporator. 510 ml of acetic acid are carefully added to the evaporated solution, and 100 ml of fuming HCl are subsequently added. The batch is heated to 75° C. and kept at this temperature for 4 h. A white solid precipitates out during this time. The batch is then cooled to room temperature, and the solid which has precipitated out is filtered off with suction and rinsed with methanol. The residue is dried at 40° C. in vacuo. The yield is 48 g (121 mmol) (77% of theory).

4,4,5,5-Tetramethyl-2-(9-methyl-9-phenyl-9H-fluoren-4-yl)-1,3,2-dioxa-borolane 50 g (125 mmol) of the 4-bromofluorene derivative, 38.3 g (150 mmol) of bis(pinacolato)diborane and 35 g (378 mmol) of potassium acetate are suspended in 700 ml of dioxane. 3.08 g (3.78 mmol) of 1,1-bis(diphenyl-phosphino)ferrocenepalladium(II) dichloride complex with DCM are added to this suspension. The reaction mixture is heated under reflux for 14 h. After cooling, the organic phase is separated off, washed three times with 400 ml of water and subsequently evaporated to dryness. The residue is recrystallised from toluene (42 g, 75% yield).

The following compounds are prepared analogously:

| Starting material | Product | Yield |
|---|---|---|
| CAS: 125053-54-2 | | 83% |
| CAS: 942615-32-9 | | 78% |
| CAS: 1190360-23-6 | | 88% |

147

-continued

| Starting material | Product | Yield |
|---|---|---|
| 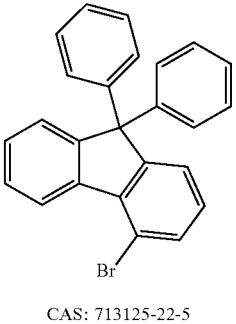<br>CAS: 713125-22-5 | 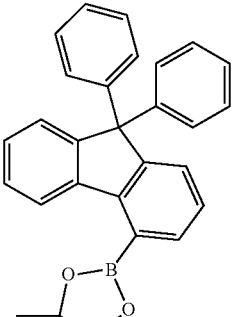 | 91% |

Intermediate: Biphenyl-4-yl-(4-chlorophenyl)-(9,9-dimethyl-9H-fluoren-2-yl)amine

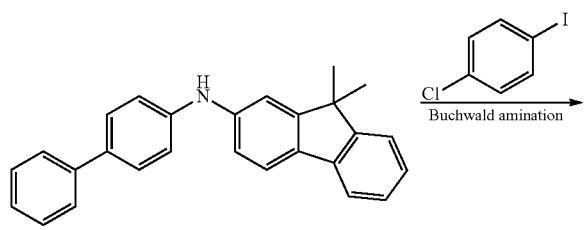

148

-continued

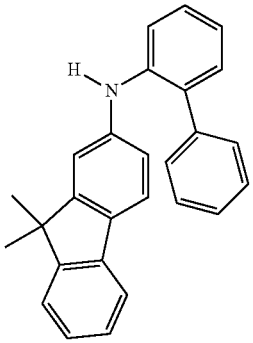 [SMILES: CC1(C)c2ccccc2-c2ccc(Nc3ccccc3-c3ccccc3)cc21]

40 g of biphenyl-4-yl-(9,9-dimethyl-9H-fluoren-2-yl)amine (111 mmol) and 26.4 g of 4-chloroiodobenzene (111 mmol) are dissolved in 700 ml of toluene. The solution is degassed and saturated with $N_2$. 4.43 ml (4.42 mmol) of a 1 M tri-tert-butylphosphine solution and 0.5 g (2.21 mmol) of palladium(II) acetate are then added, and 15.9 g of sodium tert-butoxide (186 mmol) are subsequently added. The reaction mixture is heated at the boil under a protective atmosphere for 12 h. The mixture is subsequently partitioned between toluene and water, and the organic phase is washed three times with water and dried over $Na_2SO_4$ and evaporated in a rotary evaporator. After filtration of the crude product through silica gel with toluene, the residue which remains is recrystallised from heptane/toluene. The yield is 44.5 g (85% of theory).

The following compounds are prepared analogously:

| Starting material 1 | Starting material 2 | Product | Yield |
|---|---|---|---|
| 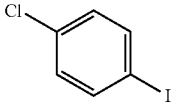 | 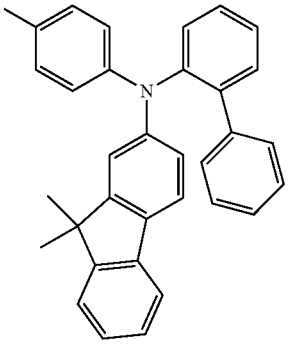 | 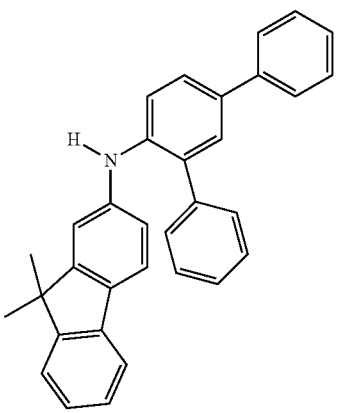 [SMILES: CC1(C)c2ccccc2-c2ccc(Nc3ccc(-c4ccccc4)cc3-c3ccccc3)cc21] | 78% |
| 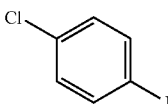 | 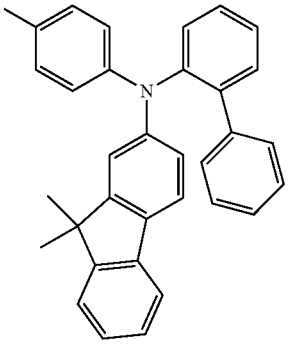 | 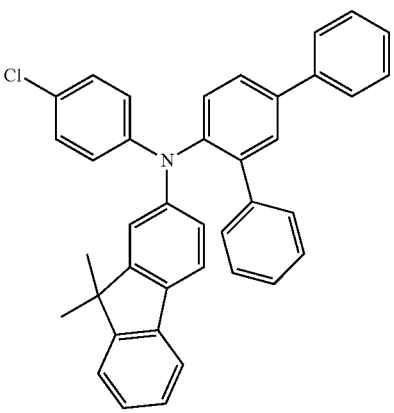 [SMILES: CC1(C)c2ccccc2-c2ccc(N(c3ccc(Cl)cc3)c3ccc(-c4ccccc4)cc3-c3ccccc3)cc21] | 80% |

-continued

| Starting material 1 | Starting material 2 | Product | Yield |
|---|---|---|---|
| N-([1,1'-biphenyl]-4-yl)-9,9-dimethyl-9H-fluoren-2-amine | 1-chloro-3-iodobenzene | N-([1,1'-biphenyl]-4-yl)-N-(3-chlorophenyl)-9,9-dimethyl-9H-fluoren-2-amine | 81% |
| N-([1,1'-biphenyl]-4-yl)-9,9-dimethyl-9H-fluoren-2-amine | 1-chloro-2-iodobenzene | N-([1,1'-biphenyl]-4-yl)-N-(2-chlorophenyl)-9,9-dimethyl-9H-fluoren-2-amine | 81% |
| N-(dibenzo[b,d]thiophen-4-yl)-9,9-dimethyl-9H-fluoren-2-amine | 1-chloro-4-iodobenzene | N-(4-chlorophenyl)-N-(dibenzo[b,d]thiophen-4-yl)-9,9-dimethyl-9H-fluoren-2-amine | 92% |

-continued

| Starting material 1 | Starting material 2 | Product | Yield |
|---|---|---|---|
| | | | 75% |
| | | | 78% |
| | | | 81% |

-continued

| Starting material 1 | Starting material 2 | Product | Yield |
|---|---|---|---|
| | | | 75% |
| | | | 86% |
| | | | 88% |

| Starting material 1 | Starting material 2 | Product | Yield |
|---|---|---|---|
| | | | 73% |

Synthesis of Compound (1-1)

20 g (44 mmol) of 4-fluorenepinacoloboronic ester derivative, 20.8 g (44 mmol) of the chlorine derivative and 13.4 g of caesium fluoride (88.1 mmol) are suspended in 265 ml of dioxane. 3.9 g (5.28 mmol) of bis-(tricyclohexylphosphine)palladium dichloride are added to this suspension, and the reaction mixture is heated under reflux for 18 h. After cooling, the organic phase is separated off, filtered through silica gel, washed three times with 100 ml of water and subsequently evaporated to dryness. After filtration of the crude product through silica gel with toluene, the residue which remains is recrystallised from heptane/toluene and finally sublimed in a high vacuum. The purity is 99.9%. The yield is 26.5 g (80% of theory).

Synthesis of compounds (1-2) to (1-15)

The following compounds (1-2) to (1-15) are also prepared analogously to the synthesis of compound (1-1) described in Example 1.

| Starting material 1 | Starting material 2 | Product | Yield |
|---|---|---|---|
| | | | 78% |

(1-2)

-continued
| Starting material 1 | Starting material 2 | Product | Yield |
|---|---|---|---|
| 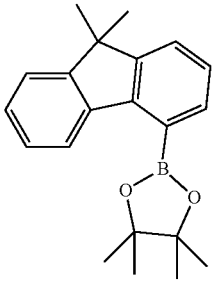 [SMILES: CC1(C)c2ccccc2-c2c(B3OC(C)(C)C(C)(C)O3)cccc21] | 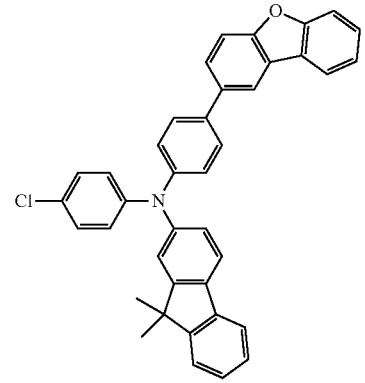 [SMILES: CC1(C)c2ccccc2-c2ccc(N(c3ccc(Cl)cc3)c3ccc(-c4ccc5oc6ccccc6c5c4)cc3)cc21] | 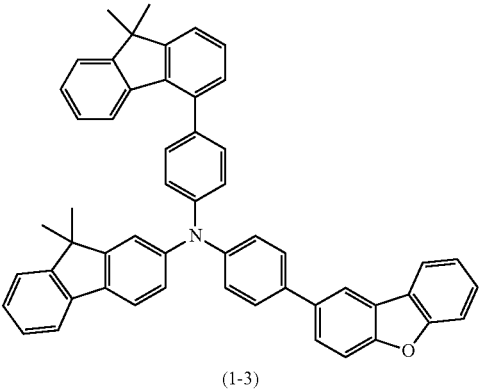 [SMILES: CC1(C)c2ccccc2-c2ccc(N(c3ccc(-c4ccc5oc6ccccc6c5c4)cc3)c3ccc(-c4cccc5c4-c4ccccc4C5(C)C)cc3)cc21](1-3) | 70% |
| 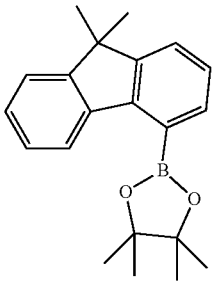 [SMILES: CC1(C)c2ccccc2-c2c(B3OC(C)(C)C(C)(C)O3)cccc21] | 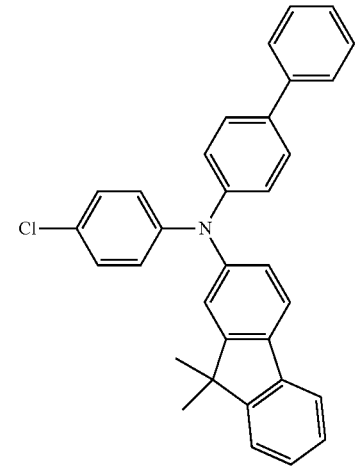 [SMILES: CC1(C)c2ccccc2-c2ccc(N(c3ccc(Cl)cc3)c3ccc(-c4ccccc4)cc3)cc21] | 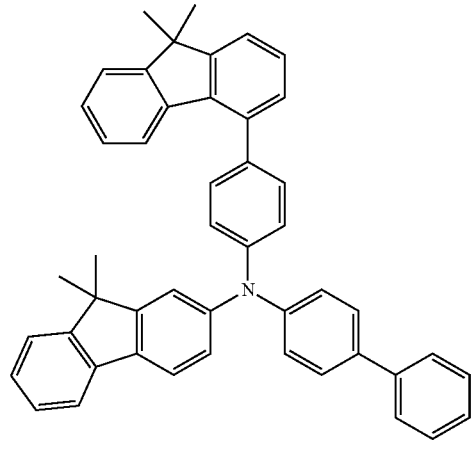(1-4) | 78% |
| 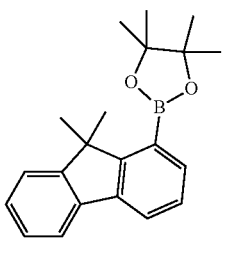 [SMILES: CC1(C)c2ccccc2-c2cccc(B3OC(C)(C)C(C)(C)O3)c21] | 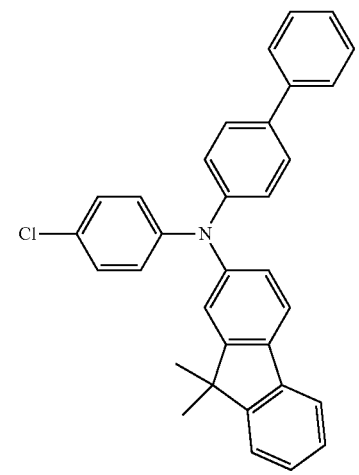 [SMILES: CC1(C)c2ccccc2-c2ccc(N(c3ccc(Cl)cc3)c3ccc(-c4ccccc4)cc3)cc21] | 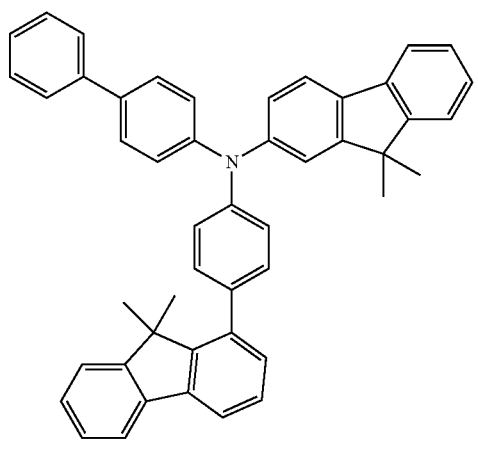(1-5) | 80% |

-continued
| Starting material 1 | Starting material 2 | Product | Yield |
|---|---|---|---|
| 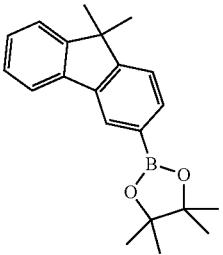 [SMILES: CC1(C)c2ccccc2-c2cc(B3OC(C)(C)C(C)(C)O3)ccc21] | 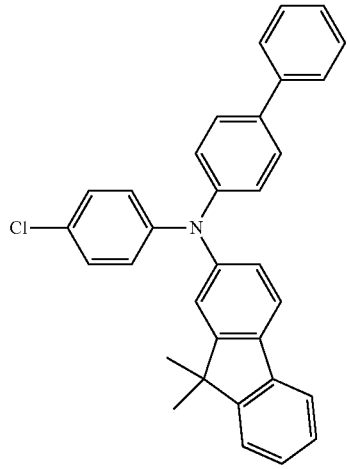 [SMILES: CC1(C)c2ccccc2-c2ccc(N(c3ccc(Cl)cc3)c3ccc(-c4ccccc4)cc3)cc21] | 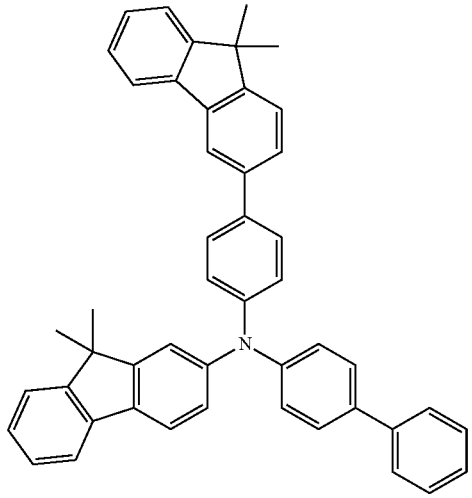<br>(1-6) | 75% |
| 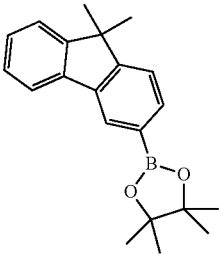 [SMILES: CC1(C)c2ccccc2-c2cc(B3OC(C)(C)C(C)(C)O3)ccc21] | 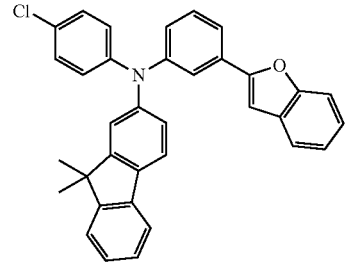 [SMILES: CC1(C)c2ccccc2-c2ccc(N(c3ccc(Cl)cc3)c3cccc(-c4cc5ccccc5o4)c3)cc21] | 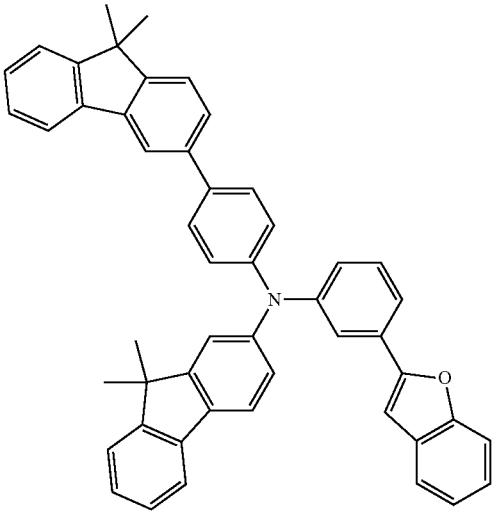<br>(1-7) | 68% |
| 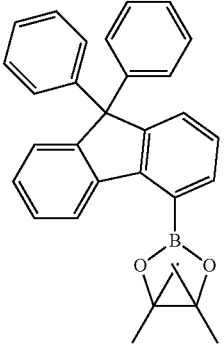 | 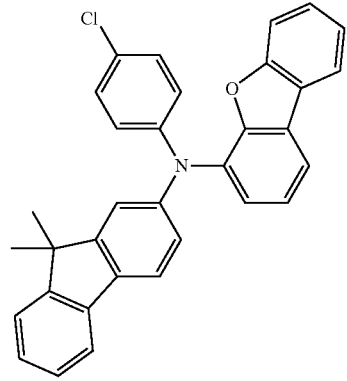 [SMILES: CC1(C)c2ccccc2-c2ccc(N(c3ccc(Cl)cc3)c3cccc4c3oc3ccccc34)cc21] | 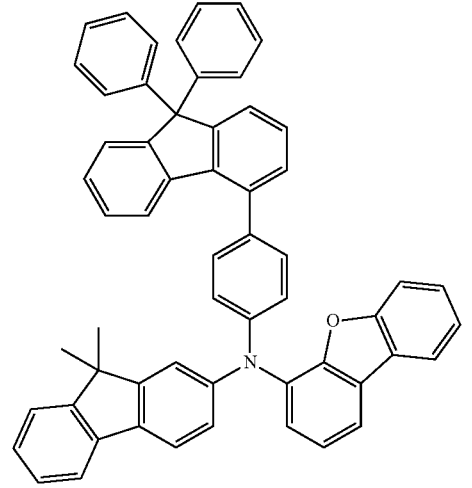<br>(1-8) | 80% |

-continued
| Starting material 1 | Starting material 2 | Product | Yield |
|---|---|---|---|
| 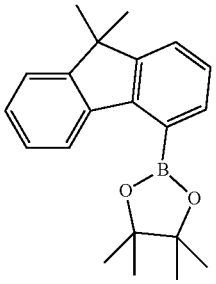 [SMILES: CC1(C)c2ccccc2-c2c(B3OC(C)(C)C(C)(C)O3)cccc21] | 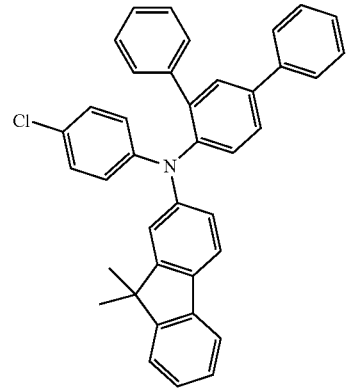 [SMILES: CC1(C)c2ccccc2-c2ccc(N(c3ccc(Cl)cc3)c3ccc(-c4ccccc4)cc3-c3ccccc3)cc21] | 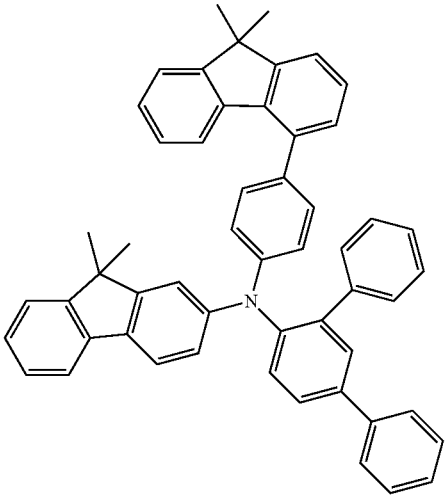 (1-9) | 75% |
| 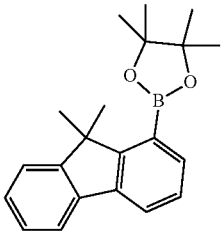 [SMILES: CC1(C)c2ccccc2-c2cccc(B3OC(C)(C)C(C)(C)O3)c21] | 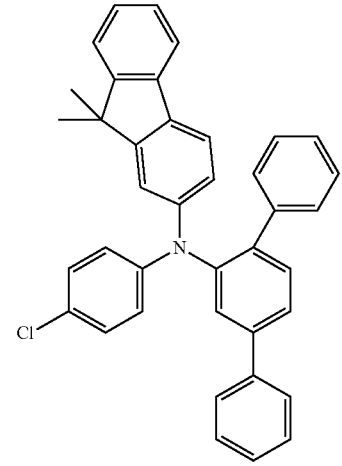 [SMILES: CC1(C)c2ccccc2-c2ccc(N(c3ccc(Cl)cc3)c3cc(-c4ccccc4)ccc3-c3ccccc3)cc21] | 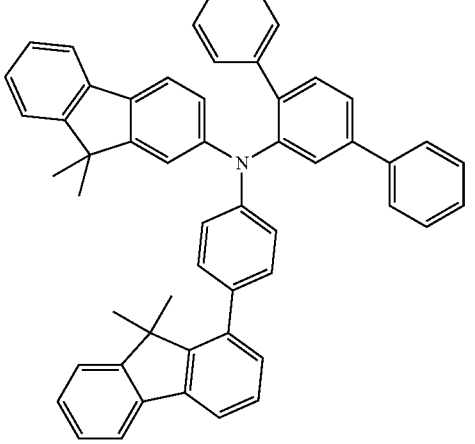 (1-10) | 73% |
| 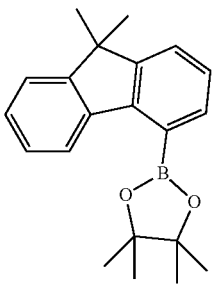 [SMILES: CC1(C)c2ccccc2-c2c(B3OC(C)(C)C(C)(C)O3)cccc21] | 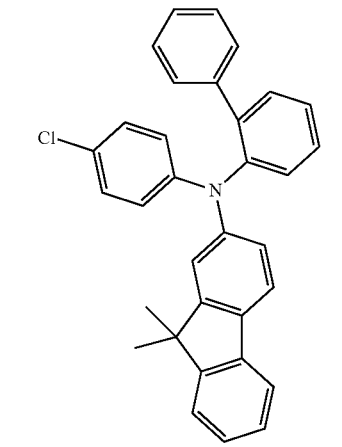 [SMILES: CC1(C)c2ccccc2-c2ccc(N(c3ccc(Cl)cc3)c3ccccc3-c3ccccc3)cc21] | 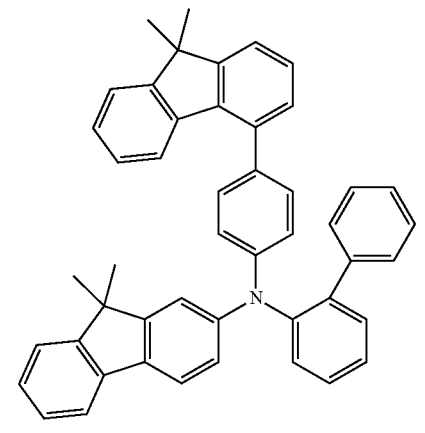 (1-11) | 80% |

-continued
| Starting material 1 | Starting material 2 | Product | Yield |
|---|---|---|---|
| | | | 77% |
| | | (1-12) | |
| | | | 85% |
| | | (1-13) | |
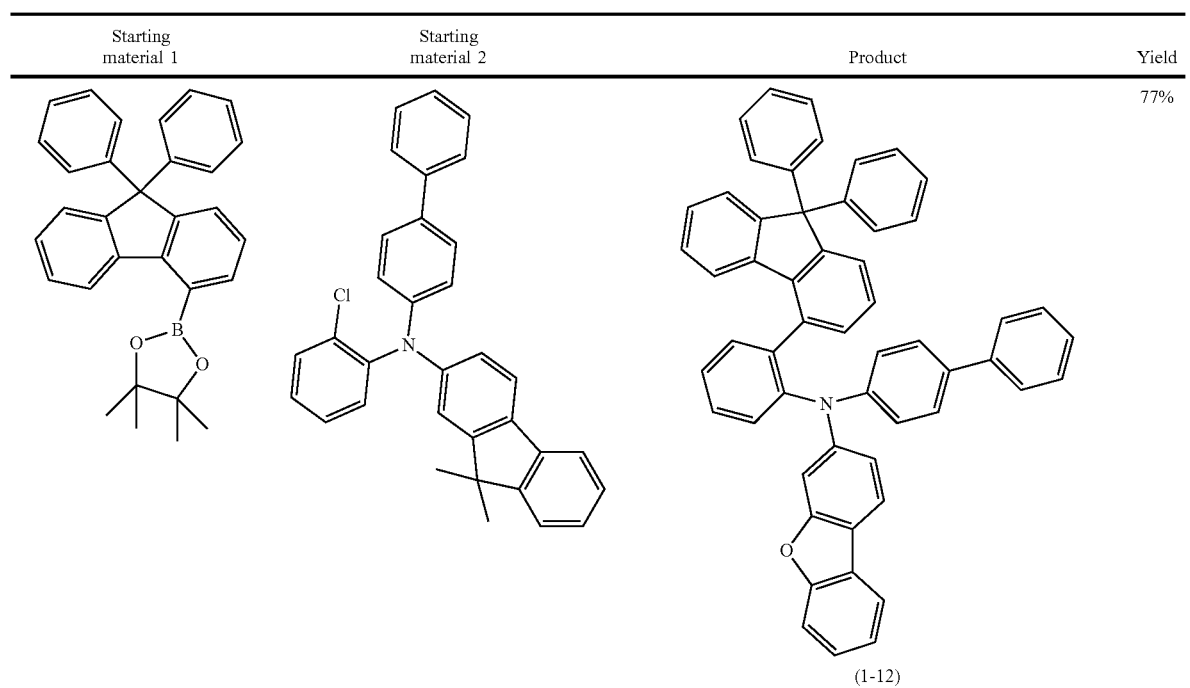
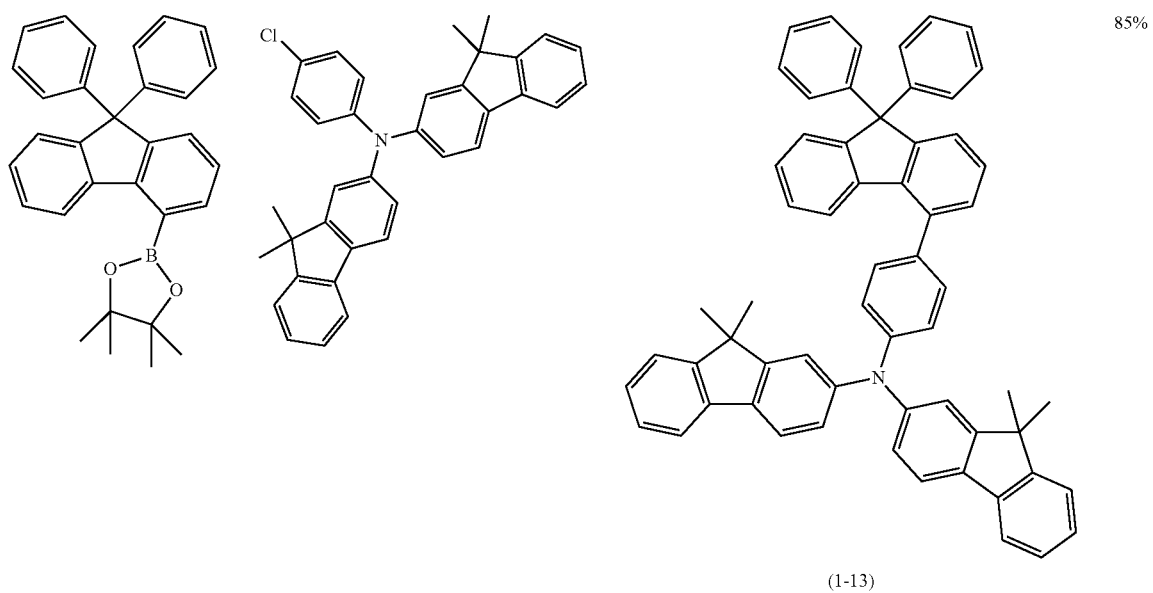

| Starting material 1 | Starting material 2 | Product | Yield |
|---|---|---|---|
| 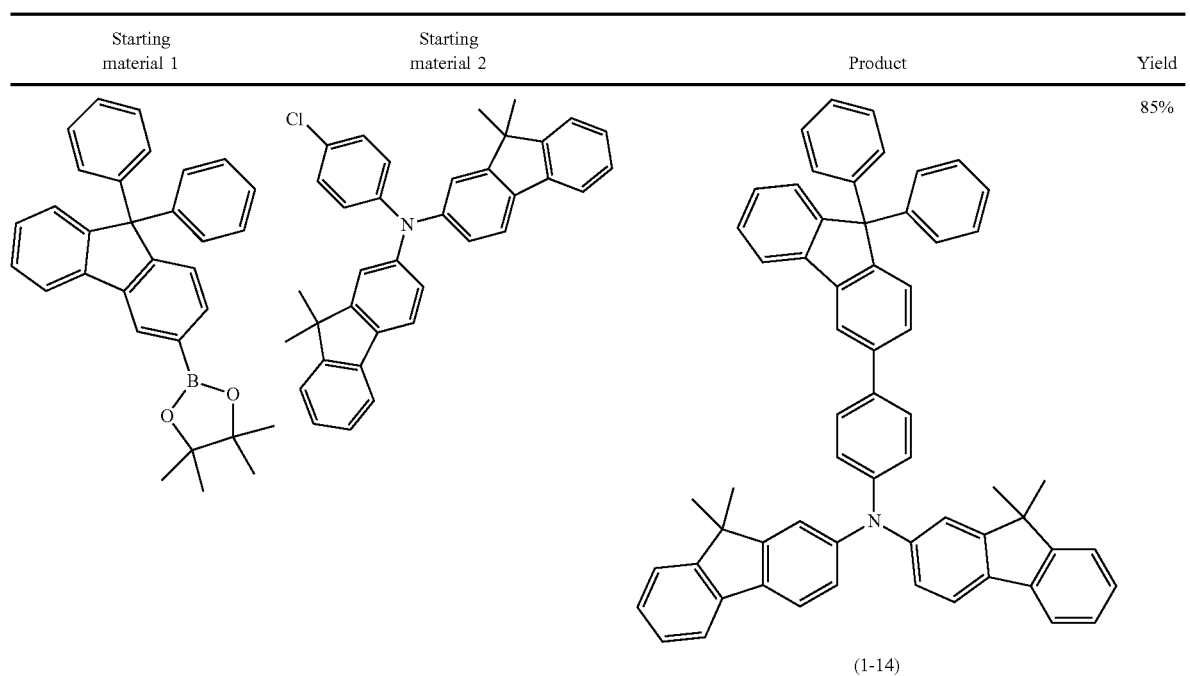 | | | 85% |
(1-14)
| | | | 88% |
|---|---|---|---|
| 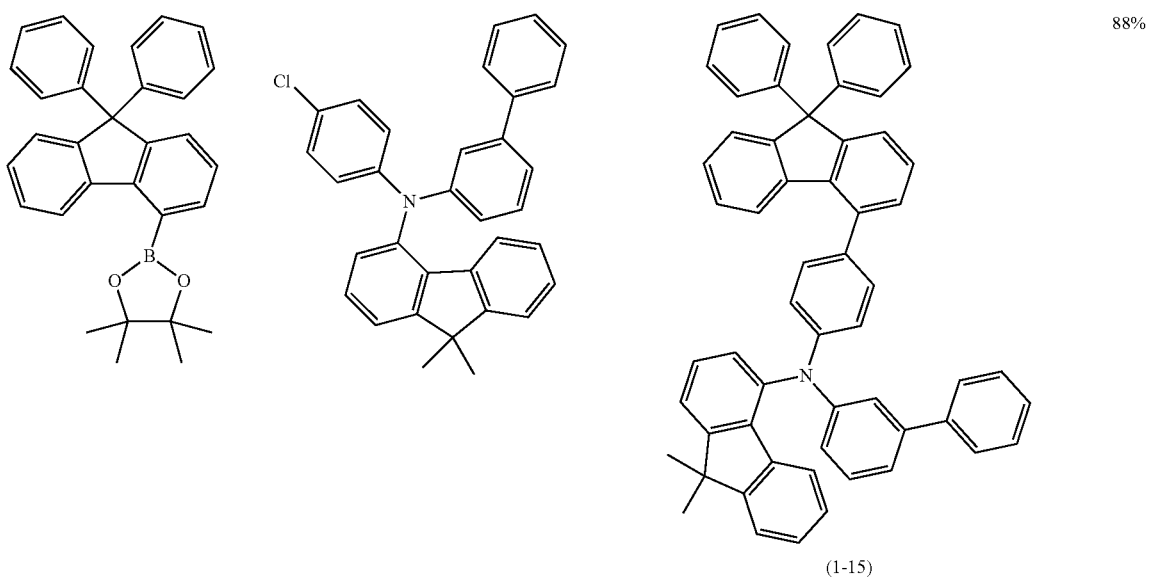 | | | |
(1-15)

-continued
| Starting material 1 | Starting material 2 | Product | Yield |
|---|---|---|---|
| 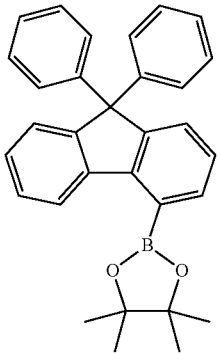 [SMILES: CC1(C)OB(c2cccc3c2-c2ccccc2C3(c2ccccc2)c2ccccc2)OC1(C)C] | 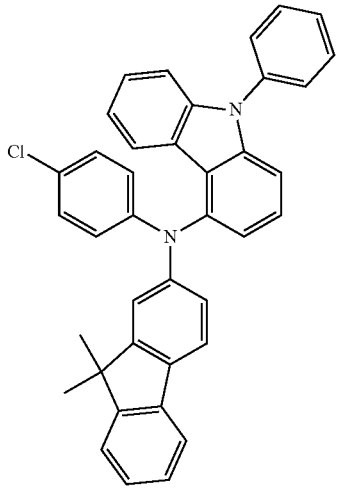 [SMILES: CC1(C)c2ccccc2-c2ccc(N(c3ccc(Cl)cc3)c3cccc4c3c3ccccc3n4-c3ccccc3)cc21] | 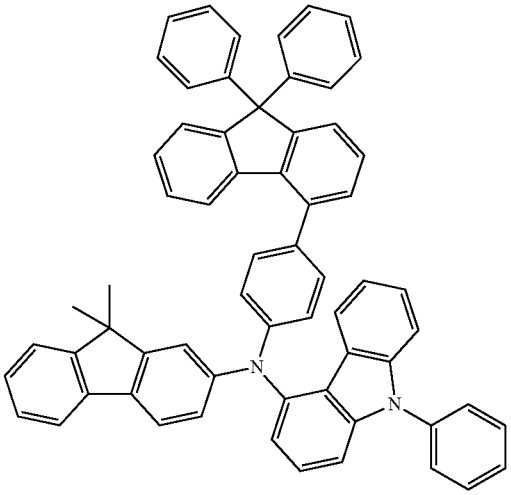 (1-16) | 75% |
| 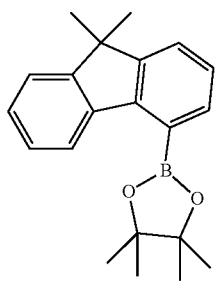 [SMILES: CC1(C)c2ccccc2-c2c(B3OC(C)(C)C(C)(C)O3)cccc21] | 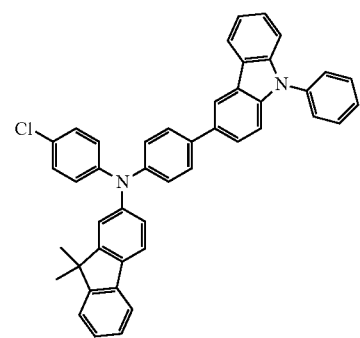 [SMILES: CC1(C)c2ccccc2-c2ccc(N(c3ccc(Cl)cc3)c3ccc(-c4ccc5c(c4)c4ccccc4n5-c4ccccc4)cc3)cc21] | 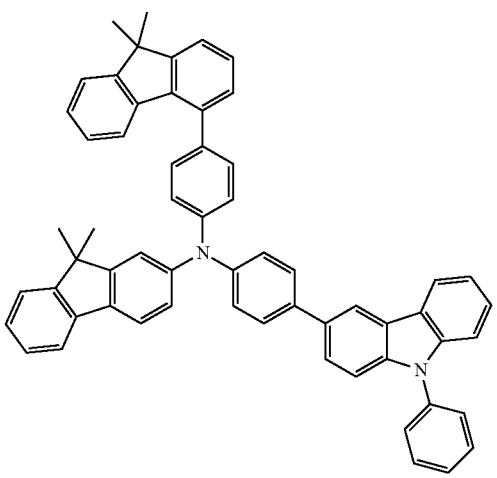 (1-17) | 80% |
Example 2
Synthesis of the Compound [4-(7-dibenzofuran-4-yl-9,9-diphenyl-9H-fluoren-4-yl)phenyl]-(9,9-dimethyl-9H-fluoren-2-yl)phenylamine (2-1) and Compounds (2-2) to (2-5)
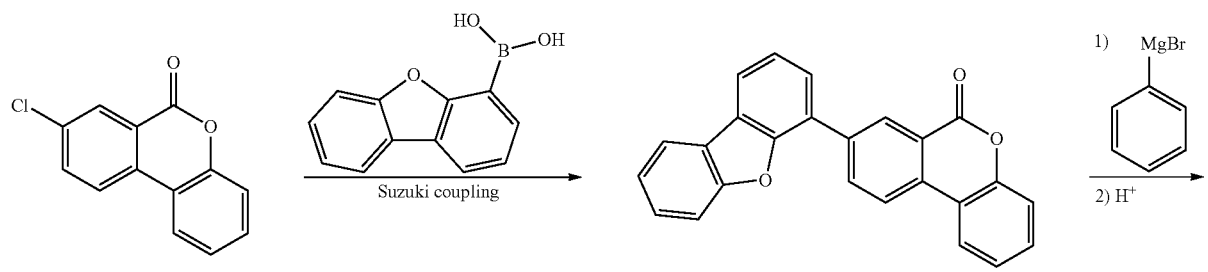

-continued

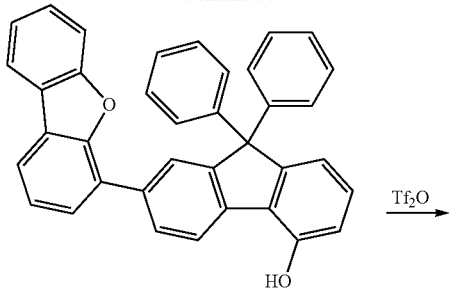

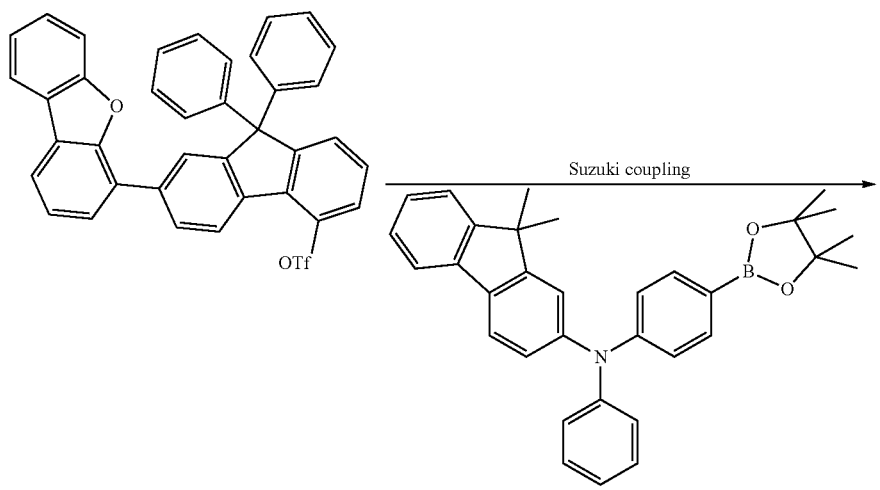

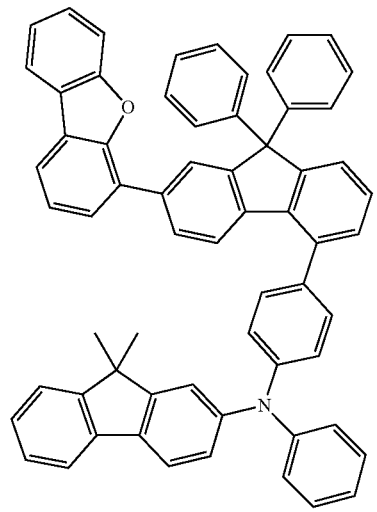

(2-1)

8-Dibenzofuran-4-ylbenzo[c]chromen-6-one 30.0 g (142 mmol) of dibenzofuran-4-boronic acid, 32 g (142 mmol) of 8-chlorobenzo[c]chromen-6-one (CAS: 742058-81-7) and 43 g of caesium fluoride (283 mmol) are suspended in 800 ml of dioxane. 12.5 g (17 mmol) of bis(tricyclohexylphosphine)palladium dichloride are added to this suspension, and the reaction mixture is heated under reflux for 18 h. After cooling, the organic phase is separated off, filtered through silica gel, washed three times with 100 ml of water and subsequently evaporated to dryness. After filtration of the crude product through silica gel with toluene, the residue which remains is recrystallised from heptane/toluene. The yield is 45 g (88% of theory).

The following compounds are prepared analogously:
| Starting material 1 | Starting material 2 | Product | Yield |
|---|---|---|---|
| 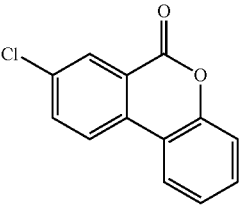 [SMILES: O=c1oc2ccccc2c2ccc(Cl)cc12] | 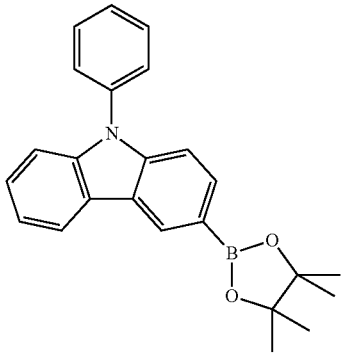 [SMILES: CC1(C)OB(c2ccc3c(c2)c2ccccc2n3-c2ccccc2)OC1(C)C] | 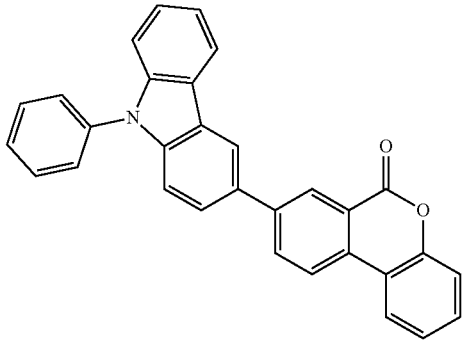 [SMILES: O=c1oc2ccccc2c2ccc(-c3ccc4c(c3)c3ccccc3n4-c3ccccc3)cc12] | 84% |
| 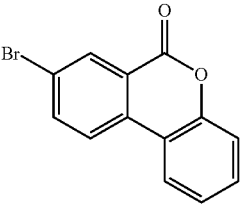<br>CAS: 1447543-95-4 | 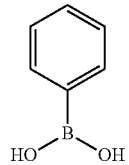 | 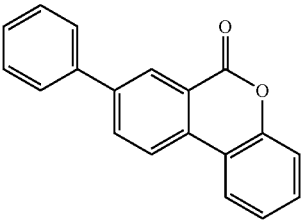 [SMILES: O=c1oc2ccccc2c2ccc(-c3ccccc3)cc12] | 90% |
| 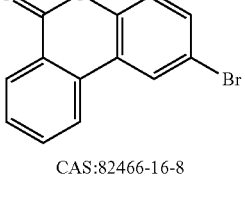<br>CAS:82466-16-8 | 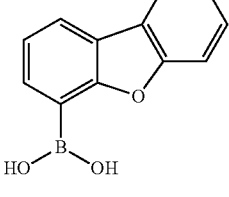 | 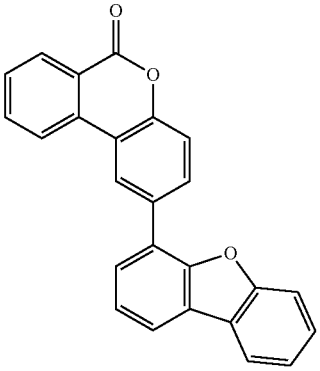 [SMILES: O=c1oc2ccc(-c3cccc4c3oc3ccccc34)cc2c2ccccc12] | 85% |
| 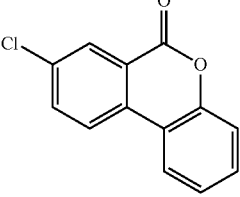 | 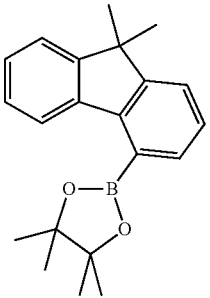 [SMILES: CC1(C)c2ccccc2-c2c(B3OC(C)(C)C(C)(C)O3)cccc21] | 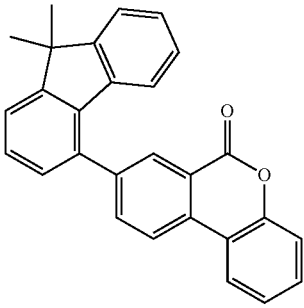 [SMILES: CC1(C)c2ccccc2-c2c(-c3ccc4c(c3)c(=O)oc3ccccc34)cccc21] | 76% |
| 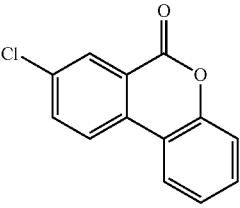 [SMILES: O=c1oc2ccccc2c2ccc(Cl)cc12] | 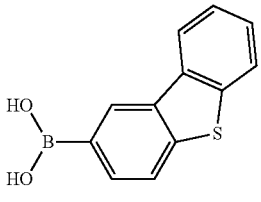 [SMILES: OB(O)c1ccc2sc3ccccc3c2c1] | 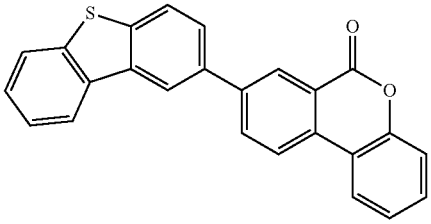 [SMILES: O=c1oc2ccccc2c2ccc(-c3ccc4sc5ccccc5c4c3)cc12] | 81% |

-continued

| Starting material 1 | Starting material 2 | Product | Yield |
|---|---|---|---|
| 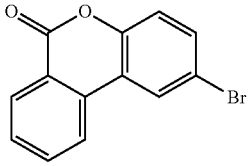 CAS:82466-16-8 | 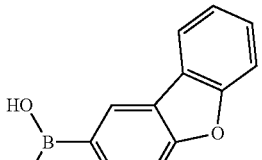 | 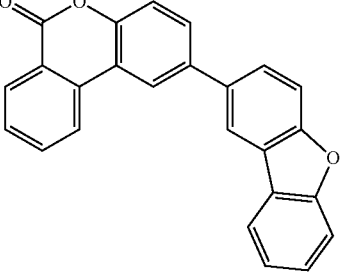 | 87% |

7-Dibenzofuran-4-yl-9,9-diphenyl-9H-fluoren-4-ol 25.4 g (70 mmol) of 8-dibenzofuran-4-ylbenzo[c]chromen-6-one are dissolved in 340 ml of dried THF in a flask which has been dried by heating. The solution is saturated with $N_2$. The clear solution is cooled to −10° C., and 70 ml (210 mmol) of a 3 M phenylmagnesium bromide solution are then added. The reaction mixture is slowly warmed to room temperature and then quenched using acetic anhydride (70 mmol). The mixture is subsequently partitioned between ethyl acetate and water, and the organic phase is washed three times with water, dried over $Na_2SO_4$ and evaporated in a rotary evaporator. 310 ml of acetic acid are carefully added to the evaporated solution, and 70 ml of fuming HCl are subsequently added. The batch is heated to 75° C. and kept at this temperature for 4 h. A white solid precipitates out during this time. The batch is then cooled to room temperature, and the precipitated solid is filtered off with suction and rinsed with methanol. The residue is dried at 40° C. in vacuo. Filtration of the crude product through silica gel with heptane/ethyl acetate 1:1 gives 26 g (75% of theory).

The following brominated compounds are prepared analogously:

| Starting material 1 | Starting material 2 | Product | Yield |
|---|---|---|---|
| 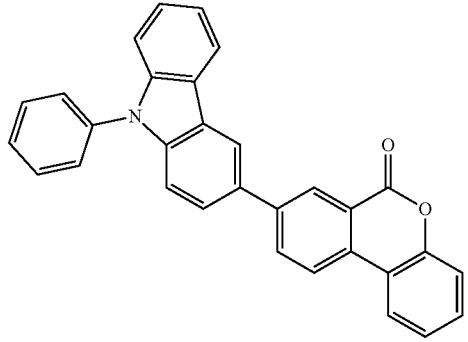 [SMILES: O=c1oc2ccccc2c2ccc(-c3ccc4c(c3)c3ccccc3n4-c3ccccc3)cc12] | 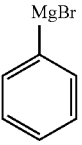 | 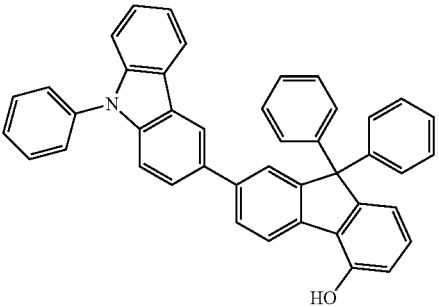 [SMILES: Oc1cccc2c1-c1ccc(-c3ccc4c(c3)c3ccccc3n4-c3ccccc3)cc1C2(c1ccccc1)c1ccccc1] | 72% |
| 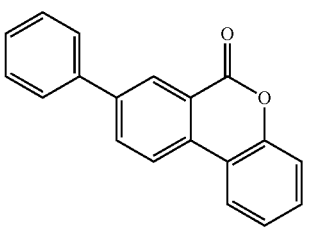 [SMILES: O=c1oc2ccccc2c2ccc(-c3ccccc3)cc12] | 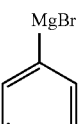 | 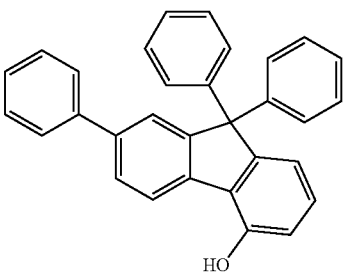 [SMILES: Oc1cccc2c1-c1ccc(-c3ccccc3)cc1C2(c1ccccc1)c1ccccc1] | 80% |

| Starting material 1 | Starting material 2 | Product | Yield |
|---|---|---|---|
| | MgBr-Ph | | 77% |
| | CH₃MgBr | | 72% |
| | MgBr-Ph | | 66% |
| | MgBr-Ph | | 74% |

(9,9-Dimethyl-9H-fluoren-2-yl)phenyl-[4-(4,4,5,5-tetramethyl-1,3,2-dioxaborolan-2-yl)phenyl]amine 32.1 g (81.1 mmol) of the 4-chlorophenylamine derivative, 20.6 g (81.1 mmol) of bis(pinacolato)diborane and 13.5 g (137.9 mmol) of potassium acetate are suspended in 600 ml of dioxane. 5.9 g (8.1 mmol) of bis(tricyclohexylphosphine)palladium(II) dichloride are added to this suspension. The reaction mixture is heated under reflux for 12 h. After cooling, the organic phase is separated off, washed three times with 200 ml of water and subsequently evaporated to dryness. The residue is recrystallised from toluene (28.8 g, 73% yield).

The following compounds are prepared analogously:

| Starting material 1 | Product | Yield |
|---|---|---|
| | | 79% |
| | | 80% |
| | | 72% |

| Starting material 1 | Product | Yield |
|---|---|---|
| | | 79% |
| | | 78% |

Compound [4-(7-dibenzofuran-4-yl-9,9-diphenyl-9H-fluoren-4-yl)-phenyl]-(9,9-dimethyl-9H-fluoren-2-yl)phenylamine (2-1)

25 g (50 mmol) of 7-dibenzofuran-4-yl-9,9-diphenyl-9H-fluoren-4-ol are dissolved in 300 ml of dried THF in a flask which has been dried by heating. The solution is saturated with $N_2$. The clear solution is cooled to 5° C., and 20 ml (150 mmol) of triethylamine, 122 mg of 4-dimethylaminopyridine and 8.65 ml of trifluoromethanesulfonic anhydride are then added. The reaction mixture is slowly warmed to room temperature. The reaction mixture is subsequently diluted with heptane, evaporated in a rotary evaporator and partitioned with water, and the organic phase is washed three times with water, dried over $Na_2SO_4$ and evaporated in a rotary evaporator. Filtration of the crude product through silica gel with heptane/ethyl acetate 1:1 gives 30 g of 7-dibenzofuran-4-yl-9,9-diphenyl-9H-fluoren-4-yl trifluoromethanesulfonate (98% of theory).

23.5 g (36.4 mmol) of 7-dibenzofuran-4-yl-9,9-diphenyl-9H-fluoren-4-yl trifluoromethanesulfonate, 18.61 g (38.2 mmol) of (9,9-dimethyl-9H-fluoren-2-yl)phenyl-[4-(4,4,5,5-tetramethyl-1,3,2-dioxaborolan-2-yl)phenyl]amine, 7.64 g of sodium metaborate tetrahydrate (54.6 mmol) and 53 μl of hydrazinium hydroxide (1.1 mmol) are suspended in 500 ml of THF and 200 ml of water. 1.02 g (1.46 mmol) of bis(triphenylphosphine)palladium dichloride are added to this suspension, and the reaction mixture is heated at 70° C. for 3 h. After cooling, the mixture is partitioned between ethyl acetate and water, and the organic phase is washed three times with water, dried over $Na_2SO_4$ and subsequently evaporated to dryness. After filtration of the crude product through silica gel with toluene, the residue which remains is recrystallised from heptane/toluene and subsequently sublimed. The yield is 18.4 g (60% of theory).

Synthesis of Compounds (2-2) to (2-6)

The following compounds are prepared analogously:

| Starting material 1 | Starting material 2 | Product | Yield |
|---|---|---|---|
| | | | 78% |
| | | (2-2) | |
| | | | 73% |
| | | (2-3) | |
| | | | 71% |
| | | (2-4) | |

| Starting material 1 | Starting material 2 | Product | Yield |
|---|---|---|---|
| 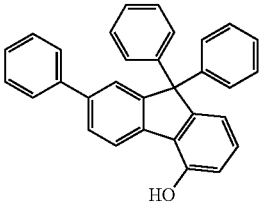 [SMILES: Oc1cccc2c1-c1ccc(-c3ccccc3)cc1C2(c1ccccc1)c1ccccc1] | 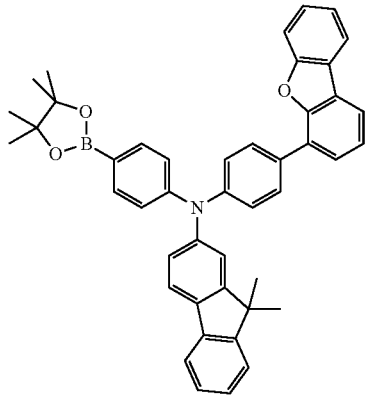 [SMILES: CC1(C)c2ccccc2-c2ccc(N(c3ccc(B4OC(C)(C)C(C)(C)O4)cc3)c3ccc(-c4cccc5c4oc4ccccc45)cc3)cc21] | 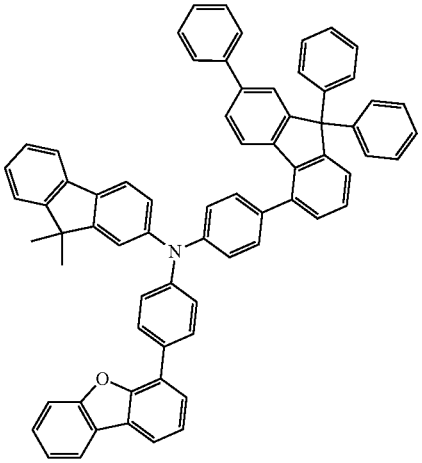<br>(2-5) | 65% |
| 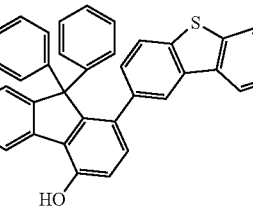 | 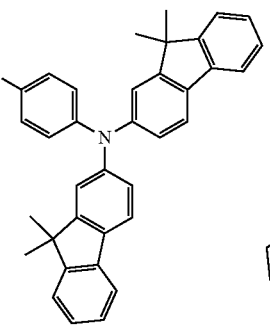 | 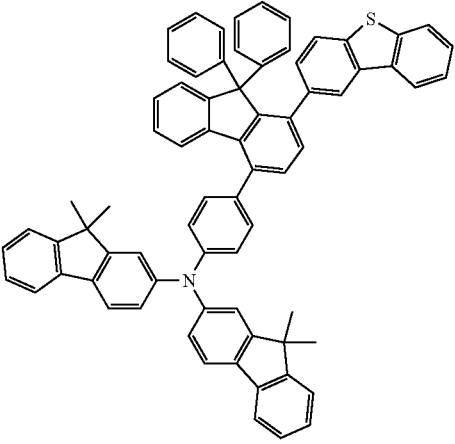<br>(2-6) | 52% |
Example 3
Synthesis of the Compound biphenyl-4-ylbiphenyl-2-yl-(5-{4-[(9,9-dimethyl-9H-fluoren-2-yl)phenylamino]phenyl}-9,9-diphenyl-9H-fluoren-2-yl)amine (3-1) and Compounds (3-2) to (3-6)
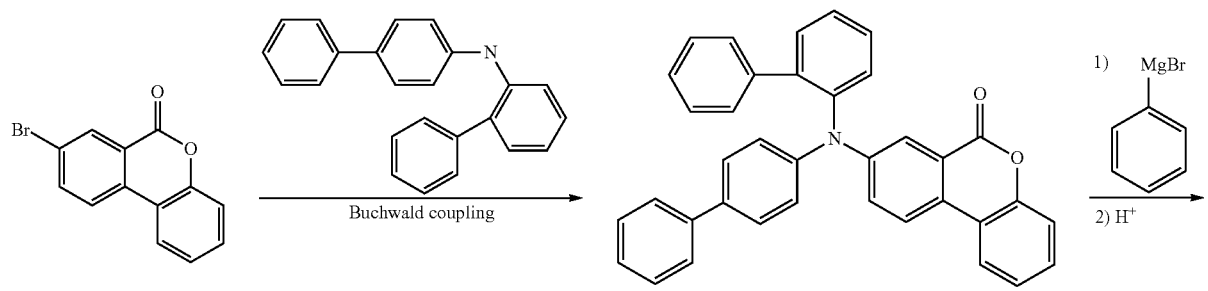

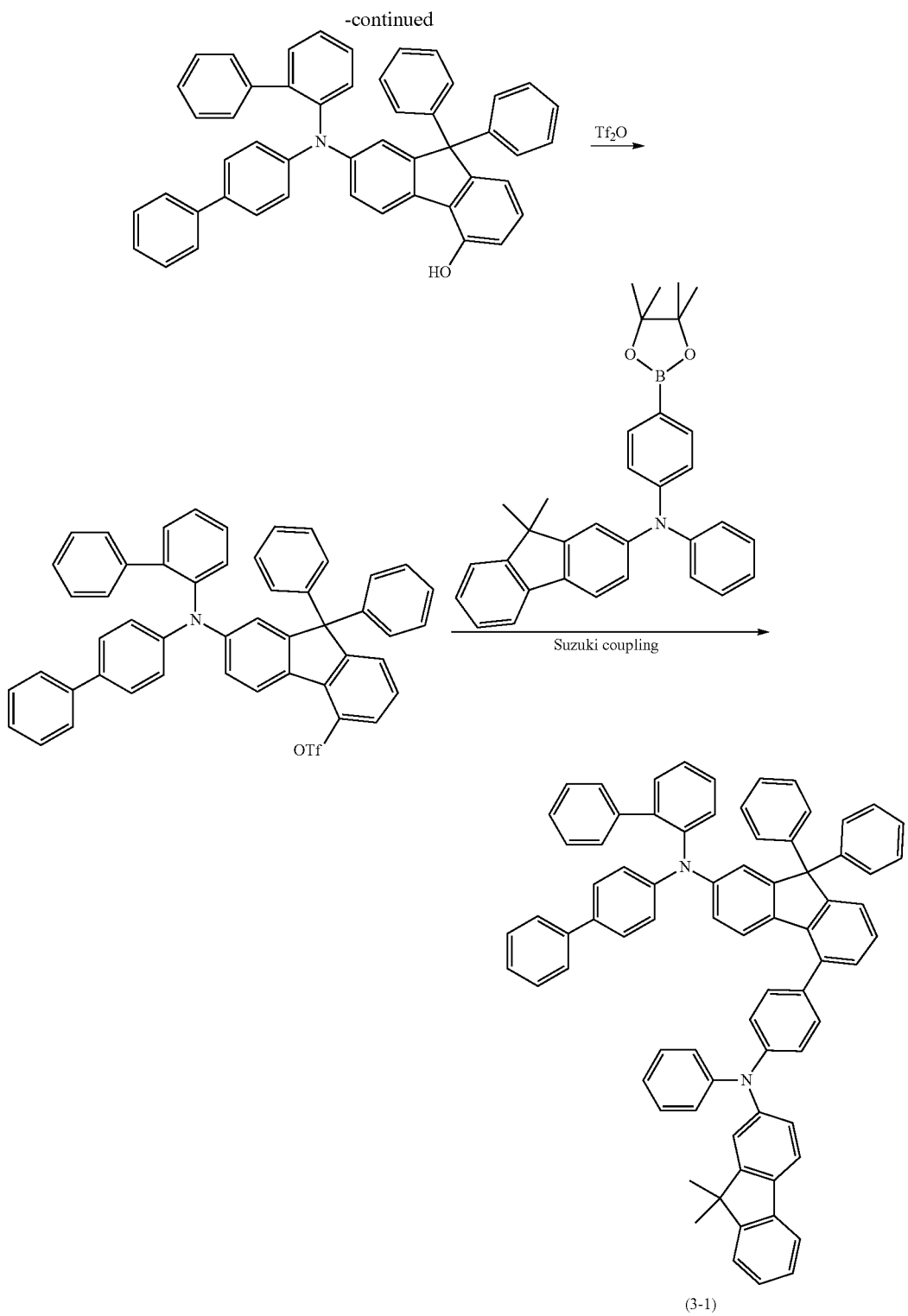

(3-1)

8-(Biphenyl-4-ylbiphenyl-2-ylamino)benzo[c]chromen-6-one 19.0 g of biphenyl-2-ylbiphenyl-4-ylamine (59 mmol) and 16.3 g of 8-bromobenzo[c]chromen-6-one (CAS: 1447543-95-4) (59 mmol) are dissolved in 400 ml of toluene. The solution is degassed and saturated with $N_2$. 2.36 ml (2.36 mmol) of a 1 M tri-tert-butylphosphine solution and 0.27 g (1.18 mmol) of palladium(II) acetate are then added. 11.6 g of sodium tert-butoxide (109 mmol) are subsequently added. The reaction mixture is heated at the boil under a protective atmosphere for 3 h. The mixture is subsequently partitioned between toluene and water, and the organic phase is washed three times with water, dried over $Na_2SO_4$ and

187 evaporated in a rotary evaporator. After filtration of the crude product through silica gel with toluene, the residue which remains is recrystallised from heptane/toluene. The yield is 27 g (90% of theory).

The following compounds are prepared analogously:

188

7-(Biphenyl-4-ylbiphenyl-2-ylamino)-9,9-diphenyl-9H-fluoren-4-ol

The following compounds are prepared analogously to 7-dibenzofuran-4-yl-9,9-diphenyl-9H-fluoren-4-ol:

| Starting material 1 | Starting material 2 | Product | Yield |
|---|---|---|---|
| | | | 90% |
| | | | 85% |
| | | | 75% |

| Starting material 1 | Starting material 2 | Product | Yield |
|---|---|---|---|
| | PhMgBr | | 83% |
| | PhMgBr | | 71% |
| | CH₃MgBr | | 66% |

Synthesis of the compound biphenyl-4-ylbiphenyl-2-yl-(5-{4-[(9,9-dimethyl-9H-fluoren-2-yl)phenylamino]phenyl}-9,9-diphenyl-9H-fluoren-2-yl)amine (3-1) and Compounds (3-2) to (3-5)
Compounds (3-1) to (3-5) are prepared analogously to the compound [4-(7-dibenzofuran-4-yl-9,9-diphenyl-9H-fluoren-4-yl)phenyl]-(9,9-dimethyl-9H-fluoren-2-yl)phenylamine (2-1):
| Starting material 1 | Starting material 2 | Product | Yield |
|---|---|---|---|
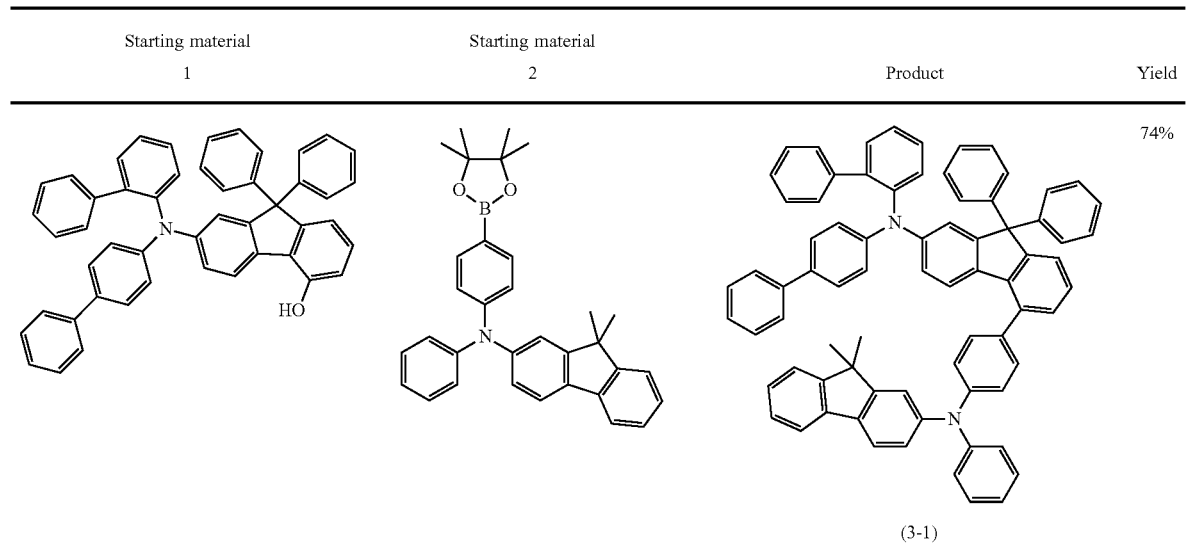
(3-1) 74%
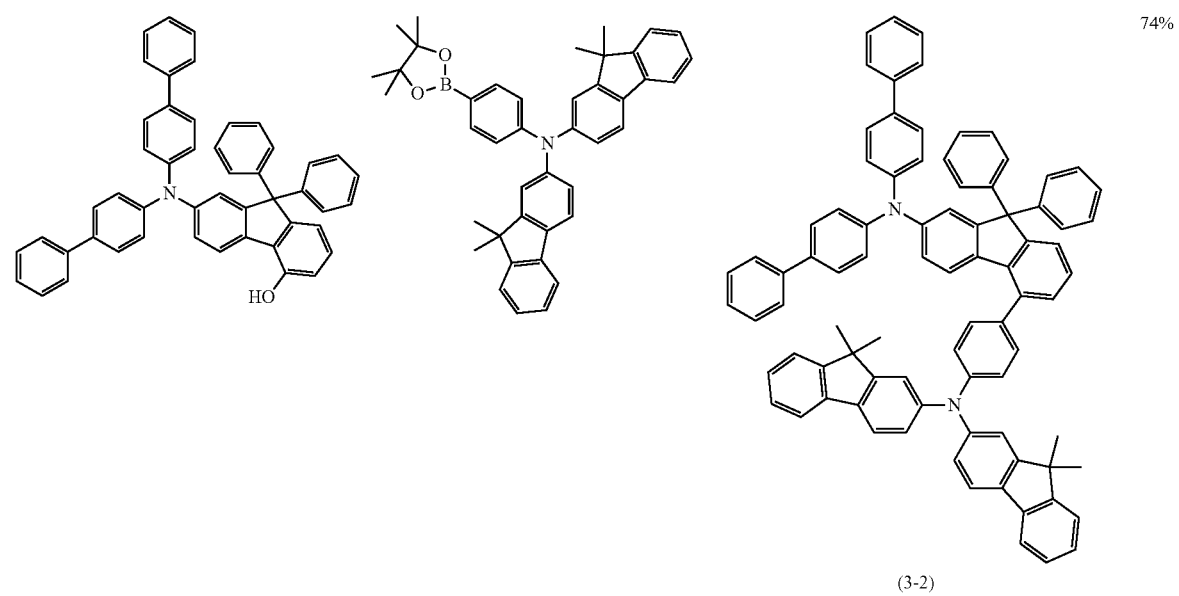
(3-2) 74%

-continued

| Starting material 1 | Starting material 2 | Product | Yield |
|---|---|---|---|
| | | | 72% |
| | | (3-3) | |
| | | | 68% |
| | | (3-4) | |
| | | | 72% |
| | | (3-5) | |

Example 4
Synthesis of the Compound biphenyl-4-yl-(9,9-dimethyl-9H-fluoren-2-yl)-{4-[9,9-dimethyl-4-(9-phenyl-9H-carbazol-3-yl)-9H-fluoren-1-yl]-phenyl}amine (4-1) and Compounds (4-2) to (4-3)
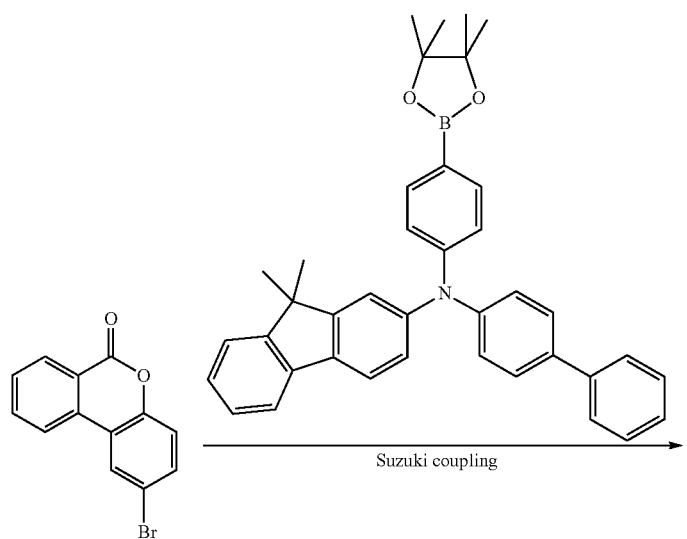
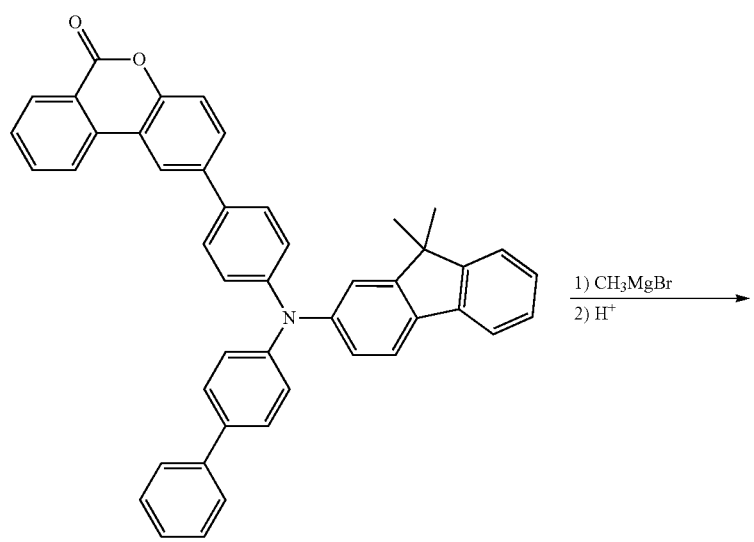

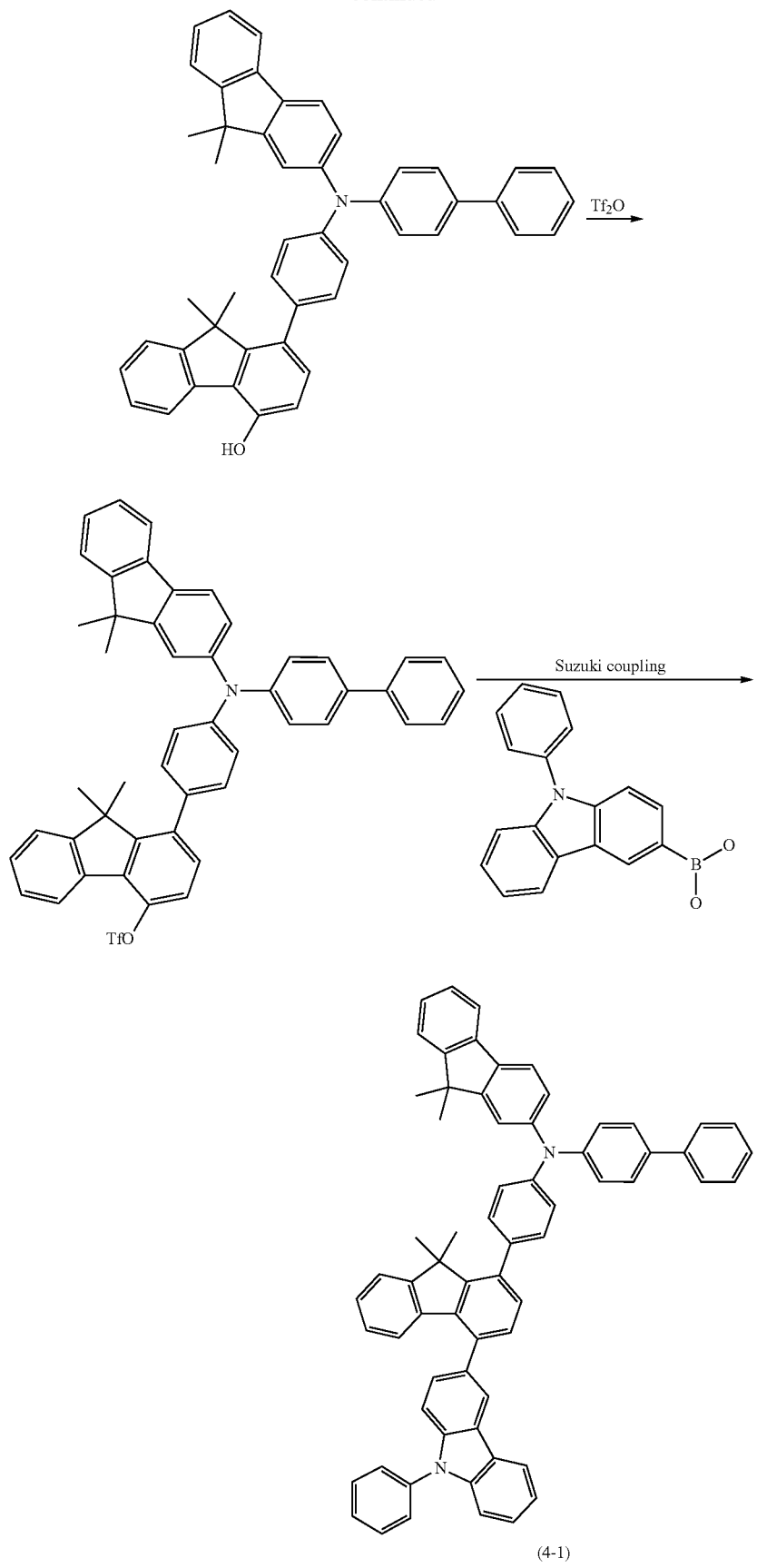
(4-1)

2-{4-[Biphenyl-4-yl-(9,9-dimethyl-9H-fluoren-2-yl)aminophenyl]}-benzo[c]chromen-6-one 20 g (35.5 mmol) of the pinacoloboronic ester derivative, 9.76 g (35.5 mmol) of 3-bromobenzo[c]chromen-6-one and 35 ml of a 2M $Na_2CO_3$ solution (71.6 mmol) are suspended in 600 ml of dioxane. 0.75 g (0.89 mmol) of 1,1-bis(diphenylphosphino)ferrocenepalladium(II) dichloride complex with DCM is added to this suspension, and the reaction mixture is heated under reflux for 14 h. After cooling, the organic phase is separated off, filtered through silica gel, washed three times with 100 ml of water and subsequently evaporated to dryness. After filtration of the crude product through silica gel with toluene, the residue which remains is recrystallised from heptane/toluene. The yield is 17.7 g (79% of theory).

The following compounds are prepared analogously:

| Starting material 1 | Starting material 2 | Product | Yield |
|---|---|---|---|
| | | | 80% |
| | | | 77% |

1-{4-[Biphenyl-4-yl-(9,9-dimethyl-9H-fluoren-2-yl)
amino]phenyl}-9,9-dimethyl-9H-fluoren-4-ol 1-{4-[Biphenyl-4-yl-(9,9-dimethyl-9H-fluoren-2-yl)
amino]phenyl}-9,9-dimethyl-9H-fluoren-4-ol is prepared analogously to the synthesis of 7-dibenzofuran-4-yl-9,9-diphenyl-9H-fluoren-4-ol described in Example 3:

| Starting material 1 | Starting material 2 | Product | Yield |
|---|---|---|---|
| | CH₃MgBr | | 84% |

The following compounds are prepared analogously:

| Starting material 1 | Starting material 2 | Product | Yield |
|---|---|---|---|
| | MgBr | | 64% |

| Starting material 1 | Starting material 2 | Product | Yield |
|---|---|---|---|
| 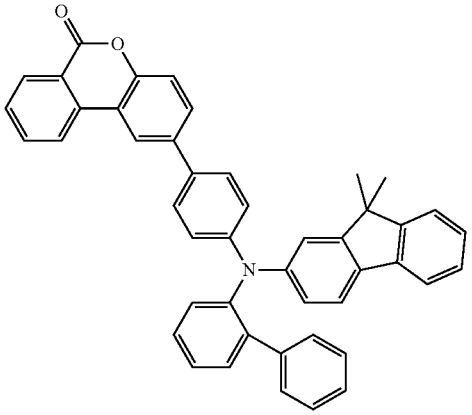 [SMILES: CC1(C)c2ccccc2-c2ccc(N(c3ccc(-c4ccc5oc(=O)c6ccccc6c5c4)cc3)c3ccccc3-c3ccccc3)cc21] | 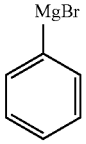 | 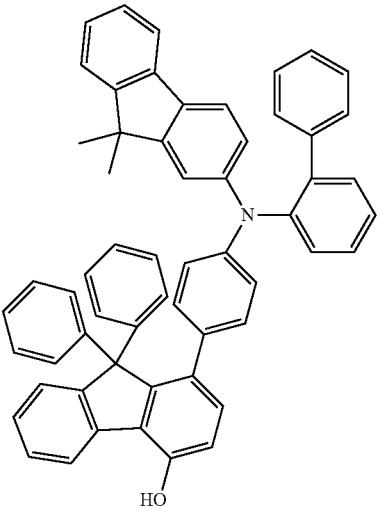 [SMILES: CC1(C)c2ccccc2-c2ccc(N(c3ccc(-c4ccc(O)c5c4C(c4ccccc4)(c4ccccc4)c4ccccc4-5)cc3)c3ccccc3-c3ccccc3)cc21] | 70% |
Synthesis of Compounds (4-1) to (4-4)
Compounds (4-1) to (4-4) are prepared analogously to compound [4-(7-dibenzofuran-4-yl-9,9-diphenyl-9H-fluoren-4-yl)phenyl]-(9,9-dimethyl-9H-fluoren-2-yl)phenylamine (2-1):
| Starting material 1 | Starting material 2 | Product | Yield |
|---|---|---|---|
| 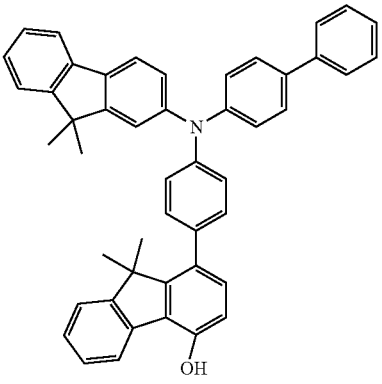 [SMILES: CC1(C)c2ccccc2-c2ccc(N(c3ccc(-c4ccccc4)cc3)c3ccc(-c4ccc(O)c5c4C(C)(C)c4ccccc4-5)cc3)cc21] | 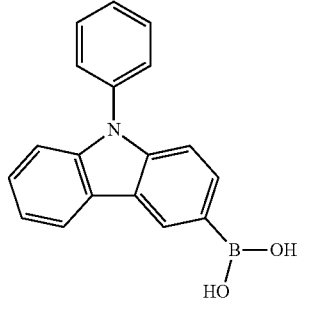 [SMILES: OB(O)c1ccc2c(c1)c1ccccc1n2-c1ccccc1] | 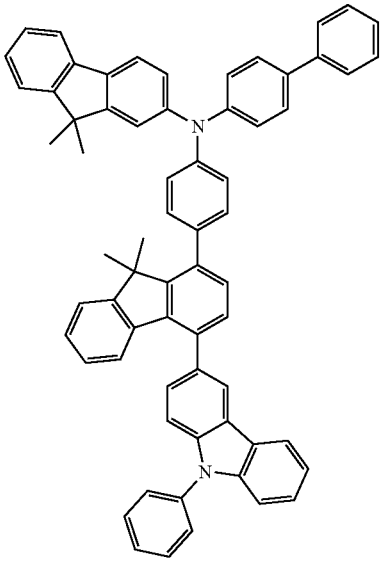<br>(4-1) | 80% |

| Starting material 1 | Starting material 2 | Product | Yield |
|---|---|---|---|
| 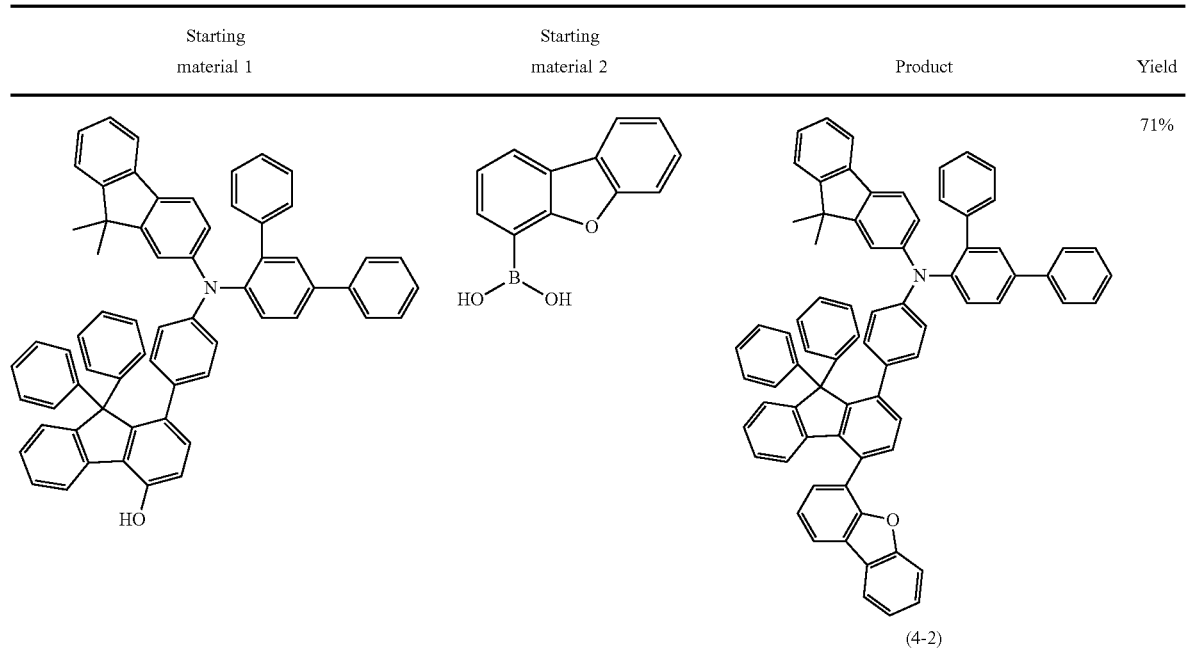 | | | 71%<br>75% |
(4-2)
(4-3)

Example 5
Comparative Examples
Synthesis of Comparative Compounds (V3) and (V4)
The following compounds (V3) and (V4) are also prepared analogously to the synthesis of compound (1-1) described in Example 1:
| Starting material 1 | Starting material 2 | Product | Yield |
|---|---|---|---|
| 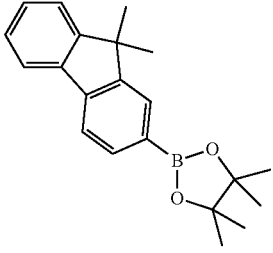 [SMILES: CC1(C)c2ccccc2-c2ccc(B3OC(C)(C)C(C)(C)O3)cc21] | 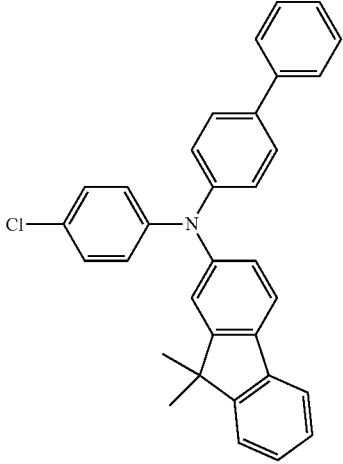 [SMILES: CC1(C)c2ccccc2-c2ccc(N(c3ccc(Cl)cc3)c3ccc(-c4ccccc4)cc3)cc21] | 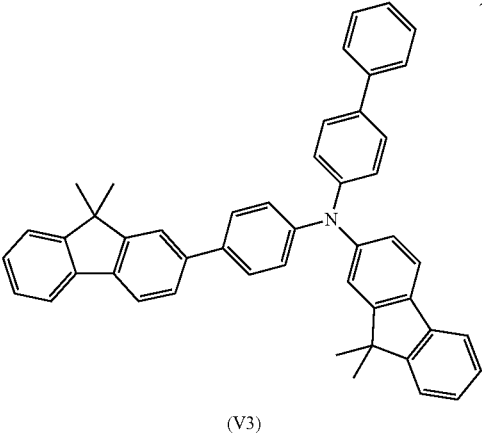 (V3) | 79% |
| 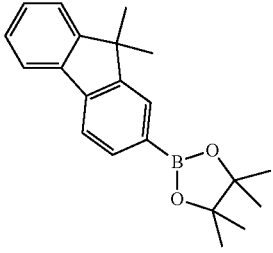 [SMILES: CC1(C)c2ccccc2-c2ccc(B3OC(C)(C)C(C)(C)O3)cc21] | 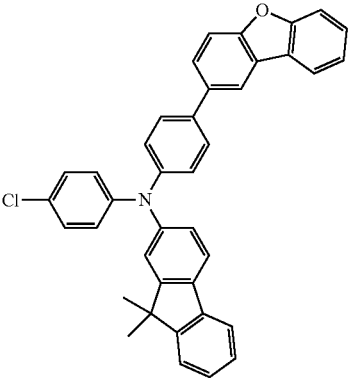 [SMILES: CC1(C)c2ccccc2-c2ccc(N(c3ccc(Cl)cc3)c3ccc(-c4ccc5oc6ccccc6c5c4)cc3)cc21] | 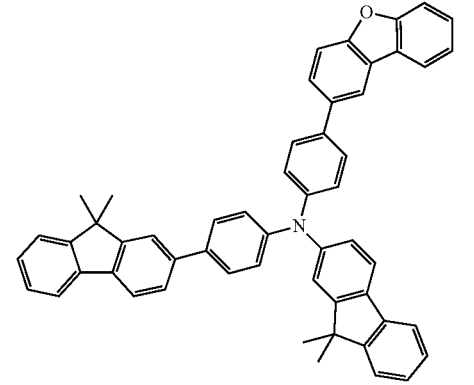 (V4) | 85% |

Synthesis of Comparative Compounds (V1) and (V2)

The following compounds (V1) and (V2) are also prepared analogously to the synthesis of intermediates described in Example 1:

| Starting material 1 | Starting material 2 | Product | Yield |
|---|---|---|---|
| (fluorene-Br) | (fluorene-NH-biphenyl) | (V1) | 79% |
| (fluorene-Br) | (fluorene-NH-fluorene) | (V2) | 75% |

Example 6

Production of OLEDs

OLEDs according to the invention and OLEDs in accordance with the prior art are produced by a general process in accordance with WO 04/058911, which is adapted to the circumstances described here (e.g. materials).

The data of various OLEDs are presented in the following inventive examples E1 to E4 and in reference examples V1-V4. The substrates used are glass plates which have been coated with structured ITO (indium tin oxide) in a thickness of 50 nm. The OLEDs basically have the following layer structure: substrate/p-doped hole-transport layer (HIL1)/hole-transport layer (HTL)/p-doped hole-transport layer (HIL2)/hole-transport layer (EBL)/emission layer (EML)/electron-transport layer (ETL)/electron-injection layer (EIL) and finally a cathode. The cathode is formed by an aluminium layer with a thickness of 100 nm. The materials required for the production of the OLEDs are shown in Table 1, the various component structures are shown in Table 2.

All materials are applied by thermal vapour deposition in a vacuum chamber. The emission layer here always consists of at least one matrix material (host material) and an emitting dopant (emitter) with which the matrix material or matrix materials is (are) admixed in a certain proportion by volume by co-evaporation. An expression such as H1:SEB (95%:5%) here means that material H1 is present in the layer in a proportion by volume of 95% and SEB is present in the layer in a proportion of 5%. Analogously, the electron-transport layer or the hole-injection layers may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression EQE @ 10 mA/cm$^2$ denotes the external quantum efficiency at a current density of 10 mA/cm$^2$. LT80 @ 60 mA/cm$^2$ is the lifetime by which the OLED has dropped to 80% of the initial intensity at a constant current of 60 mA/cm$^2$.

TABLE 1

Structures of the materials used

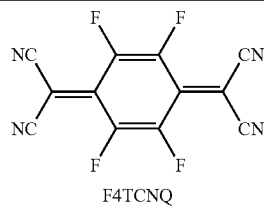

F4TCNQ

TABLE 1-continued
Structures of the materials used
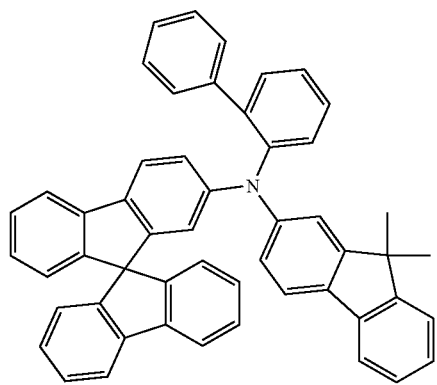
HIM
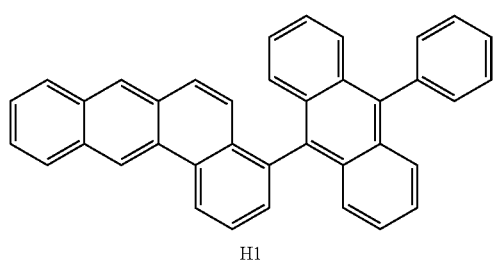
H1
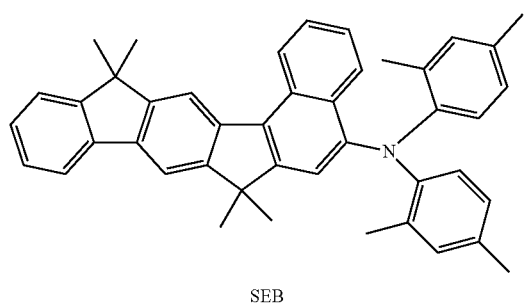 [SMILES: Cc1ccc(N(c2ccc(C)cc2C)c2cc3c(c4ccccc24)-c2cc4c(cc2C3(C)C)-c2ccccc2C4(C)C)c(C)c1]
SEB
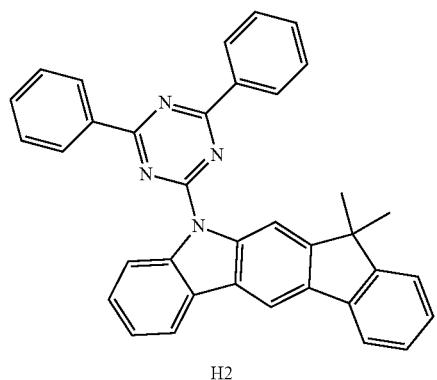
H2
TABLE 1-continued
Structures of the materials used
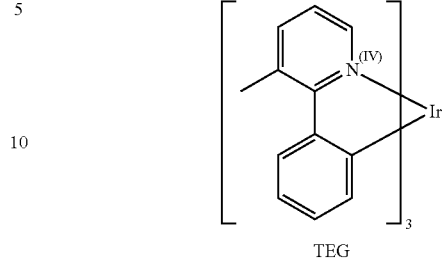
TEG
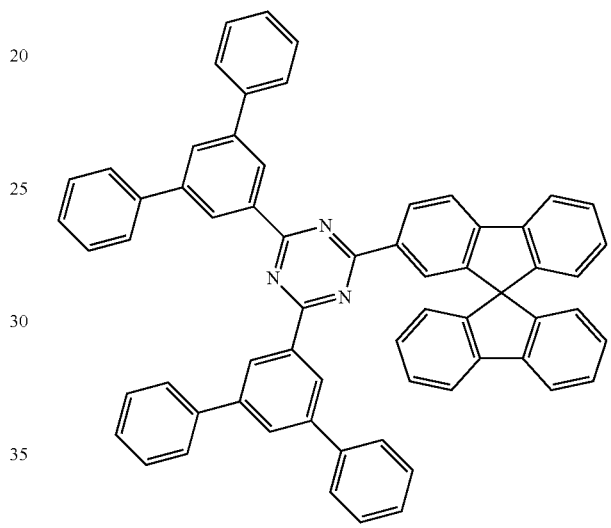
ETM
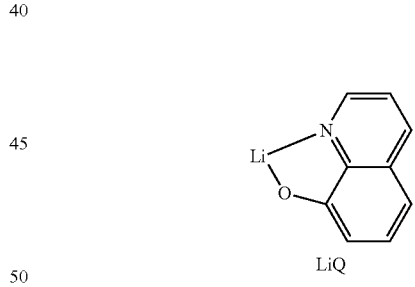
LiQ
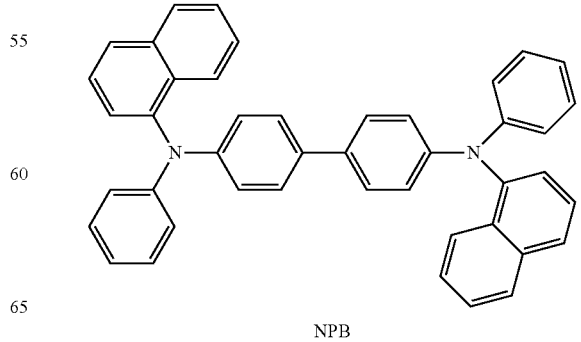
NPB TABLE 1-continued
Structures of the materials used
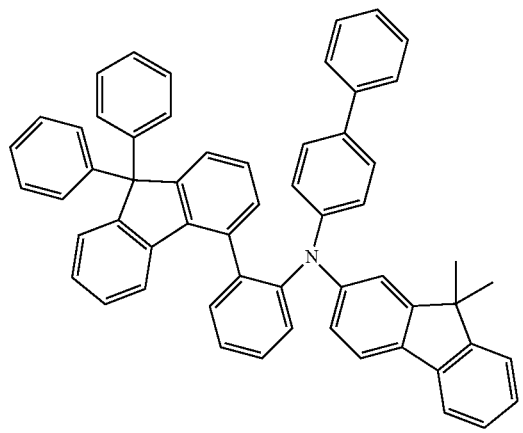
HTM1
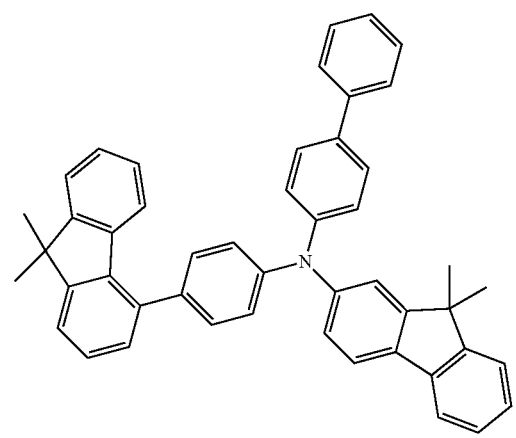
HTM2
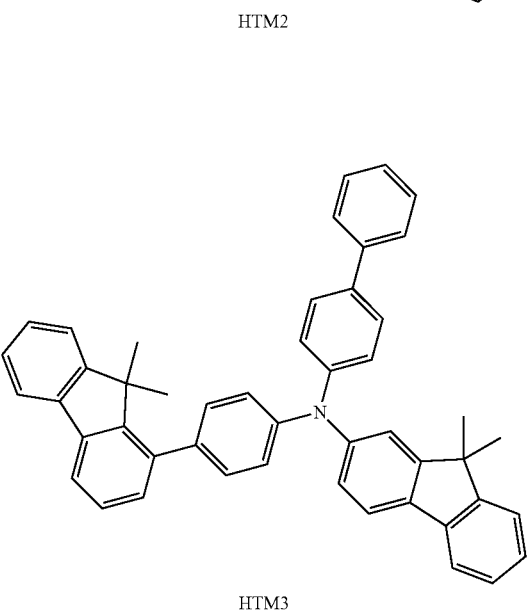
HTM3
TABLE 1-continued
Structures of the materials used
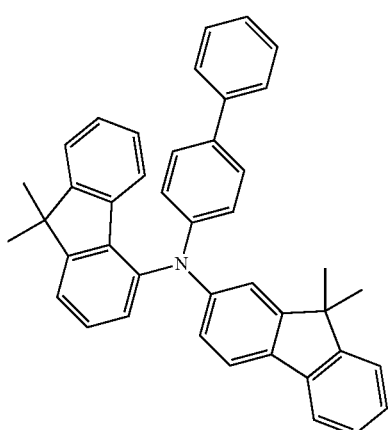
HTMV1
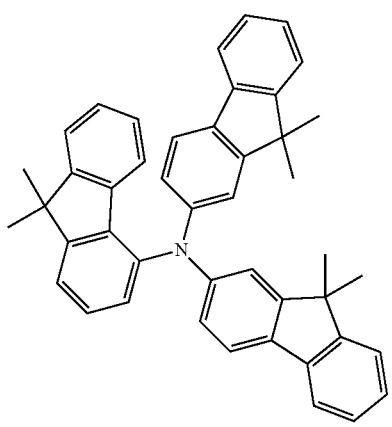
HTMV2
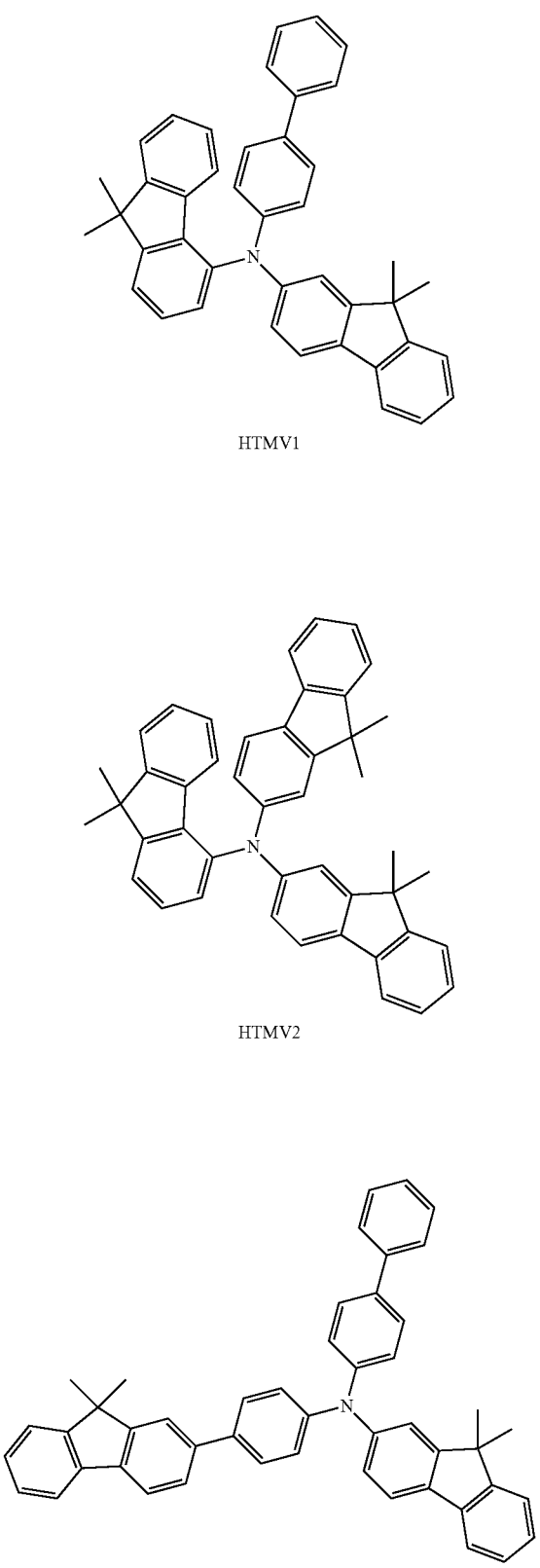
HTMV3

TABLE 1-continued

Structures of the materials used

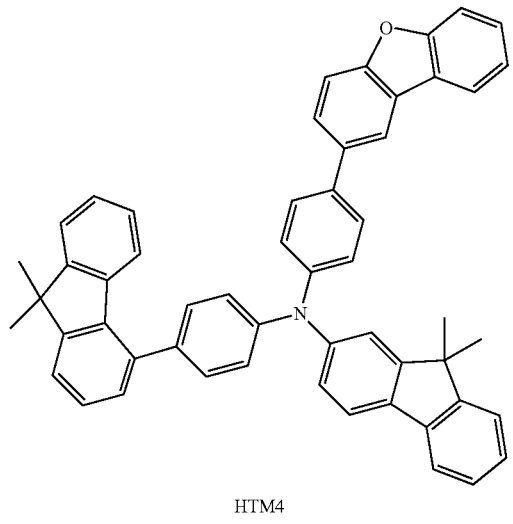

HTM4

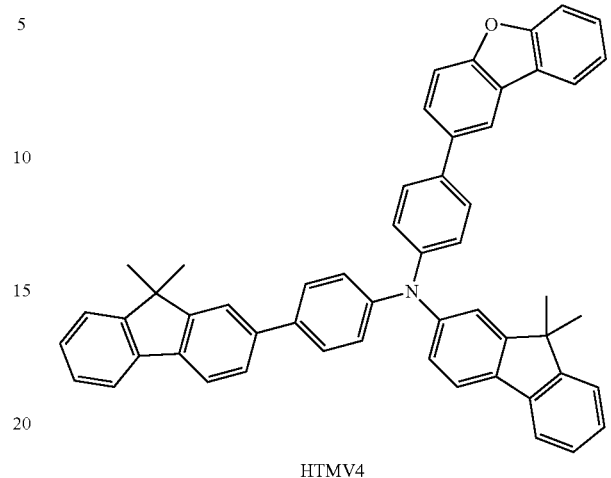

HTMV4

TABLE 2

Structure of the OLEDs: HIL1(HIM:F4TCNQ(5%)-20 nm)/HTL/HIL2/EBL/EML/ETL(ETM)/EIL(Liq-1 nm)

| Ex. | HTL Thickness/nm | HIL2 Thickness/nm | EBL Thickness/nm | EML Thickness/nm | ETL Thickness/nm |
|---|---|---|---|---|---|
| V1 | HIM 155 nm | NPB:F4TCNQ(5%) 20 nm | NPB 20 nm | H1:SEB(5%) 20 nm | ETM:LiQ(50%) 30 nm |
| E1 | HIM 155 nm | HTM1:F4TCNQ(5%) 20 nm | HTM1 20 nm | H1:SEB1(5%) 20 nm | ETM:LiQ(50%) 30 nm |
| E2 | HIM 155 nm | HTM2:F4TCNQ(5%) 20 nm | HTM2 20 nm | H1:SEB1(5%) 20 nm | ETM:LiQ(50%) 30 nm |
| E3 | HIM 155 nm | HTM3:F4TCNQ(5%) 20 nm | HTM3 20 nm | H1:SEB1(5%) 20 nm | ETM:LiQ(50%) 30 nm |
| V2 | HIM 155 nm | HTMV1:F4TCNQ(5%) 20 nm | HTMV1 20 nm | H1:SEB1(5%) 20 nm | ETM:LiQ(50%) 30 nm |
| V3 | HIM 155 nm | HTMV2:F4TCNQ(5%) 20 nm | HTMV2 20 nm | H1:SEB1(5%) 20 nm | ETM:LiQ(50%) 30 nm |
| V4 | HIM 155 nm | HTMV3:F4TCNQ(5%) 20 nm | HTMV3 20 nm | H1:SEB1(5%) 20 nm | ETM:LiQ(50%) 30 nm |
| E4 | HIM 155 nm | HTM4:F4TCNQ(5%) 20 nm | HTM4 20 nm | H1:SEB1(5%) 20 nm | ETM:LiQ(50%) 30 nm |
| V5 | HIM 155 nm | HTMV4:F4TCNQ(5%) 20 nm | HTMV4 20 nm | H1:SEB1(5%) 20 nm | ETM:LiQ(50%) 30 nm |
| E5 | HIM 210 nm | HTM1:F4TCNQ(5%) 20 nm | HTM1 20 nm | H2:TEG(10%) 30 nm | ETM:LIQ(50%) 40 nm |
| E6 | HIM 210 nm | HTM2:F4TCNQ(5%) 20 nm | HTM2 20 nm | H2:TEG(10%) 30 nm | ETM:LiQ(50%) 40 nm |
| V6 | HIM 210 nm | NPB:F4TCNQ(5%) 20 nm | NPB 20 nm | H2:TEG(10%) 30 nm | ETM:LiQ(50%) 40 nm |
| V7 | HIM 210 nm | HTMV1:F4TCNQ(5%) 20 nm | HTMV1 20 nm | H2:TEG(10%) 30 nm | ETM:LiQ(50%) 40 nm |

In a singlet blue component, samples E1 (8.5%), E2 (9.4%) and E3 (9.2%) according to the invention exhibit a higher quantum efficiency at 10 mA/cm² compared with reference samples V1 (6.2%), V2 (8.1%), V3 (8.1%) and V4 (7.5%). The lifetime LT80 at 60 mA/cm² is significantly better in the case of samples according to the invention E1 (250 h), E2 (282 h) and E3 (260 h) than reference samples V1 (125 h), V2 (216 h), V3 (170 h) and V4 (195 h).

In a singlet blue component, sample E4 (8.8%) according to the invention exhibits a higher quantum efficiency at 10 mA/cm² compared with reference sample V5 (8.3%). The lifetime LT80 at 60 mA/cm² is significantly better in the case of sample E4 according to the invention (240 h) than reference sample V5 (195 h).

In a triplet green component, reference samples V6 (11.7%) and V7 (20.3%) exhibit in some cases considerably lower quantum efficiencies at 2 mA/cm² than samples according to the invention E5 (21.2%) and E6 (21.8%). The lifetime (80%) at 20 mA/cm² of samples according to the invention E5 (115 h) and E6 (105 h) is also longer than in the case of V6 (80 h) and V7 (100 h).

The invention claimed is:

1. A compound of the formula (1)

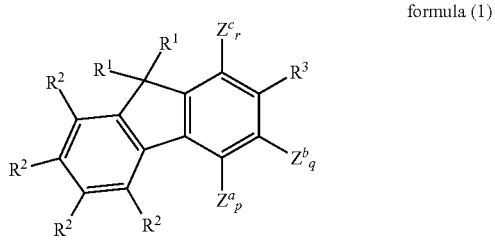

formula (1)

where the following applies to the symbols and indices used:

$R^1$ is on each occurrence, identically or differently, preferably identically, H, D, F, Cl, Br, I, C(=O)$R^4$, CN, Si($R^4$)$_3$, NO$_2$, P(=O)($R^4$)$_2$, S(=O)$R^4$, S(=O)$_2$$R^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups is optionally replaced by —$R^4$C=C$R^4$—, —C≡C—, Si($R^4$)$_2$, C=O, C=S, C=N$R^4$, —C(=O)O—, —C(=O)N$R^4$—, P(=O)($R^4$), —O—, —S—, SO or SO$_2$ and where one or more H atoms in the above-mentioned groups is optionally replaced by D, F, Cl, Br, I, CN or NO$_2$, or an aromatic or heteroaromatic ring system having 5 to 30 aromatic ring atoms, which may in each case be substituted by one or more radicals $R^4$, or an aryloxy group having 5 to 60 aromatic ring atoms, which is optionally substituted by one or more radicals $R^4$, or an aralkyl group having 5 to 60 aromatic ring atoms, which may in each case be substituted by one or more radicals $R^4$, where the two radicals $R^1$ is optionally linked to one another and may form a ring, so that a spiro compound forms in position 9 of the fluorene, where spirobifluorenes are excluded;

$R^2$ and $R^3$ are on each occurrence, identically or differently, preferably identically, H, D, F, Cl, Br, I, C(=O)$R^4$, CN, Si($R^4$)$_3$, NO$_2$, P(=O)($R^4$)$_2$, S(=O)$R^4$, S(=O)$_2$$R^4$, N($R^4$)$_2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups is optionally replaced by —$R^4$C=C$R^4$—, —C≡C—, Si($R^4$)$_2$, C=O, C=S, C=N$R^4$, —C(=O)O—, —C(=O)N$R^4$—, P(=O)($R^4$), —O—, —S—, SO or SO$_2$ and where one or more H atoms in the above-mentioned groups is optionally replaced by D, F, Cl, Br, I, CN or NO$_2$, or an aromatic or heteroaromatic ring system having 5 to 30 aromatic ring atoms, which may in each case be substituted by one or more radicals $R^4$, or an aryloxy group having 5 to 60 aromatic ring atoms, which is optionally substituted by one or more radicals $R^4$, or an aralkyl group having 5 to 60 aromatic ring atoms, which may in each case be substituted by one or more radicals $R^4$, where two or more radicals $R^2$ or two or more radicals $R^3$ is optionally linked to one another and may form a ring;

$R^4$ is on each occurrence, identically or differently, H, D, F, Cl, Br, I, C(=O)$R^5$, CN, Si($R^5$)$_3$, NO$_2$, P(=O)($R^5$)$_2$, S(=O)$R^5$, S(=O)$_2$$R^5$, N($R^5$)$_2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^5$ and where one or more CH$_2$ groups in the above-mentioned groups is optionally replaced by —$R^5$C=C$R^5$—, —C≡C—, Si($R^5$)$_2$, C=O, C=S, C=N$R^5$, —C(=O)O—, —C(=O)N$R^5$—, P(=O)($R^5$), —O—, —S—, SO or SO$_2$ and where one or more H atoms in the above-mentioned groups is optionally replaced by D, F, Cl, Br, I, CN or NO$_2$, or an aromatic or heteroaromatic ring system having 5 to 30 aromatic ring atoms, which may in each case be substituted by one or more radicals $R^5$, or an aryloxy or heteroaryloxy group having 5 to 30 aromatic ring atoms, which is optionally substituted by one or more radicals $R^5$;

$R^5$ is selected from the group consisting of H, D, F, an aliphatic hydrocarbon radical having 1 to 20 C atoms or an aromatic or heteroaromatic ring system having 5 to 30 C atoms, in which one or more H atoms is optionally replaced by D or F, where two or more adjacent substituents $R^5$ may form a mono- or polycyclic, aliphatic ring system with one another;

p and r are each 0;

q is 1;

$Z^a_p$ and $Z^c_r$ are, identically or differently on each occurrence, equal to $R^3$;

$Z^b_q$ is equal to

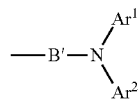

B' is a phenylene, biphenylene, terphenylene, naphthylene, dibenzofuranylene or dibenzo-thiophenylene group, which is optionally substituted by one or more radicals $R^4$;

Ar$^1$ and Ar$^2$ are on each occurrence, identically or differently, an aromatic group having 6 to 60 ring atoms or a heteroaromatic group having 5 to 60 ring atoms, each of which is optionally substituted by one or more radicals R$^6$, which are identical to or different from one another, where at least one of the two groups Ar$^1$ and Ar$^2$ must contain a fluorene group;
wherein Ar$^1$ and Ar$^2$ contain no carbazoles;
R$^6$ is on each occurrence, identically or differently, H, D, F, Cl, Br, I, C(=O)R$^5$, CN, Si(R$^5$)$_3$, NO$_2$, P(=O)(R$^5$)$_2$, S(=O)R$^5$, S(=O)$_2$R$^5$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^5$ and where one or more CH$_2$ groups in the above-mentioned groups is optionally replaced by —R$^5$C=CR$^5$—, —C≡C—, Si(R$^5$)2, C=O, C=S, C=NR$^5$, —C(=O)O—, —C(=O)NR$^5$—, P(=O)(R$^5$), —O—, —S—, SO or SO$_2$ and where one or more H atoms in the above-mentioned groups is optionally replaced by D, F, Cl, Br, I, CN or NO$_2$, or an aromatic or heteroaromatic ring system having 5 to 30 aromatic ring atoms, which may in each case be substituted by one or more radicals R$^5$, or an aryloxy or heteroaryloxy group having 5 to 30 aromatic ring atoms, which is optionally substituted by one or more radicals R$^5$.

2. The compound according to claim 1, wherein the compound has the general formula (2)

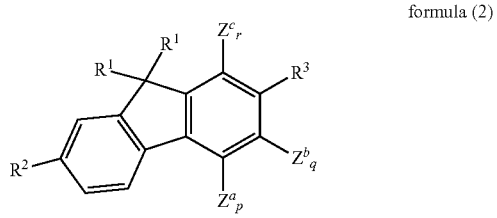

formula (2)

where the definitions from claim 1 apply to the symbols used.

3. The compound according to claim 1, wherein the compound has the general formula (7)

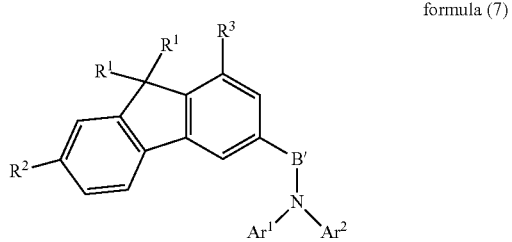

formula (7)

where the definitions from claim 1 apply to the symbols used.

4. The compound according to claim 1, wherein the compound has the general formula (10)

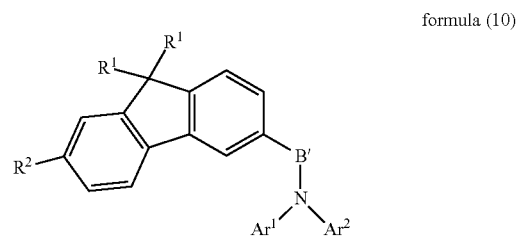

formula (10)

where the definitions from claim 1 apply to the symbols used.

5. The compound according to claim 1, wherein both R$^1$ are identical.

6. The compound according to claim 1, wherein both groups Ar$^1$ and Ar$^2$ contain at least two aromatic or heteroaromatic rings.

7. Process for the preparation of a compound according to claim 1 by means of one-step Buchwald coupling by reaction of a fluorene derivative containing a leaving group with Ar$^2$—NH—Ar$^1$.

8. A process for the preparation of the compound according to claim 1 by means of two-step Buchwald coupling by stepwise reaction of a fluorene derivative containing a leaving group with (1) Ar$^2$—NH$_2$ and (2) NH$_2$—Ar$^1$.

9. A process for the preparation of the compound according to claim 1, wherein the compound is prepared from a benzochromen-6-one.

10. A formulation comprising at least one compound according to claim 1 and at least one solvent.

11. An oligomer, polymer or dendrimer comprising one or more compounds according to claim 1, where the bond(s) to the polymer, oligomer or dendrimer is optionally localized at any position in formula (1) that are substituted by R$^1$ to R$^6$.

12. A composition comprising one or more compounds according to claim 1 and at least one further material selected from the group consisting of fluorescent emitters, phosphorescent emitters, host materials, matrix materials, electron-transport materials, electron-injection materials, hole-conductor materials, hole-injection materials, electron-blocking materials, hole-blocking materials and p-dopants.

13. The process according to claim 10 comprising the following steps:
  a) adding an organometallic compound onto a benzochromen-6-one and subsequent
  b) acid-catalysed cyclisation to give a 4-hydroxyfluorene derivative and subsequent
  c) converting the hydroxyl group in position 4 of the fluorene into a leaving group and subsequent, and
  d) converting the fluorene into the desired product.

14. An electronic device comprising at least one compound according to claim 1.

* * * * *